(12) United States Patent
Segars et al.

(10) Patent No.: US 11,872,267 B2
(45) Date of Patent: Jan. 16, 2024

(54) TREATMENT OF UTERINE FIBROIDS USING PURIFIED COLLAGENASE

(71) Applicants: The Johns Hopkins University, Baltimore, MD (US); Duke University, Durham, NC (US); BioSpecifics Technologies LLC, Malvern, PA (US)

(72) Inventors: James H. Segars, Baltimore, MD (US); Phyllis Carolyn Leppert, Salt Lake City, UT (US); Thomas L. Wegman, N. Merrick, NY (US); Jean-Marie Soma, Lynbrook, NY (US)

(73) Assignees: The Johns Hopkins University, Baltimore, MD (US); Duke University, Durham, NC (US); BioSpecifics Technologies LLC, Malvern, PA (US)

(*) Notice: Subject to any disclaimer, the term of this patent is extended or adjusted under 35 U.S.C. 154(b) by 232 days.

(21) Appl. No.: 17/070,747

(22) Filed: Oct. 14, 2020

(65) Prior Publication Data

US 2021/0113670 A1  Apr. 22, 2021

Related U.S. Application Data

(60) Provisional application No. 62/915,360, filed on Oct. 15, 2019.

(51) Int. Cl.
*A61K 38/48* (2006.01)
*A61P 15/00* (2006.01)
(Continued)

(52) U.S. Cl.
CPC ........ *A61K 38/4886* (2013.01); *A61K 9/0019* (2013.01); *A61K 9/0021* (2013.01);
(Continued)

(58) Field of Classification Search
CPC .............. A61K 38/4886; A61K 9/0019; A61K 9/0021; A61K 9/0034; C12Y 304/24003; A61B 5/4824; A61P 15/00
See application file for complete search history.

(56) References Cited

U.S. PATENT DOCUMENTS 3,821,364 A  6/1974  Chiulli et al.
4,524,065 A  6/1985  Pinnell
(Continued)

FOREIGN PATENT DOCUMENTS

AU  2012200863 A1  3/2012
CA  2 308 842 A1  12/2000
(Continued)

OTHER PUBLICATIONS

Peddada et al., "Growth of uterine leiomyomata among premenopausal black and white women", Dec. 16, 2008, Proc Natl Acad Sci, 105 (50), p. 19887-09892. Cited in IDS filed Mar. 10, 2021. (Year: 2008).*
(Continued)

*Primary Examiner* — Gary B Nickol
*Assistant Examiner* — Amelia Nicole Dickens
(74) *Attorney, Agent, or Firm* — BakerHostetler

(57) ABSTRACT

Disclosed herein are compositions and methods for treating uterine fibroids in vivo, and methods of reducing symptoms associated with uterine fibroids, including pain, bleeding and infertility. The disclosed compositions comprise collagenase in an amount effective to cause shrinkage and/or reduce stiffness of uterine fibroids.

12 Claims, 37 Drawing Sheets
(20 of 37 Drawing Sheet(s) Filed in Color)
Specification includes a Sequence Listing.

(51) Int. Cl.
    *A61K 9/00*      (2006.01)
    *A61B 5/00*      (2006.01)
(52) U.S. Cl.
    CPC ............ *A61K 9/0034* (2013.01); *A61P 15/00*
            (2018.01); *A61B 5/4824* (2013.01); *C12Y*
                                    *304/24003* (2013.01)

(56) References Cited

U.S. PATENT DOCUMENTS

| | | | |
|---|---|---|---|
| 5,252,481 | A | 10/1993 | Holjevac et al. |
| 5,256,140 | A | 10/1993 | Fallick |
| 5,589,171 | A | 12/1996 | Wegman |
| 5,830,741 | A | 11/1998 | Dwulet et al. |
| 6,086,872 | A | 7/2000 | Wegman |
| 7,811,560 | B2 | 10/2010 | Sabatino |
| 10,369,110 | B2 * | 8/2019 | Leppert ............. A61K 38/4886 |
| 2003/0022856 | A1 | 1/2003 | Richardson et al. |
| 2003/0026844 | A1 | 2/2003 | Lee et al. |
| 2005/0227910 | A1 | 10/2005 | Yang et al. |
| 2006/0251581 | A1 | 11/2006 | McIntyre |
| 2007/0003541 | A1 | 1/2007 | Faudoa |
| 2007/0224183 | A1 | 9/2007 | Sabatino et al. |
| 2009/0053276 | A1 | 2/2009 | Richard |
| 2010/0021416 | A1 | 1/2010 | Lichter et al. |
| 2010/0035868 | A1 | 2/2010 | Jabbour |
| 2010/0086971 | A1 | 4/2010 | Suppmann et al. |
| 2012/0315265 | A1 | 12/2012 | Lai et al. |
| 2013/0129663 | A1 | 5/2013 | Friberg et al. |
| 2013/0195828 | A1 | 8/2013 | Kibbe et al. |
| 2013/0217789 | A1 | 8/2013 | Taylor et al. |
| 2013/0287759 | A1 | 10/2013 | Munoz Montano |
| 2014/0271612 | A1 * | 9/2014 | Leppert ................... A61P 35/00 424/94.67 |
| 2016/0000890 | A1 * | 1/2016 | Yu ........................... A61P 17/00 206/568 |
| 2020/0078310 | A1 * | 3/2020 | Leppert ................ A61K 9/0034 |
| 2021/0023014 | A1 * | 1/2021 | Leppert .................. A61K 38/43 |
| 2021/0060143 | A1 * | 3/2021 | Yu ........................... A61K 47/32 |
| 2021/0220284 | A1 * | 7/2021 | Leppert .................... A61K 9/48 |

FOREIGN PATENT DOCUMENTS

| | | |
|---|---|---|
| CA | 2 643 171 A1 | 9/2007 |
| EP | 0468411 A2 | 1/1992 |
| EP | 2130551 B1 | 9/2009 |
| EP | 2133415 A1 | 12/2009 |
| JP | 2002530873 A | 9/2002 |
| JP | 2011528716 A | 11/2011 |
| RU | 2180002 C2 | 2/2002 |
| WO | 0030182 A1 | 5/2000 |
| WO | 2006121968 A2 | 11/2006 |
| WO | 2007089851 A2 | 8/2007 |
| WO | 2007/100675 A3 | 9/2007 |
| WO | 2010011605 A2 | 1/2010 |
| WO | 2011/130537 A2 | 10/2011 |
| WO | 2012/031245 A1 | 3/2012 |
| WO | 2012041512 A1 | 4/2012 |
| WO | 2013059619 A1 | 4/2013 |
| WO | 2014144859 A1 | 9/2014 |
| WO | 2015/108901 A1 | 7/2015 |

OTHER PUBLICATIONS

Marsh et al., "Racial differences in fibroid prevalence and ultrasound findings in asymptomatic young women (18-30 years old): a pilot study", Jun. 2013, Fertil. Steril., 99 (7), p. 1951-1957. Cited in IDS filed Mar. 10, 2021. (Year: 2013).*

Spies et al., "The UFS-QOL, a new disease-specific symptom and health-related quality of life questionnaire for leiomyomata", Feb. 2002, Obstet Gynecol, 99 (2), p. 290-300. Cited in IDS filed Mar. 10, 2021. (Year: 2002).*

Singh et al., "Patient-reported outcomes of a phase 1 clinical trial of injectable collagenase clostridium histolyticum (EN3835) for treatment of uterine fibroids", Sep. 25, 2019, Fertility and Sterility, 112(3), p. e344. (Year: 2019).*

Jayes et al. "Loss of stiffness in collagen-rich uterine fibroids after digestion with purified collagenase Clostridium histolyticum", Nov. 2016, Am J Obstet Gynecol, 215, p. 596.e1-8. (Year: 2016).*

Murji et al. "Selective progesterone receptor modulators (SPRMs) for uterine fibroids", 2017, Cochrane Database of Systematic Reviews, 4, p. 4-22. (Year: 2017).*

Courtoy et al. "Matrix Metalloproteinase Activity Correlates With Uterine Myoma Volume Reduction After Ulipristal Acetate Treatment", Feb. 1, 2018, J Clin Endocrinol Metab, 103(4), p. 1566-1573. (Year: 2018).*

Murji et al. "Selective progesterone receptor modulators (SPRMs) for uterine fibroids", 2017, Cochrane Database of Systematic Reviews, Issue 4, p. 1-83. (Year: 2017).*

Denton and Kumar. "Autophagy-dependent cell death", published online Dec. 19, 2018, Cell Death and Differentiation, vol. 26, p. 605-616. (Year: 2018).*

Peixoto et al. "Epigenetic Control of Autophagy in Cancer Cells: A Key Process for Cancer-Related Phenotypes", published online Dec. 17, 2019, Cells, vol. 8, p. 1-30. (Year: 2019).*

Ali et al. "1,25 Dihydroxyvitamin D3 Enhances the Antifibroid Effects of Ulipristal Acetate in Human Uterine Fibroids", published online Dec. 4, 2018, Reproductive Science, vol. 26 No. 6, p. 812-828. (Year: 2018).*

Abedin et al., Type V collagen: the presence of appreciable amounts of alpha 3(V) chain in uterus, Biochem Biophys Res Commun, (1981), 102 (4), pp. 1237-1245.

Aitken et al., The normal human myometrium has a vascular spatial gradient absent in small fibroids, Hum. Reprod., (2006), 21 (10), pp. 2669-2678.

Arici et al., Transforming growth factor-beta3 is expressed at high levels in leiomyoma where it stimulates fibronectin expression and cell proliferation, Fertil Steril, (2000), 73 (5), pp. 1006-1011.

Arslan et al., Gene expression studies provide clues to the pathogenesis of uterine leiomyoma: new evidence and a systematic review, Hum Reprod, (2005), 20 (4), pp. 852-863.

Badalamente et al., Efficacy and safety of injectable mixed collagenase subtypes in the treatment of Dupuytren's contracture, J Hand Surg Am, (2007), 32 (6), pp. 767-774.

Bae et al., "On-off" thermocontrol of solute transport. I. Temperature dependence of swelling of N-isopropylacrylamide networks modified with hydrophobic components in water, Pharm Res, (1991), 8 (4), pp. 531-537.

Baird et al., High cumulative incidence of uterine leiomyoma in black and white women: ultrasound evidence, Am J Obstet Gynecol, (2003), 188 (1), pp. 100-107.

Barker et al., Proteoglycans in Leiomyoma and Normal Myometrium: Abundance, Steroid Hormone Control, and Implications for Pathophysiology, Reprod Sci, (2016), 23 (3), pp. 302-309.

Berto et al., A comparative analysis of structure and spatial distribution of decorin in human leiomyoma and normal myometrium, Biochim Biophys Acta—Gen Subj, (2003), 1619 (1), pp. 98-112.

Bolgen et al., Cryogelation for preparation of novel biodegradable tissue-engineering scaffolds, Biomater Sci Polym Ed, (2007), 18 (9), pp. 1165-1179.

Borth et al., Human serum inhibitors of collagenase as revealed by preparative isoelectric focusing, Clin Chim Acta, (1981), 117 (2), pp. 219-225.

Bouwsma et al., Comparing focused ultrasound and uterine artery embolization for uterine fibroids-rationale and design of the Fibroid Interventions: reducing symptoms today and tomorrow (FIRSTT) trial, Fertil Steril, (2011), 96 (3), pp. 704-710.

Bromley et al., Collagenase: an experimental study of intervertebral disc dissolution, Spine, (1980), 5 (2), pp. 126-136.

Cardozo et al., The estimated annual cost of uterine leiomyomata in the United States, Am J Obstet Gynecol, (2012), 206 (3), pp. 211.e1-211.e9.

Catherino et al., Microarray analysis in fibroids: which gene list is the correct list?, Fertil Steril, (2003), 80 (2), pp. 293-294.

(56) References Cited

OTHER PUBLICATIONS

Catherino et al., Reduced dermatopontin expression is a molecular link between uterine leiomyomas and keloids, Genes Chromosom Cancer, (2004), 40 (3), pp. 204-217.
Chen et al., A novel selective progesterone receptor modulator asoprisnil (J867) inhibits proliferation and induces apoptosis in cultured human uterine leiomyoma cells in the absence of comparable effects on myometrial cells, J Clin Endocrinol Metab, (2006), 91 (4), pp. 1296-1304.
Chudnoff et al., Outpatient procedure for the treatment and relief of symptomatic uterine myomas, Obstet Gynecol, (2013), 121 (5), pp. 1075-1082.
Chung et al., Collagen fibril formation. A new target to limit fibrosis, J Biol Chem, (2008), 283 (38), pp. 25879-25886.
Chwalisz et al., Selective progesterone receptor modulator development and use in the treatment of leiomyomata and endometriosis, Endocrine Reviews, (2005), 26 (3), pp. 423-438.
Chwalisz et al., A randomized, controlled trial of asoprisnil, a novel selective progesterone receptor modulator, in women with uterine leiomyomata, Fertility & Sterility, (2007), 87 (6), pp. 1399-1412.
Coyne et al., A meaningful response on the uterine fibroid symptom and health-related quality of life questionnaire (UFSQOL), Fertil Steril, (2018), 110 (4), pp. e135-e136.
Das et al., Expression of transforming growth factor-beta isoforms (beta 2 and beta 3) in the mouse uterus: analysis of the periimplantation period and effects of ovarian steroids, Endocrinology, (1992), 130 (6), pp. 3459-3466.
Drayer et al., Prevalence, morbidity, and current medical management of uterine leiomyomas, Int J Gynaecol Obstet, (2015), 131 (2), pp. 117-122.
Evans et al., "Feeling the force" in reproduction: Mechanotransduction in reproductive processes, Connect Tissue Res, (2016), 57 (3), pp. 236-244.
Feng et al., Improved quality of life is partly explained by fewer symptoms after treatment of fibroids with mifepristone, Int J Gynaecol Obstet, (2010), 109 (2), pp. 121-124.
Fennessy et al., Quality-of-life assessment of fibroid treatment options and outcomes, Radiology, (2011), 259 (3), pp. 785-792.
Flake et al., The natural history of uterine leiomyomas: light and electron microscopic studies of fibroid phases, interstitial ischemia, inanosis, and reclamation, Obstet Gynecol Int, (2013), 528376, 20 pages.
Flake et al., The natural history of uterine leiomyomas: morphometric concordance with concepts of interstitial ischemia and inanosis, Obstet Gynecol Int, (2013), 285103, 9 pages.
Frey et al., Dendritic polyglycerol: a new versatile biocompatible-material, Rev. Mal. Biotechnol., (2002), 90 (3-4), pp. 257-267.
Friedman et al., Degradation of porcine dermal connective tissue by collagenase and by hyaluronidase, Br J Dermatol, (1986), 115 (4), pp. 403-408.
Gabbiani, The myofibroblast in wound healing and fibrocontractive diseases, J Pathol, (2003), 200 (4), pp. 500-503.
Gabbiani et al., Collagen and myofibroblasts of granulation tissue. A chemical, ultrastructural and immunologic study, Virchows Arch B Cell Pathol, (1976), 21 (2), pp. 133-145.
Geever et al., The synthesis, characterisation, phase behaviour and swelling of temperature sensitive physically crosslinked poly(1-vinyl-2-pyrrolidinone)/poly(N-isopropylacrylamide) hydrogels, Eur Polym J, (2006), 42 (1), pp. 69-80.
Gelbard et al., Clinical efficacy, safety, and tolerability of collagenase clostridium histolyticum for the treatment of peyronie disease in 2 large double-blind, randomized, placebo controlled phase 3 studies, J Urol, (2013), 190 (1), pp. 199-207.
Giray et al., Comparison of Nerve Fiber Density between Patients with Uterine Leiomyoma with and without Pain: a Prospective Clinical Study, Geburtshilfe Frauenheilkd, (2018), 78 (4), pp. 407-411.
Graham et al., Tritium labeling of antisense oligonucleotides by exchange with tritiated water, Nucleic Acid Res, (1993), 21 (16), pp. 3737-3743.
Han et al., Molecular mechanism of type I collagen homotrimer resistance to mammalian collagenases, J Biol Chem, (2010), 285 (29), pp. 22276-22281.
Harding et al., The responsiveness of the uterine fibroid symptom and health-related quality of life questionnaire (UFS-QOL), Health Qual Life Outcomes, (2008), 6, 99.
Hatefi et al., Biodegradable injectable in situ forming drug delivery systems, Journal of controlled Release, (2002), 80 (1-3), pp. 9-28.
Heinonen et al., Multiple clinical characteristics separate MED12-mutation-positive and -negative uterine leiomyomas, Sci Rep, (2017), 7 (1), 1015.
Heinonen et al., Global metabolomic profiling of uterine leiomyomas, Br J Cancer, (2017), 117 (12), pp. 1855-1864.
Hennessy et al., Non-Hodgkin lymphoma: an update, Lancet Oncol, (2004), 5 (6), pp. 341-353.
Ho et al., Fibrosis—a lethal component of systemic sclerosis, Nat Rev Rheumatol, (2014), 10 (7), pp. 390-402.
Hodge et al., Molecular and cytogenetic characterization of plexiform leiomyomata provide further evidence for genetic heterogeneity underlying uterine fibroids, Am J Pathol, (2008), 172 (5), pp. 1403-1410.
Holdsworth-Carson et al., Differences in the cellular composition of small versus large uterine fibroids, Reproduction, (2016), 152 (5), pp. 467-480.
Huang et al., Novel Nanogels with Both Thermoresponsive and Hydrolytically Degradable Properties, Macromolecules, (2008), 41 (22), pp. 8339-8345.
Islam et al., Extracellular matrix in uterine leiomyoma pathogenesis: a potential target for future therapeutics, Hum Reprod Update, (2018), 24 (1), pp. 59-85.
Jamaluddin et al., Proteomic Profiling of Human Uterine Fibroids Reveals Upregulation of the Extracellular Matrix Protein Periostin, Endocrinology, (2018), 159 (2), pp. 1106-1118.
Jamaluddin et al., Proteomic Characterization of the Extracellular Matrix of Human Uterine Fibroids, Endocrinology, (2018), 159 (7), pp. 2656-2669.
Brunengraber et al., "Injectable Clostridium Histolyticum Collagenase as a Potential Treatment for Uterine Fibroids," Reproductive Sciences, vol. 21, No. 12, Dec. 2014, pp. 1452-1459.
Singh et al., "Patient-reported outcomes of a phase 1 clinical trial of injectable collagenase clostridium histolyticum (EN3835) for treatment of uterine fibroids," Fertility and Sterility, Elsevier, vol. 112, No. 3, Sep. 1, 2019, 1 Page.
Jayes et al., Evidence of biomechanical and collagen heterogeneity in uterine fibroids, PLOS One, (2019), 14 (4), e0215646.
Jemal et al., Cancer statistics, 2005, CA Cancer J Clin, (2005), 55 (1), pp. 10-30.
Jenison et al., Oligonucleotide inhibitors of P-selectin-dependent neutrophil-platelet adhesion, Antisense & Nucleic Acid Drug Dev, (1998), 8 (4), pp. 265-279.
Ioffe et al., Endometrial changes from short-term therapy with CDB-4124, a selective progesterone receptor modulator, Mod Pathol, (2009), 22 (3), pp. 450-459.
Jorge et al., Mechanical signaling in reproductive tissues: mechanisms and importance, Reprod Sci, (2014), 21 (9), pp. 1093-1107.
Joseph et al., Myometrial cells undergo fibrotic transformation under the influence of transforming growth factor beta-3, Fertil Steril, (2010), 93 (5), pp. 1500-1508.
Kainthan et al., Synthesis, Characterization, and Viscoelastic Properties of High Molecular Weight Hyperbranched Polyglycerols, Macromolecules, (2006), 39 (22), pp. 7708-7717.
Kamel et al., Overhydroxylation of Lysine of Collagen Increases Uterine Fibroids Proliferation: Roles of Lysyl Hydroxylases, Lysyl Oxidases, and Matrix Metalloproteinases, Biomed Res Int, (2017), 5316845, 13 pages.
Kohori et al., Preparation and characterization of thermally responsive block copolymer micelles comprising poly(N-isopropylacrylamide-b-DL-lactide), Journal of Controlled Release, (1998), 55 (1), pp. 87-98.
Konishi et al., Ultrastructural study of minute uterine leiomyomas, Int J Gynecol Pathol, (1983), 2 (2). pp. 113-120.
Kose et al., Keloids and hypertrophic scars: are they two different sides of the same coin?, Dermatol Surg, (2008), 34 (3), pp. 336-346.

(56) References Cited

OTHER PUBLICATIONS

Kuroda et al., Dermatopontin expression is decreased in hypertrophic scar and systemic sclerosis skin fibroblasts and is regulated by transforming growth factor-beta1, interleukin-4, and matrix collagen, J Invest Dermatol, (1999), 112 (5), pp. 706-710.
Lacomb et al., Phase Matching considerations in Second Harmonic Generation from tissues: Effects on emission directionality, conversion efficiency and observed morphology, Opt Commun, (2008), 281 (7), pp. 1823-1832.
Latha et al., Physicochemical properties of extracellular matrix proteins in post-burn human granulation tissue, Comp Biochem Physiol B Biochem Mol Biol, (1999), 124 (3), pp. 241-249.
Laughlin et al., Prevalence of uterine leiomyomas in the first trimester of pregnancy: an ultrasound-screening study, Obstet. Gynecol., (2009), 113 (3), pp. 630-635.
Lee et al., In situ-gelling, erodible N-isopropylacrylamide copolymers, Macromol Biosci, (2005), 5 (7), pp. 629-635.
Lee et al., Human leiomyoma smooth muscle cells show increased expression of transforming growth factor-beta 3 (TGF beta 3) and altered responses to the antiproliferative effects of TGF beta, J Clin Endocrinol Metab, (2001), 86 (2), pp. 913-920.
Leppert et al., A new hypothesis about the origin of uterine fibroids based on gene expression profiling with microarrays, Am J Obstet Gynecol, (2006), 195 (2), pp. 415-420.
Le Ray et al., End-chain radiolabeling and in vitro stability studies of radiolabeled poly(hydroxy acid) nanoparticles, J. Pharm. Sci., (1994), 83 (6), pp. 845-851.
Makareeva et al., Carcinomas contain a matrix metalloproteinase-resistant isoform of type I collagen exerting selective support to invasion, Cancer Res, (2010), 70 (11), pp. 4366-4374.
Makinen et al., MED12, the mediator complex subunit 12 gene, is mutated at high frequency in uterine leiomyomas, Science, (2011), 334 (6053), pp. 252-255.
Malik et al., Novel method to characterize primary cultures of leiomyoma and myometrium with the use of confirmatory biomarker gene arrays, Fertil Steril, (2007), 87 (5), pp. 1166-1172.
Malik et al., Why leiomyomas are called fibroids: the central role of extracellular matrix in symptomatic women, Semin Reprod Med, (2010), 28 (3), pp. 169-179.
Malik et al., Integrin β1 regulates leiomyoma cytoskeletal integrity and growth, Matrix Biol, (2012), 31 (7-8), pp. 389-397.
Mallya et al., Kinetics of hydrolysis of type I, II, and III collagens by the class I and II Clostridium histolyticum collagenases, J Protein Chem, (1992), 11 (1), pp. 99-107.
Markowski et al., Cell culture and senescence in uterine fibroids, Cancer Genet Cytogenet, (2010), 202 (1), pp. 53-57.
Marsh et al., Racial differences in fibroid prevalence and ultrasound findings in asymptomatic young women (18-30 years old): a pilot study, Fertil. Steril., (2013), 99 (7), pp. 1951-1957.
Matchar et al., Management of uterine fibroids, Evid Rep Technol Assess (Summ), (2001), (34), pp. 1-6.
Mccarthy-Keith et al., Gonadotropinreleasing hormone agonist increases expression of osmotic response genes in leiomyoma cells, Fertil Steril, (2011), 95 (7), pp. 2383-2387.
Mcguire et al., Whole exome sequencing in a random sample of North American women with leiomyomas identifies MED12 mutations in majority of uterine leiomyomas, PLOS One, (2012), 7 (3), e33251, 6 pages.
Mehine et al., Characterization of uterine leiomyomas by whole-genome sequencing, N Engl J Med, (2013), 369 (1), pp. 43-53.
Mehine et al., Clonally related uterine leiomyomas are common and display branched tumor evolution, Hum Mol Genet, (2015), 24 (15), pp. 4407-4416.
Mitsiades et al., Focus on multiple myeloma, Cancer Cell, (2004), 6 (5), pp. 439-444.
Miyabashi et al., Chemonucleolysis with collagenase: a radiographic and pathologic study in dogs, Vet Surg, (1992), 21 (3), pp. 189-194.
Moulin et al., Normal skin wound and hypertrophic scar myofibroblasts have differential responses to apoptotic inductors, J Cell Physiol, (2004), 198 (3), pp. 350-358.
Mulabecirovic et al., In Vitro Comparison of Five Different Elastography Systems for Clinical Applications, Using Strain and Shear Wave Technology, Ultrasound in Med. and Biol., (2016), 42 (11), pp. 2572-2588.
Munro, Uterine leiomyomas, current concepts: pathogenesis, impact on reproductive health, and medical, procedural, and surgical management, Obstet Gynecol Clin North Am, (2011), 38 (4), pp. 703-731.
Nagase et al., Interaction of alpha 2-macroglobulin with matrix metalloproteinases and its use for identification of their active forms, Ann NY Acad Sci, (1994), 732, pp. 294-302.
Naitoh et al., Gene expression in human keloids is altered from dermal to chondrocytic and osteogenic lineage, Genes Cells, (2005), 10 (11), pp. 1081-1091.
Ng et al., A-Kinase Anchoring Protein 13 (AKAP13) Augments Progesterone Signaling in Uterine Fibroid Cells, J. Clin. Endocrinol. Metab., (2019), 104 (3), pp. 970-980.
Norian et al., Transforming growth factor beta3 regulates the versican variants in the extracellular matrix-rich uterine leiomyomas, Reprod Sci, (2009), 16 (12), pp. 1153-1164.
Oudshoorn et al., Synthesis and characterization of hyperbranched polyglycerol hydrogels, Biomaterials, (2006), 27 (32), pp. 5471-5479.
Paluch et al., Mechanotransduction: use the force(s), BMC Biol, (2015), 13:47, 14 pages.
Peddada et al., Growth of uterine leiomyomata among premenopausal black and white women, Proc Natl Acad Sci U S A, (2008), 105 (50), pp. 19887-19892.
Pfaffl, A new mathematical model for relative quantification in real-time RT-PCR, Nucleic Acids Res, (2001), 29 (9), e45, 6 pages.
Protic et al., Possible involvement of inflammatory/reparative processes in the development of uterine fibroids, Cell Tissue Res, (2016), 364 (2), pp. 415-427.
Sabry et al., Medical treatment of uterine leiomyoma, Reprod Sci, (2012), 19 (4), pp. 339-353.
Sasaki et al., A novel selective progesterone receptor modulator asoprisnil activates tumor necrosis factor-related apoptosis-inducing ligand (TRAIL)-mediated signaling pathway in cultured human uterine leiomyoma cells in the absence of comparable effects on myometrial cells, J Clin Endocrinol Metab, (2007), 92 (2), pp. 616-623.
Schindelin et al., Fiji: an open-source platform for biological-image analysis, Nature methods, (2012), 9 (7), pp. 676-682.
Schmittgen et al., Effect of experimental treatment on housekeeping gene expression: validation by real-time, quantitative RT-PCR, J Biochem Biophys Methods, (2000), 46 (1-2), pp. 69-81.
Jeong, B. et al., 2000, "Thermogelling biodegradable polymers with hydrophillic backbones: PEG-g-PLGA." Macromolecules 33:8317-8322. specfic. p. 8317, 8320.
Stewart, E. A., Jan. 27, 2001, "Uterine fibroids." The Lancet 357:293-298, specif. p. 293.
Taylor, D. K., et al., 2011. "Temperature-responsive biocompatible copolymers incorporating hyperbranched polyglycerols for adjustable functionality." Journal of Functional Biomaterials 2:173-194, specif. pp. 173, 174.
Thomas, A. et al. 2010. The emerging role of Clostridium histolyticum collagenase in the treatment of Dupuytren disease. Therapeutics and Clinical Risk Management 6: 557-572. specif. pp. 557, 560, 561, 562, 565.
Office Action in JP application No. 2019-072161 with English translation dated May 12, 2020, 17 pages.
International Search Report and Written Opinion issued in PCT/US2016/051670 dated Nov. 21, 2016, 12 pages.
Canadian Office Action issued in CA 2,907,255 dated Feb. 23, 2017, 7 pages.
Taylor, D., et al., "Putting the Moose on the Table: Understanding the Molecular Biology of Uterine Fibroids and Development of Non-invasion Treatment," XP055257658, 64 pages, Oct. 28, 2012.

(56) References Cited

OTHER PUBLICATIONS

Taylor, D., et al., "Treatment for Uterine Fibroids: Searching for Effective Drug Therapies," Drug Discovery Today Therapeutic Strategies, vol. 9, No. 1, pp. e41-849, 2012.
Jayes, F. L., et al., "Treatment of Uterine Fibroids with Highly Purified Clostridal Collagenase," Fertility and Sterility, vol. 98, No. 3, p. S232, XP055127058, Oct. 24, 2012.
Taylor, D., et al., "Recent scientific advances in leiomyoma (uterine fibroids) research facilitates better understanding and management," F1000Research, XP055257667, 11 pages, Jul. 6, 2015.
Extended European Search Report, issued in EP 16150076.4 dated Mar. 31, 2016, 11 pages.
Canadian First Examination Report issued in CA 2,907,255 dated Dec. 23, 2015, 7 pages.
Bonnerjea, J., et al., "Protein purification: the right step at the right time," Biotechnology, V. 4, 1986, pp. 954, 956 and 958.
Kågedal, L., et al., "Chemical, physical, and chromatographic properties of Superdex 75 prep grade and Superdex 200 prep grade gel filtration media," J. of Chromatography A, V. 537, 1991, pp. 17-32.
Office Action issued in Canadian application No. 2,643,171, dated Mar. 1, 2012, 3 pages.
International Search Report and Written Opinion in corresponding application No. PCT/US2012/029492, dated Aug. 20, 2012, 19 pages.
International Search Report and Written Opinion in corresponding application No. PCT/US2014/029448, dated Jul. 23, 2014, 8 pages.
Notice of Acceptance for Australian patent application No. 2015261743 dated Aug. 21, 2017, 3 pages.
Office Action in Japanese application No. 2016-503099 dated Jan. 5, 2018, 7 pages.
Office Action in Japanese application No. 2015-245310 dated Jan. 19, 2018, 13 pages.
Office Action in Japanese application No. 2016-503099 dated Dec. 7, 2018, 8 pages.
Office Action in Japanese application No. 2015-245310 dated Dec. 4, 2018, 9 pages.
Behera, MD, M.A., et al., "Thrombospondin-1 and Thrombospondin-2 mRNA and TSP-1 and TSP-2 Protein Expression in Uterine Fibroids and Correlation to the Genes COL1A1 and COL3A1 and to the Collagen Cross-link Hydroxyproline," Reproductive Sciences, vol. 14, No. 8S, pp. 63-76 (Dec. 2007).
Brunengraber, MD, L.N et al., "Injectable Clostridium Histolyticum Collagenase as a Potential Treatment for Uterine Fibroids," Reproductive Sciences, vol. 21(12), pp. 1452-1459 (2014).
Jorge, Soledad, et al., "Mechanical Signaling in Reproductive Tissues: Mechanisms and Importance," Reproductive Sciences, vol. 21(9), pp. 1093-1107 (2014).
Leppert, P.C., et al., "The Extracellular Matrix Contributes to Mechanotransduction in Uterine Fibroids," Hindawi Publishing Corporation, vol. 2014, Article ID 783289, pp. 1-12 (Jul. 3, 2014).
Norian, J.M., et al., "Characterization of tissue biomechanics and mechanical signaling in uterine leiomyoma," Matrix Biol., 31(1): 57-65, 12 pages. (Jan. 9, 2011).
Peavey, MD, M., et al., "Collagen-Binding α II Integrin Expression in Human Myometrium and Fibroids Utilizing a Novel RNA In Situ Probe," Reproductive Sciences vol. 21(9) pp. 1139-1144, (2014).
Rogers, BS, R., et al., "Mechanical homeostasis is altered in uterine leiomyoma," Am. J. Obstet. Gynecol., 198(4): 474.e1-474.11, 22 pages (Apr. 2008).
Thorne, J.T., et al., "Dynamic Reciprocity Between Cells and Their Microenvironment in Reproduction," Biology of Reproduction, 92(1), Article 25, pp. 1-10, online before print Nov. 19, 2014. DOI 10.1095/bioreprod.114.121368.
Jayes, DVM, PhD, F.L., et al., "Loss of stiffness in collagen-rich uterine fibroids after digestion with purified collagenase Clostridium histolyticum," American Journal of Obstetrics & Gynecology, 1.e1, 8 pages (2016).

Leppert MD, PhD, P.C. et al., "Comparative ultrastructure of collagen fibrils in uterine leiomyomas and normal myometrium," Fertil Steril, 82(3), pp. 1182-1187 (Oct. 2004).
Cuggino, J. C., et al., "Synthesis, charaterization and slow drug delivery of hydrogels based in N-acryloyl-tris-(hydroxymethyl) aminomethane and N-isopropyl acrylamide," Reactive & Functional Polymers, vol. 71, 2011, pp. 440-446.
Gill, H. S., & Prausnitz, M. R., "Does needle size matter?," Journal of Diabetes Science and Technology, vol. 1 (5), Sep. 2007, pp. 725-729.
Madan, M., et al., "In situ forming polymeric drug delivery systems," Indian Journal of Pharmaceutical Sciences, vol. 71(3), May-Jun. 2009, pp. 242-251.
Nguyen, M. K., & Lee D. S., "Injectable biodegradable hydrogels," Macromol. Biosci., vol. 10, 2010, pp. 563-579.
Examination Report dated Jun. 8, 2018, in Canadian application No. 2,907,255, 5 pages.
PCT International Search Report, issued in PCT/US2015/011296 dated Jun. 11, 2015, 3 pages.
Australian First Examination Report issued in AU 2015261743 dated Aug. 22, 2016, 4 pages.
Japanese Office Action issued in JP 2016 547001 dated Sep. 20, 2018, with English translation, 7 pages.
Examination Report No. 1 in Australian application No. 2014228477 dated May 22, 2018, 3 pages.
Communication from European Patent Office in application serial No. EP 16770624.1 dated Apr. 20, 2018, 3 pages.
International Preliminary Report dated Mar. 20, 2018, for corresponding application PCT/US2016/051670, 8 pages.
First Examination Report in European application No. 14721664.2 dated Jan. 15, 2018, 5 pages.
First Examination Report in European application No. 16150076.4 dated Jan. 12, 2018, 6 pages.
Sigrist et al., Ultrasound Elastography: Review of Techniques and Clinical Applications, Theranostics, (2017), 7 (5), pp. 1303-1329.
Spies et al., The UFS-QOL, a new disease-specific symptom and health-related quality of life questionnaire for leiomyomata, Obstet Gynecol, (2002), 99 (2), pp. 290-300.
Stewart et al., Uterine fibroids, Nat Rev Dis Primers, (2016), 2, 16043, 18 pages.
Stewart et al., Relative overexpression of collagen type I and collagen type III messenger ribonucleic acids by uterine leiomyomas during the proliferative phase of the menstrual cycle, J Clin Endocrinol Metab, (1994), 79 (3), pp. 900-906.
Sunder et al., Controlled Synthesis of Hyperbranched Polyglycerols by Ring-Opening Multibranching Polymerization, Macromolecules, (1999), 32 (13), pp. 4240-4246.
Takamoto et al., Cell death and proliferation and its relation to collagen degradation in uterine involution of rat, Connect Tissue Res, (1998), 37 (3-4), pp. 163-175.
Toyoshima et al., Collagen-binding domain of a Clostridium histolyticum collagenase exhibits a broad substrate spectrum both in vitro and in vivo, Connect Tissue Res, (2001), 42 (4), pp. 281-290.
Trueb et al., Characterization of the precursor form of type VI collagen, J Biol Chem, (1984), 259 (13), pp. 8597-8604.
Tsibris et al., Insights from gene arrays on the development and growth regulation of uterine leiomyomata, Fertil Steril, (2002), 78 (1), pp. 114-121.
Uhler et al., Regulation of genome organization and gene expression by nuclear mechanotransduction, Nat Rev Mal Cell Biol, (2017), 18 (12), pp. 717-727.
Walocha et al., Vascular system of intramural leiomyomata revealed by corrosion casting and scanning electron microscopy, Hum Reprod, (2003), 18 (5), pp. 1088-1093.
Wang et al., A novel selective progesterone receptor modulator asoprisnil (J867) down-regulates the expression of EGF, IGF-I, TGFbeta3 and their receptors in cultured uterine leiomyoma cells, Hum Reprod, (2006), 21 (7), pp. 1869-1877.
Wei et al., Spatial differences in biologic activity of large uterine leiomyomata, Fertil Steril, (2006), 85 (1), pp. 179-187.
Weston et al., Fibroids display an anti-angiogenic gene expression profile when compared with adjacent myometrium, Mol Hum Reprod, (2003), 9 (9), pp. 541-549.

(56) References Cited

OTHER PUBLICATIONS

Wu et al., Selective estrogen receptor modulators (SERMs) for uterine leiomyomas, Cochrane Database Syst Rev, (2007), (4), CD005287.

Wu et al., Versican protects cells from oxidative stress-induced apoptosis, Matrix Biol, (2005), 24 (1), pp. 3-13.

Xu et al., Progesterone receptor modulator CDB-2914 down-regulates proliferative cell nuclear antigen and Bcl-2 protein expression and up-regulates caspase-3 and poly(adenosine 5'-diphosphate-ribose) polymerase expression in cultured human uterine leiomyoma cells, J Clin Endocrinol Metab, (2005), 90 (2), pp. 953-961.

Yatsenko et al., Highly heterogeneous genomic landscape of uterine leiomyomas by whole exome sequencing and genome-wide arrays, Fertil Steril, (2017), 107 (2), pp. 457-466.

Yu et al., Collagen changes in rat cervix in pregnancy—polarized light microscopic and electron microscopic studies, Proc Soc Exp Biol Med, (1995), 209 (4), pp. 360-368.

Zhao et al., Increased expression of latent TGF-beta binding protein-1 and fibrillin-1 in human uterine leiomyomata, Mol Hum Reprod, (2007), 13 (5), pp. 343-349.

Breech et al., Leiomyomata uteri and myomectomy, Telinde's Operative Gynecology, Philadelphia: Lippincott, Williams and Wilkins, (2003), 9th ed, pp. 753-799.

Feng et al., Thrombospondin-1 in an early uterine fibroid development model, Matrix Biology, (2008), 27 (S1), pp. 50.

Sosic, A., et al., "Vascularity of Uterine Myomas: Assessment by Color and Pulsed Doppler Ultrasound," International Journal of Gynecology & Obstetrics, 1996; 54: 245-250.

Barrett, C., "Molecular Characterization of Leiomyoma," Presented at: The second National Institutes of Health International Congress on advances in uterine leiomyoma research: conference summary and future recommendations, Fertility and Sterility, 2006, 86(4), 7 pages.

Taylor, D.K., "The Hyperbranched Polyglycerol Platform: Approaching the ideal-drug delivery system." Proceedings of Abstracts for Duke University Research Day, May 6, 2009, Duke University, 1 page.

Cramer, S. F. and Patel, A., "The frequency of uterine leiomyomas," Am J Clin Pathol., 1990; 94(4):435-438.

D'Angelo, E., et al., "Uterine Smooth Muscles Tumors," In: Mutter GL, Prat J, editors. Pathology of the Female Reproductive Tract. 3rd ed Edinburgh: Churchill Livingstone/Elsevier; 2014, pp. 402-424.

Feng, L., et al., "Biochemical Pathways and Myometrial Cell Differentiation Leading to Nodule Formation Containing Collagen and Fibronectin," Curr Protein Pept Sci., 2017, 18:155-166.

Feng, L., et al., "Pattern of Collagen Types in Uterine Fibroids," Reproductive Sciences (2010), 17(3):711, 1 page.

Heskins, M., and Guillet, J. E., Solution Properties of Poly(N-isopropylacrylamide), Journal of Macromolecular Science-Chemistry, (1968), 2:8, pp. 1441-1455.

Kao, K. Y. T., et al., "Polymorphism in Human Uterine Collagen," Connect Tissue Research, 1977, 5(2):127-129.

Norian, J. M., et al., "Testing of the Wound Healing Hypothesis for Leiomyomas: Evaluation of Versican Variants," Reproductive Sciences (2007), vol. 14:1, 1 page.

Ibraheem, B., et al., "Towards water-soluble star copolymer-drug conjugates," Proc. of 58th Conf. of South East Regional Amer. Chem. Society, Nov. 1-4, 2006, Augusta, GA, Abstract, 1 page.

Dictionary of Chemical Engineering. Viscosity. Oxford University Press (publisher). First edition. Copyright 2014. Oxford University Press. Ed.: Carl Schaschke. Editorial Offices, Oxford, UK. p. 403.

Kikuchi, T. et al. 1998. Instr-articular injection of collagenase induces experimental osteoarthritis in mature rabbits. Osteoarthritis and Cartilage 6:177-186. Specif. pp. 177, 178.

Brandhorst, H. et al. 2008. The ratio between collagenase class I and class II influences the efficient islet release from the rat pancreas. Transplantation 85: 456-46. specif. pp. 456, 457.

Reconsideration Report before Appeal issued for Japanese application No. 2016-503099 dated Aug. 20, 2019, 7 pages.

Reconsideration Report before Appeal issued for Japanese application No. 2015-245310 dated Aug. 20, 2019, 5 pages.

Gilpin, D., et al., "Injectable collagenase clostridium histolyticum: A new nonsurgical treatment for Dupuytren's disease," J Hand Surg Am 2010, 35(12).

Iwahashi, M., et al., "Immunohistochemical analysis of collagen expression in uterine leiomyomata during the menstrual cycle," Experimental and Therapeutic Medicine 2011, 2:287-290.

Pharmaceuticals and Medical Devices Agency (PMDA) website, Jun. 2015, http://www.info.pmda.go.jp/downfiles/ph/PDF/100898_2900401D1020_1_01.pdf, 2 pages.

Dhaneshwar, S., et al., "Dextran: A promising macromolecular drug carrier," Indian Journal of Pharmaceutical Sciences, Nov.-Dec. 2006, 705-714.

Examination Report in Canadian patent application No. 2907255 dated Sep. 3, 2019, 6 pages.

Xiaflex, https://www.rxlist.com/xiaflex-drug.htm#description, Jul. 13, 2018, 3 pages.

Office Action issued in Japanese patent apln. 2016-503099 dated Mar. 18, 2020, with English translation, 24 pages.

Office Action issued in Japanese patent apln. 2015-245310 dated Mar. 24, 2020, with English translation, 45 pages.

Australian Examination Report No. 1 for AU 2015206597 dated May 23, 2019, 6 pages.

\* cited by examiner

Figure 2B
A  Ultrasound    B  Gross
1 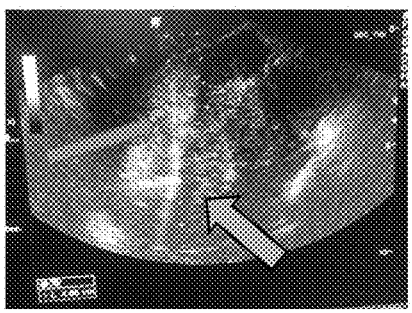 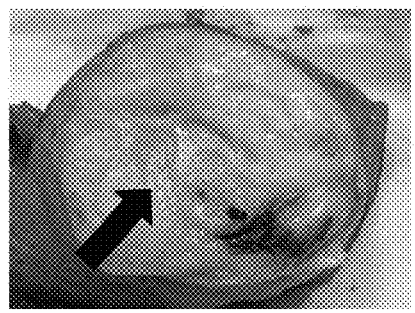
2 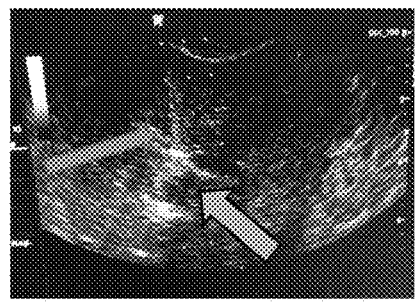 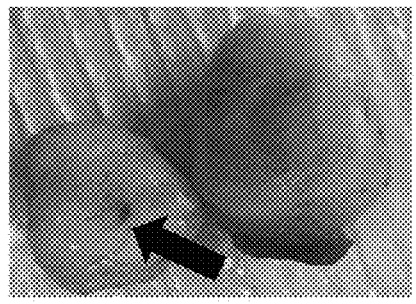
3 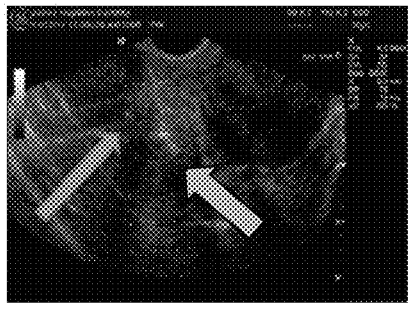 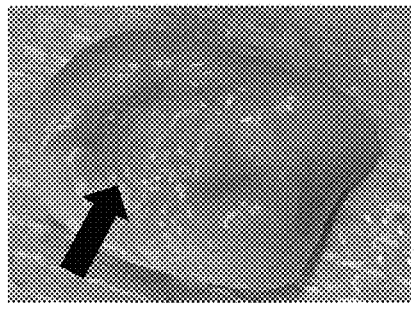
4 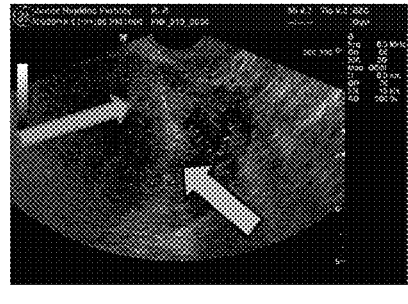 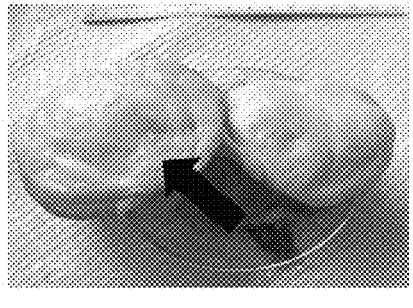

Figure 4
1a
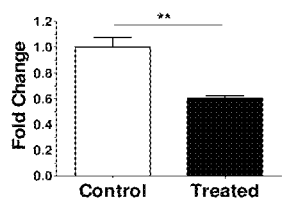
1 b
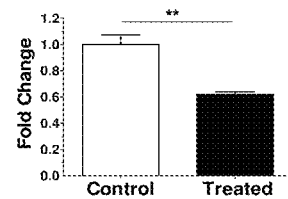
1c
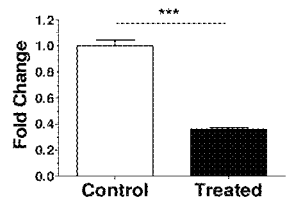
2.1 a
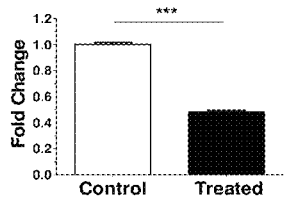
2.1b
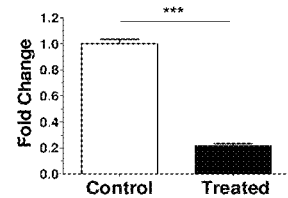
2.1 c
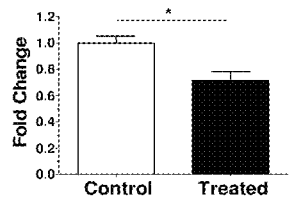
2.2 a
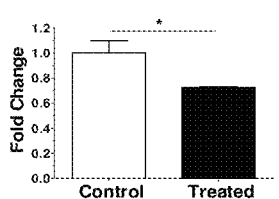
2.2 b
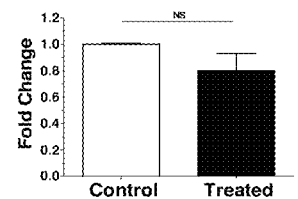
2.2 c
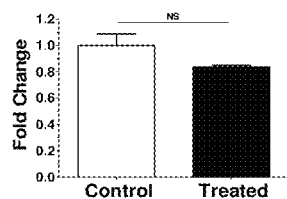
2.3 a
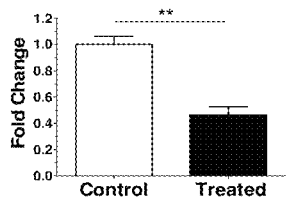
2.3 b
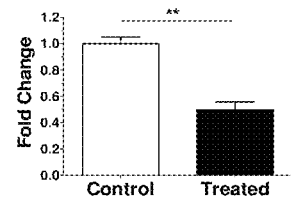
2.3 c
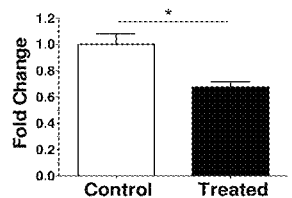

Figure 8
CONTROL FIBROID 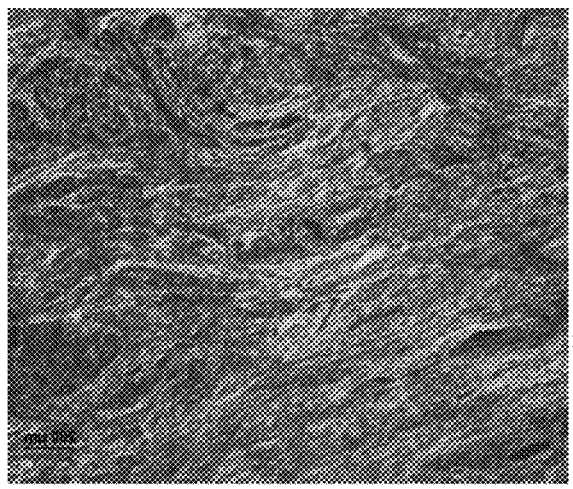 TREATED FIBROID 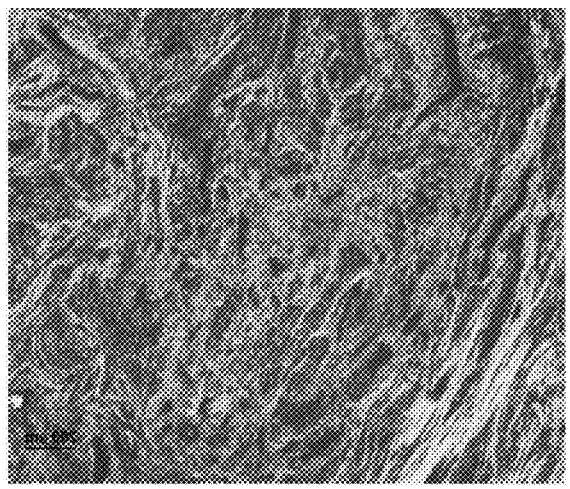
A B

Figure 10: Summary of Baseline Characteristics of Study Subjects

| EN3835 Study Subjects | | | | | |
|---|---|---|---|---|---|
| Study Group | Saline Only | Group 1 | Group 2 Dose 1 | Group 2 Dose 2 | Group 2 Dose 3 |
| Age, years, mean (SD) | 46.0 (2.6) | 44.0 (1.0) | 46.0 (3.0) | 42.0 (1.7) | 45.3 (2.9) |
| Female, n, (Black: White) | 3 (1:2) | 3 (2:1) | 3 (2:1) | 3 (2:1) | 3 (2:1) |
| Weight, kg. mean(SD) | 70.2 (4.8) | 105.8 (4.1) | 90.3 (20.4) | 59.7 (8.6) | 90.5 (21.6) |
| Height, m, mean (SD) | 1.6 (0.0) | 1.7 (0.0) | 1.6 (0.1) | 1.6 (0.1) | 1.7 (0.1) |
| Body Mass Index, kg/m$^2$ | 27 (2.5) | 34.8 (1.0) | 33.8 (3.9) | 24.7 (4.1) | 32.1 (5.4) |

*Legend:* Values are presented as mean with standard deviation (SD).

Figure 11

| Group | Intensity Density⁺ of Collagen Ratio | P-value* | [95% Conf. Interval] | | p-value for interaction |
|---|---|---|---|---|---|
| G1 | 0.514 | <0.001 | 0.383 | 0.690 | - |
| G2/D1 | 0.419 | 0.004 | 0.233 | 0.756 | 0.545 |
| G2/D2 | 0.784 | <0.001 | 0.732 | 0.840 | 0.006 |
| G2/D3 | 0.533 | <0.001 | 0.435 | 0.653 | 0.839 |

Figure 12

|  | All Subjects (n = 15) n (%) |
|---|---|
| Treatment-Emergent AEs |  |
| Mild* | 30 ( 68.18)** |
| Moderate | 14 (31.18) |
| Severe | 0 |
| Drug-related | 0 |
| Serious adverse events | 0 |
| Drug-related serious adverse events | 0 |

Figure 13

| Group | Subject ID | Total number of fibroids | Largest diameter of injected fibroid(in cm) | Study drug dosage (mg) |
|---|---|---|---|---|
| Saline Only Group | FIB_002_6589 | 3 major | 3.2, 4.6 | 0 |
| | FIB_003_0594 | 10, 5 major, 5 minor | 3.45 | 0 |
| | FIB_004_9539 | 1 major, 4 minor | 6.85, 4.34 | 0 |
| Group 1 | FIB_006_1474 | 5 major+ multiple minor | 4.01 | 1.16 |
| | FIB_007_4898 | 5 major+ multiple minor | 5.2 | 1.16 |
| | FIB_009_3785 | 5 major | 4.2 | 1.16 |
| Group 2 Dose 1 | FIB_010_6378 | 2 major, 4 minor | 8 | 1.68 |
| | FIB_011_2090 | 3 major | 3.1 | 0.71 |
| | FIB_012_0836 | 5 major | 4.5 | 1.68 |
| Group 2 Dose 2 | FIB_013_8676 | >15, 5 major, multiple minor | 4.73 | 3.35 |
| | FIB_014_9766 | 5, 2 major, 2 minor | 3.34 | 1.41 |
| | FIB_015_3113 | 3 major, 1 minor | 4.15 | 3.35 |
| Group 2 Dose 3 | FIB_017_5270 | 4 major, multiple minor | 4.41 | 5.02 |
| | FIB_018_9223 | 2 major | 3.02 | 2.83 |
| | FIB_019_3634 | 2 major | 6.16 | 5.02 |

Figure 15:

Characteristics of examined fibroid tissue slices.

| Fibroid Slice | Diameter [cm] | Appearance | Collagen [%] | Stiffness [Pa] | Stiffness CV [%] |
|---|---|---|---|---|---|
| 13–1 | 3.7 | Whorled Nodular | 47 | 3028 | 33.0 |
| 10–2 | 3.0 | Could not be classified | 56 | 3716 | 34.9 |
| 14–2 | 5.7 | Trabecular Nodular | 49 | 4228 | 1.6 |
| 15–2 | 8.5 | Trabecular | 43 | 5304 | 18.7 |
| 9–2 | 5.0 | Whorled | 48 | 5569 | 2.4 |
| 9–3 | 11.0 | Whorled Trabecular Nodular | 55 | 6877 | 40.5 |
| 9–5 | 7.0 | Whorled | 65 | 6994 | 42.9 |
| 16–1 | 4.5 | Nodular | 45 | 7057 | 22.1 |
| 15–1 | 6.5 | Trabecular | 53 | 7276 | 8.7 |
| 17–1 | 6.0 | Whorled Trabecular | 49 | 7325 | 13.9 |
| 12–1 | 8.0 | Trabecular | 71 | 7348 | 12.8 |
| 16–4 | 7.5 | Nodular | 48 | 8570 | 20.5 |
| 16–2 | 4.0 | Nodular | 64 | 9792 | 42.0 |
| 17–3 | 4.5 | Trabecular | 37 | 10035 | 29.0 |
| 14–1 | 5.4 | Whorled | 67 | 10210 | 27.4 |
| 16–3 | 5.5 | Could not be classified | 63 | 10251 | 14.1 |
| 14–4 | 8.5 | Whorled Trabecular Nodular | 45 | 11126 | 25.9 |
| 14–3 | 6.0 | Whorled Trabecular Nodular | 77 | 11286 | 29.9 |
| 17–2 | 3.8 | Nodular | 49 | 14180 | 19.4 |

Figure 19

Proportion of collagen types in fibroids.

| Fibroid | Fibroid Size [cm] | Sample* | Collagen Types [%] (average ± standard deviation) | | | Ratio Type I/III |
|---|---|---|---|---|---|---|
| | | | Type I | Type III | Type V | |
| 5 | 4 x 4 | Center | 73 ± 16 | 24 ± 6 | 2.0 ± 0.3 | 3.0:1 |
| | | Edge | 65 ± 5 | 32 ± 2 | 2.1 ± 0.2 | 2.0:1 |
| 8 | 8 x 8 | Center | 37 ± 1 | 55 ± 1 | 7.4 ± 0.6 | 0.7:1 |
| | | Edge | 42 ± 7 | 49 ± 6 | 7.0 ± 1.0 | 0.9:1 |
| 395 | 5.5 x 4 | Center | 63 ± 17 | 32 ± 6 | 4.0 ± 0.9 | 2.0:1 |
| | | Edge | 68 ± 13 | 28 ± 4 | 2.7 ± 0.6 | 2.4:1 |
| 401 | 9.7 x 2.8 | Center | 74 ± 13 | 22 ± 4 | 2.8 ± 0.6 | 3.4:1 |
| | | Edge | 68 ± 3 | 29 ± 1 | 2.6 ± 0.2 | 2.3:1 |
| 411 | 12.5 x 10.5 | Center | 58 ± 19 | 38 ± 8 | 3.1 ± 0.8 | 1.5:1 |
| | | Edge | 72 ± 19 | 26 ± 5 | 2.2 ± 0.5 | 2.8:1 |

Figure 20

This excel file "Suppl data.xlsx" contains the rheometry data (stiffness as measured by complex shear modulus) from all 44 individual punches. These are the underlying data for averages, SDs and CVs presented in the Results Section and in Table 1 and Figure 3. All other underlying data of biological replicates are presented within the manuscript.

| Subject | Fibroid Slice | Punch | Complex Shear Modulus(G*) Pa | average | STDEV() | rounded to | stdev/mean CV [%] | average within subject | STDEV within subject | rounded to | CV [%] within subject |
|---|---|---|---|---|---|---|---|---|---|---|---|
| 9 | 9-2 | 1 | 5662 | 5569 | 132 | | 2.4 | 6480 | 792 | 800 | 12.2 |
| 9 | 9-2 | 2 | 5475 | | | | | | | | |
| 9 | 9-3 | 1 | 9924 | 6877 | 2786 | | 40.5 | | | | |
| 9 | 9-3 | 2 | 4460 | | | | | | | | |
| 9 | 9-3 | 3 | 6248 | | | | | | | | |
| 9 | 9-5 | 1 | 7103 | 6994 | 2997 | | 42.9 | | | | |
| 9 | 9-5 | 2 | 3944 | | | | | | | | |
| 9 | 9-5 | 3 | 9936 | | | | | | | | |
| 10 | 10-2 | 1 | 3027 | 3716 | 1298 | | 34.9 | | | | |
| 10 | 10-2 | 2 | 2908 | | | | | | | | |
| 10 | 10-2 | 3 | 5214 | | | | | | | | |
| 12 | 12-1 | 1 | 8198 | 7348 | 943 | | 12.8 | | | | |
| 12 | 12-1 | 2 | 7511 | | | | | | | | |
| 12 | 12-1 | 3 | 6334 | | | | | | | | |
| 13 | 13-1 | 1 | 2027 | 3028 | 998 | | 33.0 | | | | |
| 13 | 13-1 | 2 | 3034 | | | | | | | | |
| 13 | 13-1 | 3 | 4023 | | | | | | | | |
| 14 | 14-1 | 1 | 12190 | 10210 | 2801 | | 27.4 | 9212 | 3356 | 3400 | 36.4 |
| 14 | 14-1 | 2 | 8229 | | | | | | | | |
| 14 | 14-2 | 1 | 4179 | 4228 | 69 | 70 | 1.6 | | | | |
| 14 | 14-2 | 2 | 4277 | | | | | | | | |
| 14 | 14-3 | 1 | 8902 | 11286 | 3371 | | 29.9 | | | | |
| 14 | 14-3 | 2 | 13670 | | | | | | | | |
| 14 | 14-4 | 1 | 9091 | 11126 | 2877 | | 25.9 | | | | |
| 14 | 14-4 | 2 | 13160 | | | | | | | | |
| 15 | 15-1 | 1 | 6828 | 7276 | 633 | | 8.7 | 6290 | 1394 | 1400 | 22.2 |
| 15 | 15-1 | 2 | 7723 | | | | | | | | |
| 15 | 15-2 | 1 | 4601 | 5304 | 993 | | 18.7 | | | | |
| 15 | 15-2 | 2 | 6006 | | | | | | | | |
| 16 | 16-1 | 1 | 8160 | 7057 | 1561 | | 22.1 | 8917 | 1429 | 1400 | 16.0 |
| 16 | 16-1 | 2 | 5953 | | | | | | | | |
| 16 | 16-2 | 1 | 12700 | 9792 | 4113 | 4110 | 42.0 | | | | |
| 16 | 16-2 | 2 | 6883 | | | | | | | | |
| 16 | 16-3 | 1 | 9232 | 10251 | 1441 | | 14.1 | | | | |
| 16 | 16-3 | 2 | 11270 | | | | | | | | |
| 16 | 16-4 | 1 | 7329 | 8570 | 1755 | | 20.5 | | | | |
| 16 | 16-4 | 2 | 9811 | | | | | | | | |
| 17 | 17-1 | 1 | 7047 | 7325 | 1020 | | 13.9 | 10513 | 3452 | 3500 | 32.8 |
| 17 | 17-1 | 2 | 8455 | | | | | | | | |
| 17 | 17-1 | 3 | 6473 | | | | | | | | |
| 17 | 17-2 | 1 | 12230 | 14180 | 2758 | | 19.4 | | | | |
| 17 | 17-2 | 2 | 16130 | | | | | | | | |
| 17 | 17-3 | 1 | 7980 | 10035 | 2906 | | 29.0 | | | | |
| 17 | 17-3 | 2 | 12090 | | | | | | | | |
| | n=19 | n=44 | range of all punches: 2027-16130 | range of all means: 3028-14180 | range of STDEV: 69-4113 | | range of CV's: 1.6-42.9% | | range of SD within subject: 800-3500 | | range of CV's within subject: 12.2-36.4% |
| | | | median | | median | | median | | | | |
| | | | 7216 | | 7325 | | 22.1 | | | | |
| | | | mean | | mean | | mean | | | | |
| | | | 7628 | | 7904 | | 23.1 | | | | |
| | | | STDEV | | STDEV() | | | | | | |
| | | | 3254 | | 2899 | | | | | | |
| | | | CV | | CV [%] | | | | | | |
| | | | 0.427 | | 36.7 | | | | | | |

Figure 23

| Group | Intensity Density of Collagen Ratio (treated / control) | P-value* | [95% Conf. Interval] | | p-value for interaction |
|---|---|---|---|---|---|
| G1 | 0.514 | <0.001 | 0.383 | 0.690 | -- |
| G2/D1 | 0.419 | 0.004 | 0.233 | 0.756 | 0.545 |
| G2/D2 | 0.784 | <0.001 | 0.732 | 0.840 | 0.006 |
| G2/D3 | 0.533 | <0.001 | 0.435 | 0.653 | 0.839 |

Figure 28

| Group | Subject ID | Number of fibroids | Largest Diameter of Injected fibroid (in cm) | McGill Pain Scale | | |
|---|---|---|---|---|---|---|
| | | | | Baseline | 2 Weeks Post hysterectomy | |
| | FIB_002_8989 | 3 major | 3.2, 4.6 | 12 | 25 | |
| | FIB_003_0594 | 10, 5 major, 5 minor | 3.45 | 16 | 7 | |
| Saline Only Group | FIB_004_9539 | 1 major, 4 minor | 6.85, 4.34 | 37 | 8 | |
| | | | | Baseline | 24-48 hrs Post Injection | |
| | FIB_006_1474 | 5 major+ multiple minor | 4.01 | 24 | 14 | |
| Group 1 | FIB_007_4898 | 5 major+ multiple minor | 5.2 | 16 | 16 | |
| | FIB_009_3785 | 5 major | 4.2 | 28 | 21 | |
| | | | | Baseline | 4-8 Days Post Injection | 60-90 Days Post Injection |
| | FIB_010_6378 | 2 major, 4 minor | 8 | 3 | 10 | 2 |
| Group 2 Dose 1 | FIB_011_3030 | 3 major | 3.1 | 49 | 19 | 10 |
| | FIB_012_0836 | 5 major | 4.5 | 10 | 8 | 6 |
| | FIB_013_8676 | >15, 5 major, multiple minor | 4.73 | 65 | 11 | 0 |
| Group 2 Dose 2 | FIB_014_9766 | 5, 2 major, 2 minor | 3.34 | 0 | 0 | 0 |
| | FIB_015_3113 | 3 major, 1 minor | 4.15 | 25 | 4 | 22 |
| | FIB_017_5270 | 4 major, multiple minor | 4.41 | 0 | 0 | 0 |
| Group 2 Dose 3 | FIB_018_9333 | 2 major | 3.02 | 17 | 6 | 6 |
| | FIB_019_3634 | 2 major | 6.16 | 41 | 25 | 29 |

Figure 31

The cDNA deduced primary sequence of Collagenase ABC I

```
   1 mkknilkilm dsyskeskiq tvrrvtsvsl lavyltmnts slvlakpien tndtsiknve
  61 klrnapneen skkvedsknd kvehvkniee akveqvapev kskstlrsas iantnsekyd
 121 feylnglsyt eltnliknik wnqinglfny stgsqkffgd knrvqaiina lqesgrtyta
 181 ndmkgietft evlragfylg yyndglsyln drnfqdkcip amiaiqknpn fklgtavqde
 241 vitslgklig nasanaevvn ncvpvlkqfr enlnqyapdy vkgtavneli kgiefdfsga
 301 ayekdvktmp wygkidpfin elkalglygn itsatewasd vgiyylskfg lystnrndiv
 361 qslekavdmy kygkiafvam eritwdydgi gsngkkvchd kflddaekhy lpktytfdng
 421 tfiiragdkv seekikrlyw asrevksqfh rvvgndkale vgnaddvltm kifnspeeyk
 481 fntningvst dngglyiepr gtfytyertp qqsifsleel frheythylq arylvdglwg
 541 qgpfyeknrl twfdegtaef fagstrtsgv lprksilgyl akdkvdhrys lkktlnsgyd
 601 dsdwmfynyg favahylyek dmptfikmnk ailntdvksy deiikklsdd anknteyqnh
 661 iqeladkyqg agiplvsddy lkdhgykkas evyseiskaa sltntsvtae ksqyfntftl
 721 rgtytgetsk gefkdwdems kkldgtlesl aknswsgykt ltayftnyrv tsdnkvqydv
 781 vfhgvltdna disnnkapia kvtgpstgav grniefsgkd skdedgkivs ydwdfgdgat
 841 srgknsvhay kkagtynvtl kvtddkgata tesftieikn edtttpitke mepnddikea
 901 ngpivegvtv kgdlngsdda dtfyfdvked gdvtielpys gssnftwlvy kegddqnhia
 961 sgidknnskv gtfkstkgrh yvfiykhdsa snisyslnik glgneklkek enndssdkat
1021 vipnfnttmq gsllgddsrd yysfevkeeg evnieldkkd efgvtwtlhp esnindrity
1081 gqvdgnkvsn kvklrpgkyy llvykysgsg nyelrvnk
```

The cDNA deduced primary sequence of Collagenase ABC II

```
   1 mkrkclskrl mlaitmatif tvnstlpiya avdknnataa vqneskrytv sylktlnyyd
  61 lvdllvktei enlpdlfqys sdakefygnk trmsfimdei grrapqytei dhkqiptlve
 121 vvragfylgf hnkelneink rsfkervips ilaiqknpnf klgtevqdki vsatgllagn
 181 etappevvnn ftpilqdcik nidryalddl kskalfnvla aptyditeyl ratkekpent
 241 pwygkidgfi nelkklalyg kindnnswii dngiyhiapl gklhsnnkig ietltevmkv
 301 ypylsmqhlq sadqikrhyd skdaegnkip ldkfkkegke kycpktytfd dgkviikaga
 361 rveeekvkrl ywaskevnsq ffrvygidkp leegnpddil tmviynspee yklnsvlygy
 421 dtnnggmyie pegtfftyer eaqestytle elfrheythy lqgryavpgq wgrtklydnd
 481 rltwyeegga elfagstrts gilprksivs nihnttrnnr yklsdtvhsk ygasfefyny
 541 acmfmdymyn kdmgilnkln dlaknndvdg ydnyirdlss nyalndkyqd hmqeridnye
 601 nltvpfvadd ylvrhayknp neiyseisev aklkdaksev kksqyfstft lrgsytggas
 661 kgkledqkam nkfiddslkk ldtyswsgyk tltayftnyk vdssnrvtyd vvfhgylpne
 721 gdsknslpyg kingtykgte kekikfsseg sfdpdgkivs yewdfgdgnk sneenpehsy
 781 dkvgtytvkl kvtddkgess vstttaeikd lsenklpviy mhvpksgaln qkvvfygkgt
 841 ydpdgsiagy qwdfgdgsdf sseqnpshvy tkkgeytvtl rvmdssgqms ektmkikitd
 901 pvypigteke pnnsketasg pivpgipvsg tientsdqdy fyfdvitpge vkidinklgy
 961 ggatwvvyde nnnavsyatd dgqnlsgkfk adkpgryyih lymfngsymp yriniegsvg
1021 r
```

Figure 34

Dosage of injected collagenase in fibroids by study group

| Group of Subject | Sample | Dose mg | Dose mg/cm$^3$ |
|---|---|---|---|
| G2 D2 | FIB 014 | 1.41 | 0.42 |
| G2 D2 | FIB 013 | 3.35 | 0.71 |
| G2 D2 | FIB 015 | 3.35 | 0.81 |
| G2 D3 | FIB 018 | 2.83 | 0.94 |
| G2 D3 | FIB 017 | 5.028 | 1.14 |
| G2 D3 | FIB 019 | 5.028 | 1.21 |

G=Group; D=Dose.

TREATMENT OF UTERINE FIBROIDS USING PURIFIED COLLAGENASE

CROSS-REFERENCE TO RELATED APPLICATION

This application claims priority to U.S. Provisional Application Ser. No. 62/915,360, filed on Oct. 15, 2019, which is hereby incorporated by reference in its entirety.

The instant application contains a Sequence Listing which has been submitted electronically via EFS-Web in ASCII format and is hereby incorporated by reference in its entirety. Said ASCII copy, created on Jan. 5, 2021, is named 3762-143US2_ST25 and is 18,889 bytes in size.

FIELD OF THE INVENTION

The present invention relates to methods and products for medical treatment designed to reduce, shrink change the viscoelastic properties of, soften or eliminate unwanted tissue such as uterine fibroid tissue, and to decrease the symptoms of uterine fibroids, including menorrhagia, metrorrhagia, anemia, pelvic pain and pressure, dyspareunia, and infertility.

BACKGROUND OF THE INVENTION

Uterine fibroid tumors (also referred to as "uterine fibroids" or "leiomyomas") are non-cancerous tumors of the uterine wall that occur in 20 to 50% of women, and have an astonishingly high accumulative incidence. Current studies demonstrate that by age 50, 70-80% of women have developed uterine fibroids, with higher incidence in African-American women, who commonly develop fibroids earlier than other racial groups. A significant number of those with uterine fibroids suffer from debilitating pelvic pain, heavy and prolonged bleeding (which may lead to anemia and iron deficiency), bowel and bladder dysfunction and infertility. Uterine fibroids also cause symptoms such as low back pain, urinary frequency and urgency, pain during intercourse (dyspareunia), can cause pre-term labor, and have a negative impact on fertility (due to cavity distension, and alteration of endometrial receptivity and sexual function). They are associated with high morbidity from uterine bleeding and pain along with health care costs estimated to be between $2.1 and $34.4 billion annually in the United States alone. Therefore, uterine fibroids have a significant impact on the health and well-being of reproductive age women and on the economy. After menopause, generally, fibroids shrink and only rarely cause problematic symptoms.

The etiology of this disease remains unknown, therefore there are no methods of preventing uterine fibroids. Several treatments are available, but hysterectomy is the only treatment which can permanently eliminate fibroids. The majority of the hysterectomies performed in the United States each year are due to uterine fibroids. It is obvious, but rarely stated in the literature, that hysterectomies lead to irrevocable loss of fertility. This invasive surgery also has a high cost, financially, socially and otherwise. It is associated with lengthy recovery times, potential for sometimes severe post-operative complications, and physical discomfort. Thus, this solution is far from ideal.

Other surgical methods such as myomectomy (surgical removal of the fibroid tissue leaving the remainder of the uterus intact) is commonly used, but may not be suitable in cases where the fibroids are too large or too numerous to leave enough normal tissue behind. Further, the fibroids often recur—recurrence rates for fibroids treated with myomectomy are estimated at 50-60% within 5 years. In addition, about three-quarters of myomectomy surgeries are open surgeries involving an abdominal incision. Therefore, this method also is associated with complications, discomfort, long recovery, and potentially loss of fertility as well. Myolysis and cryomyolysis, in which uterine fibroids are burned or frozen via laparoscopic surgery, can be used to cause the fibroids to shrink and die over time. However, multiple punctures of the fibroids are needed to treat the entire tumor, and the treatment may cause adhesions postsurgery. MRI guided focused ultrasound also is used in the treatment of uterine fibroids, but this procedure is very expensive, and does not permanently eliminate the fibroids. Uterine artery embolization, during which a catheter is inserted into a femoral artery and guided to a uterine fibroid artery for injection of small particles into the fibroid artery, blocks the supply of blood, resulting in death of the fibroid tissue. Although this procedure is less invasive than traditional surgery, post-surgical pain is a frequent problem. In addition, this therapy, like hysterectomy, is considered a standard treatment for women with no desire for future fertility. Alternatively, MRgFUS provides noninvasive fibroid-specific therapy utilizing high-intensity ultrasonography through the abdominal wall to cause coagulative necrosis in specific fibroids. Guidance and thermal monitoring is provided by dynamic real-time magnetic resonance imaging. The surgical procedures to destroy uterine fibroids while preserving the uterus also have major drawbacks and often are not completely successful, due to re-growth of the fibroid tumors.

Non-surgical, pharmaceutical-based medical therapies are available. Fibroids often are treated by medications aimed at treating the symptoms rather than the fibroid tumors themselves. In the early stages, physicians employ a "wait-and-see" approach, with no treatment or symptomatic treatment until the condition impacts the ability of the patient to function in normal life. Most fibroids are not treated unless they are causing symptoms. However, even in the absence of hysterectomy, fibroids, particularly subserosal fibroids, also can lead to infertility.

The pharmacotherapies which are aimed at shrinking fibroid tumors or preventing increase in size have been disappointing and often have significant side effects. Drugs have been studied and sometimes are effective at shrinking uterine fibroids, but many of these non-surgical therapies have been associated with systemic side effects and therefore have not been approved for clinical use. For example, selective progesterone receptor modulators (SPRM) have not been approved by the FDA due to their effects on the endometrium. Only one drug has been approved for use to shrink uterine fibroids: leuprolide acetate. This drug is used as a short-term treatment which suppresses ovarian function (and therefore causes significant menopausal side effects), shrinking fibroids prior to surgery. Other medical therapies have been suggested in the recent past such as selective estrogen receptor modulators (SERM), but clinical trial results have been disappointing.

Current treatment options for uterine fibroids are inadequate. Hence, there is a continuing need in the art for alternative therapies for the treatment of uterine fibroids which are not open procedures and which preserve the patient's uterus. In particular, because treatment of uterine fibroids costs billions of health care dollars each year, and yet this condition remains a significant problem, there is a need for treatment methods that reduce or eliminate symptoms, provide relief without highly invasive procedures, and which preserve fertility.

SUMMARY OF THE INVENTION

The following brief summary is not intended to include all features and aspects of the present invention, nor does it imply that the invention must include all features and aspects discussed in this summary.

Embodiments of the invention are designed to provide the advantage of formulations, compositions and methods for treatment of uterine fibroids which do not require open surgical procedures and which preserve the patient's uterus. Another advantage of the present invention is that injectable or insertable formulations are provided, which display improved retention of agents within uterine fibroid tissue, thereby improving delivery efficiency, while at the same time minimizing adverse effects such as nonspecific damage and systemic effects. These formulations, compositions and methods include injectable, implantable or insertable formulations which contain one or more uterine fibroid treatment agents, preferably at least a purified collagenase in an amount effective to shrink or eliminate fibroids that are exposed to the formulation, and/or reduce the symptoms of the fibroid(s).

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

The application file contains at least one drawing executed in color. Copies of any patent or patent application publication from this application containing color drawing(s) will be provided by the Office upon request and payment of the necessary fee.

FIG. 2b. Representative images of the ultrasound guided study drug injection (Column A), gross hem i-section of the fibroid tissue (Column B) injected with various doses of collagenase GroupI, 1.16 mg (Row 1), and Group 2 Dose 1, (Row 2), Dose 2, (Row 3), & Dose 3, (Row 4) with 1.68, 3.35, and 5.028 mg as the maximum doses, respectively. The blue arrows mark the needle, grey arrows mark the study drug, and the black arrows mark the area of digestion by the study drug in the hemisected fibroid sample. The areas of digestion were visibly darkened and softened (black arrows, rows 1, 3, 4), and sometimes completely liquefied, as in the hole noted row 2 (black arrow).

FIG. 4. Quantification of collagen content. Masson's trichrome for specimens from all 12 study subjects injected with EN3835. Control and injected fibroids (n=12 each) were sectioned and stained with Masson's Trichrome. Collagen density (mean±SEM) was quantified in ImageJ using 9 grids with areas of approximately 500,000 pixels. Fold change represented on Y-Axis reduction in collagen between control (set at 1.0) and treated samples. Group 1, (1a, 1 b, 1c); Group 2 Dose 1, (2.1a, 2.1 b, 2.1 c); Group 2 Dose 2, (2.2a, 2.2b, 2.3c); Group 2 Dose 3, (2.3a, 2.3b. 2.3). *p<0.05, p<0.01 and *p-value<0.001 (unpaired T-test)

FIG. 8. Picrosirius stained Control (A), and Treated (B) fibroid tissue. Collagenase treated tissues were less dense, and collagen fibers were shorter than in control tissues, as shown on the right. These slides were viewed under polarized light to visualize birefringence of collagen fibers and the content was subjectively judged. (N=12, one representative image shown)

FIG. 10. Summary of baseline characteristics of study subjects. Values are presented as mean with standard deviation (SD).

FIG. 11. Changes in collagen content using a log linear mixed effects model for estimated ratio of intensity density of collagen by treatment and control group. G1=Group 1; G2/D1=Group 2 Dose 1; G2/D2=Group 2 Dose 2; G2/D3=Group 2 Dose 3. ±Intensity density is the sum of pixel values for collagen from ImageJ software analysis. *—indicates a statistically significant change in Collagen Intensity Density between treatment and control, p-value<0.001. ** indicates a statistically significant difference in change in Collagen Intensity Density between treatment and control for group2/D2 vs. group 1.

FIG. 12. Summary of treatment emergent adverse events (all subjects). *Only 4 mild treatment emergent adverse events were deemed possibly related to the study drug. **No medical intervention was needed to control the 4 possibly drug related treatment emergent adverse events.

FIG. 13. Fibroid size and study drug dosage. *Largest diameter >3 cm-major, minor <3 cm.

FIG. 15. Characteristics of examined fibroid tissue slices.

FIG. 19. Proportion of collagen types in fibroids. *Ten samples from five fibroids were studied. Samples were taken from edge and center of each fibroid.

FIG. 20. Rheometry data from all 44 individual tissue punches. This contains the rheometry data (stiffness as measured by complex shear modulus) from all 44 individual punches. These are the underlying data for averages, SDs and CVs presented in the Results Section and in FIGS. 15 and 17.

FIG. 23. Analysis of changes in collagen content by group (treated/control) using log linear model for estimated intensity-density of collagen. *Log linear model G1=Group 1; G2/D1=Group 2, Dose 1; G2/D2=Group 2, Dose 2; G2/D3=Group 2, Dose 3.

FIG. 28. Data on fibroids in each subject and McGill Pain Scale before and after (4-8 days and 60-90 days) injection.

FIG. 31. The cDNA deduced primary sequence of Collagenase ABC I (SEQ ID NO: 1) and ABC II (SEQ ID NO:2).

FIG. 34. Dosage of injected collagenase in fibroids by study group.

DETAILED DESCRIPTION OF THE INVENTION

Definitions

Figure 1:
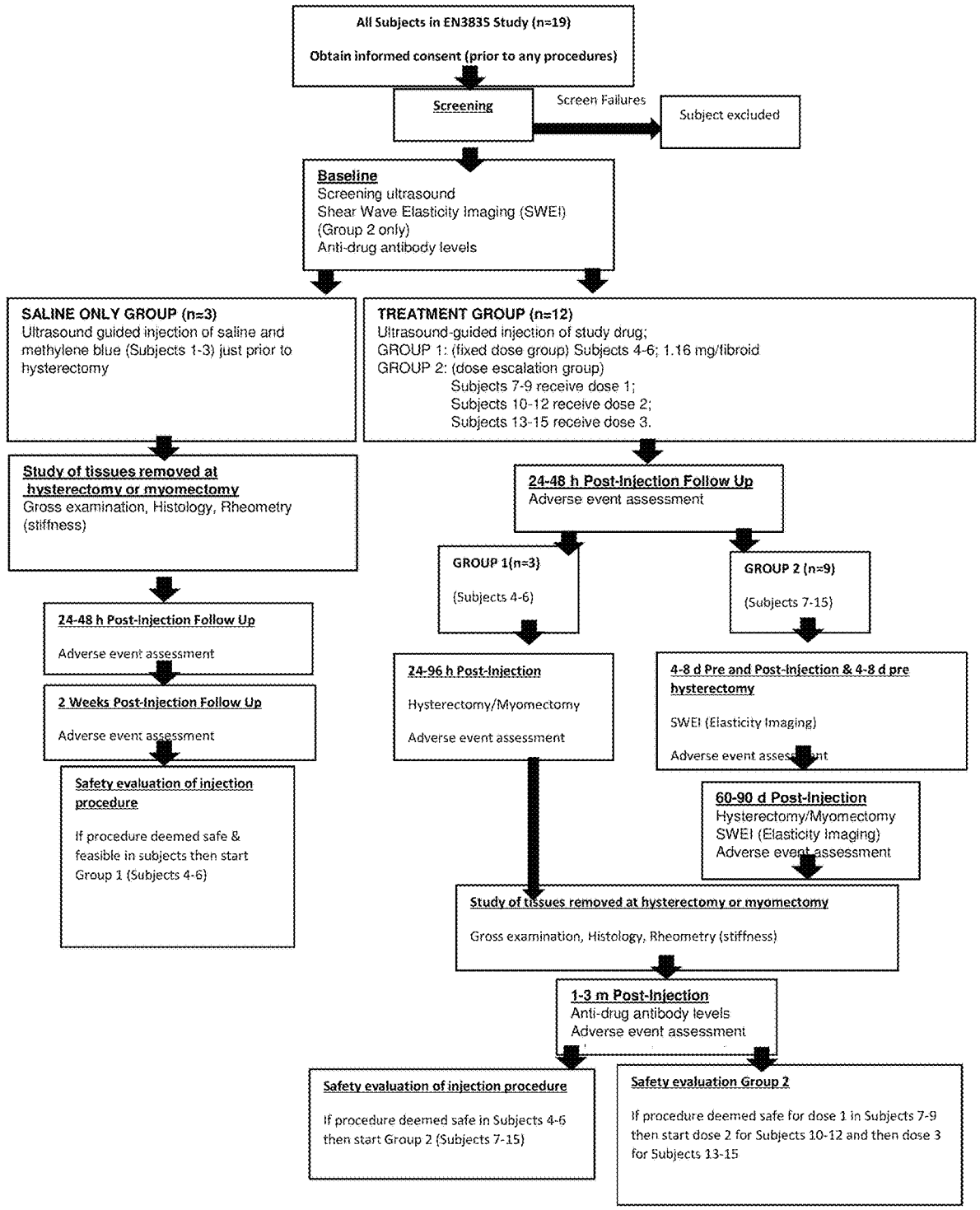
FIG. 1. Study Design. Detailed structure of the study activities. Standard clinical care was provided pre- and post-hysterectomy.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

"A" or "an" means herein one or more than one; at least one. Where the plural form is used herein, it generally includes the singular.

"Co-administer" with respect to this invention means to administer together two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning.

"Comprised of" is a synonym of "comprising" (see above).

"Decrease" and "decreasing" and similar terms are used herein generally to mean to lessen in amount or value or effect, as by comparison to another amount, value or effect. A decrease in a particular value or effect may include any significant percentage decrease, for example, at least 5%, at least 10%, at least 20%, at least 30%, at least 50%, at least 75% or at least 90%.

"Effective amount" generally means an amount which achieves the specific desired effects described in this application. For example, an effective amount is an amount sufficient to effectuate a beneficial or desired clinical result. Within the context of this invention generally the desired effect is a clinical improvement in symptoms present in a subject with uterine fibroids. In one embodiment, the symptom is pain the subject has as a result of the uterine fibroids. The effective amounts can be provided all at once in a single administration or in fractional amounts that provide the effective amount in several administrations. The precise determination of what would be considered an effective amount may be based on factors individual to each subject, including the size or number of fibroids, health of the patient, age, etc. One skilled in the art will be able to determine the effective amount based on these considerations. As used herein, "effective dose" means the same as "effective amount."

Accordingly, an "effective amount" of collagenase is an amount in which the clinical symptoms of the subject are improved. And an effective amount of collagenase would be that which is sufficient to reduce or alleviate symptoms of uterine fibroids, resulting in improved clinical outcome.

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result (in the present case, reduction of collagen content in one or more uterine fibroids, and associated reduction of symptoms associated therewith).

Use of the term "includes" is not intended to be limiting.

"Increase" or "increasing" means to induce a biological event entirely or to increase the degree of the event.

"May" as used herein the word "may" means the same as "optionally" and even where it is not stated, as used herein, "may" includes also that it "may not". That is, a statement that something may be, means as well that it also may not be. That is, as used herein, "may" includes "may not", explicitly, and applicant reserves the right to claim subject matter accordance therewith. For instance, as used herein, the statement that collagenase may be administered with other agents, also means that collagenase may be administered without any other agents.

"Optionally" as used herein means much the same as "may". The statement that X optionally includes A as used herein includes both X includes A and X does not include A.

"Pharmaceutically-acceptable carrier" is any pharmaceutically-acceptable medium for the collagenase used in the present invention. Such a medium may retain isotonicity, pH, and the like. It is compatible with administration to a subject and can be used, therefore, for treatment.

The term "reduce" as used herein means to prevent as well as decrease. In the context of treatment, to "reduce" is to either prevent or ameliorate the symptoms associate with uterine fibroids.

"Subject" means a vertebrate, such as a mammal, such as a human. Mammals include, but are not limited to, humans, dogs, cats, horses, cows, and pigs.

The term "therapeutically effective amount" refers to the amount of an agent determined to produce any therapeutic response in a mammal. For example, effective therapeutic agents may prolong the survivability of the patient, and/or inhibit overt clinical symptoms. Treatments that are therapeutically effective within the meaning of the term as used herein, include treatments that improve a subject's quality of life even if they do not improve the disease outcome perse. Such therapeutically effective amounts are readily ascertained by one of ordinary skill in the art. Thus, to "treat" means to deliver such an amount. Thus, treating can prevent or ameliorate any symptoms.

In the context of the invention a therapeutically effective amount is that amount of collagenase delivered to the uterine fibroid to the extent that such delivery results in an improvement in the clinical outcome (e.g., reduction in symptoms associated with uterine fibroids). Accordingly, the effective amounts of collagenase can be determined by empirical experimentation.

The term "therapeutically effective time" can refer to the time necessary to contact the collagenase with the uterine fibroid in order to allow for decrease in size and/or stiffness of the fibroid, and/or decrease in symptoms associated with the fibroid.

A therapeutically effective time could also refer to the time required for a subject to receive the collagenase and achieve an improved clinical result.

The term "therapeutically effective route" refers to the routes of administration that may be effective for achieving an improved clinical outcome. The therapeutically effective route means that the collagenase would be supplied at whatever site it can produce its beneficial effect. Local administration can be done by any of the effective routes that are known in the art.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

DESCRIPTION OF THE INVENTION

Collagen is the major structural constituent of mammalian organisms and makes up a large portion of the total protein content of skin and other parts of the animal body. Various skin traumas such as burns, surgery, infection and accident are often characterized by the erratic accumulation of fibrous tissue rich in collagen and having increased proteoglycan content. In addition to the replacement of the normal tissue which has been damaged or destroyed, excessive and disfiguring deposits of new tissue sometimes form during the healing process. Some diseases and conditions are associated with excess collagen deposition and the erratic accumulation of fibrous tissue rich in collagen. Such diseases and conditions are collectively referred to herein as "collagen-mediated diseases".

It has now been found that uterine fibroids are a collagen-mediated disease, associated with excess collagen deposition and the erratic accumulation of fibrous tissue rich in collagen. The considerable variation in growth rates over time of individual fibroids, and microarray studies revealing that genes encoding for ECM proteins or related to ECM synthesis and secretion account for a large portion of changes in gene expression in fibroids compared with myometrium make dysregulation of ECM (extracellular matrix) a possible contributing factor to this condition. Growth of fibroids can be considered in four phases: Phase 1, where there is cell proliferation and little collagen noted on masson trichrome stain; Phase 2, where there is cell proliferation and synthesis of collagen with interspersed collagen fibers; Phase 3, where there is proliferation, synthesis of increased collagen and early senescence; and Phase 4, where there is collagen accumulation, decreased microvascular density, cell nutritional deprivation, myocyte atrophy.

Transforming growth factor (TGF) plays a role in fibroid development. Fibroids grow by deposition of altered collagen. The expression of other molecules is likewise altered in fibroids. For example, dermatopontin expression is decreased, fibronectin and glycosaminoglycans (GAG) are increased, alpha 11 integrin, a collagenbinding integrin is expressed. In addition, fibroids are resistant to apoptosis.

Recent studies indicate that fibroids are formed by the accumulation of extracellular matrix (ECM) as well as by cellular proliferation. See FIG. 1 of U.S. Pat. No. 10,369,110, noting the disordered collagen fibrils in the fibroid tissue. The appearance and spatial orientation of collagen fibrils in uterine fibroids were shorter, randomly aligned and widely dispersed compared with those of the myometrium. They were non-aligned and not parallel whereas in the adjacent myometrium the fibrils were well packed and parallel in orientation to each other, a finding that is characteristic of collagen containing tissue. Myofibroblast type cells (elongated appearance, notched nucleus) also have been found in uterine fibroids. The notched appearance of the fibroid cell nucleus represents folding and envaginations of the nuclear membrane due to cell contraction by stress fibers.

Therefore, the present invention takes advantage of collagenase, an enzyme that has the specific ability to digest collagen, to treat uterine fibroids. Degradation of the collagen not only causes collagenolysis, it also reduces the increased cell compression leading to mechanotransduction. Thereby, the cycle of increased collagen secretion and enlargement of the uterine fibroid is broken. In summary, uterine fibroids contain an abundance of altered collagen consistent with fibrosis and stiffness. A stiff extracellular matrix (ECM) exerts force against individual cells. Mechanotransduction alters cell signaling and prevents apoptosis, and thus collagen accumulation continues. (See, FIG. 15 of U.S. Pat. No. 10,369,110.) Uterine fibroids grow at individual rates suggesting that mechanical transduction of tumors is responsible for variation in growth rates. The intersection of mechanical signaling and progesterone receptor signaling involves AKAP-13 through ERK. (Fig. Norian et al. 2012, Malik et al. 2012, Ng et al 2019).

This specification describes embodiments of an invention for treatment to reduce the symptoms of uterine fibroids, shrink uterine fibroids, reduce the stiffness and mechanical stress of fibroid tissue on the uterus and/or eliminate uterine fibroids by local delivery of a purified collagenase composition to avoid systemic side-effects and harm to other tissues. In general, some of the preferred methods use a syringe and needle under ultrasound or other visualization for guided injection of purified collagenase directly into the uterine fibroid tissue to be treated. The collagenase product preferably is in a vehicle for delivery, such as a nanocarrier or other protective or sustained release carrier.

Because the center of fibroids is more fibrotic and contains smaller vascular capillary beds than the periphery, and due to a dense vascular capsule which surrounds the fibroid tumor, systemic therapy is not likely to provide therapeutic tissue levels of a drug in the fibroid center while leaving the likely possibility of systemic effects. Thus, pharmacotherapy has not been successful for uterine fibroids. The local injection of a treatment agent under imaging guidance allows for exact tissue placement of the drug and greatly reduces the chance of systemic effects.

Uterine fibroids are classified into several types, based on their location, including subserosal, intramural, submucosal, pedunculated submucosal, fibroid in statu nascendi, and fibroid of the broad ligament. Any and all of these uterine fibroids are contemplated for treatment using the invention.

Myometrial Hyperplasia is a condition which can mimic uterine fibroid symptoms and may be a precursor lesion of these tumors. It is structural variation with irregular zones of hypercellularity and increased nucleus/cell ratio, causing a bulging, firm, enlarged uterus. The condition often leads to hysterectomy. Deeper MMH has lower cellularity, and tends to have increased collagen. Therefore, this condition also may be treated using the methods and compositions of the invention.

The local treatment of uterine fibroids by injection of collagenase can be conducted in an office or clinic visit under ultrasound guidance with minimal chance for sequelae. This method can be used to treat small to moderate size fibroids or asymptomatic fibroids, which currently are not treated at all, allowing the clinician to prevent potentially debilitating symptoms and preservation of fertility in women of child-bearing years, and also larger fibroids, eliminating the need for hysterectomy for this disease. Thus, the methods of this invention are contemplated to be useful to treat any stage or type of uterine fibroid disease.

The presence and location of uterine fibroids can be identified using any method, including ultrasound imaging. The success of treatment of uterine fibroids with collagenase can be assessed by any method known in the art, including by: (1) gross inspection; (2) analysis of collagen content (Masson's Trichrome stain, Picrosirius Red stain); (3) second harmonic generation (SHG, also called frequency doubling) and (4) and electron microscopy (EM). Results can also be assessed by examining apoptosis (using terminal deoxynucleotidyl transferase dUTP nick end labeling [TUNEL]) and rheometry.

Results of treatment can also be assessed by measuring elasticity of the treated fibroid, using strain imaging (strain elastography (SE) or acoustic radiation force impulse (ARFI) strain imaging), ultrasound elastography (USE) or by shear wave imaging (shear wave elastography index, using point shear wave elastography (pSWE/ARFI), 2D shear wave elastography (SWE), 1D transient elastography (TE) and B-mode ultrasound). Reduction in fibroid stiffness by determining a shear wave elasticity index (SWEI) may be used diagnostically. A review of these techniques can be found in Sigrist et al. 2017, which is hereby incorporated by reference in its entirety.

Collagenase for use according to the invention may be obtained from any convenient source, including mammalian (e.g., human, porcine), crustacean (e.g., crab, shrimp), fungal, and bacterial (e.g., from the fermentation of *Clostridium, Streptomyces, Pseudomonas, Vibrio* or *Achromobacter iophagus*). Collagenase can be isolated from a natural source or can be genetically engineered/recombinant. See, U.S. Pat. No. 8,715,985, incorporated herein by reference in its entirety. One common source of crude collagenase is from a bacterial fermentation process, specifically the fermentation of *Clostridium histolyticum*. The crude collagenase obtained from *C. histolyticum* can be purified using any of a number of techniques known in the art of protein purification, including chromatographic techniques. Collagenase compositions useful for the invention also can be prepared using any commercially available or isolated collagenase activity, or by mixing such activities. For example, purified collagenase can be provided by Biospecifics Technologies, Lynbrook, NY.

Preferred collagenases for use in the invention are from *C. histolyticum*, i.e., collagenase class I and class II. A practical advantage of using *C. histolyticum* for the production of collagenases is that it can be cultured in large quantities in simple liquid media, and it regularly produces amounts of proteolytic enzymes which are secreted into the culture medium. Bovine products have been used in culture media in the fermentation of *C. histolyticum*, but these run the risk of contamination by agents which cause transmissible spongiform encephalopathies (TSEs; e.g., prions associated with bovine spongiform encephalopathy or "mad cow disease"). Therefore, it is preferred to avoid such bovine products. An animal-product-free system is preferred. The H4 strain of *Clostridium histolyticum*, originally developed in 1956 can serve as a source for cells for culture. This strain, and a strain derived from the H4 strain, named the ABC *Clostridium histolyticum* master cell bank (deposited as ATCC 21000) were developed using animal products, but are suitable to use in the invention.

U.S. Pat. No. 7,811,560, which is incorporated herein by reference in its entirety, discloses methods of producing collagenases. Using soybean derived fermentation medium, the methods described therein generated separately highly purified collagenase I and II. This patent also discloses methods of producing highly purified collagenases using culture media containing porcine-derived products. Any of these methods are suitable for use with the invention. U.S. Patent Publication 2010/0086971, which is also incorporated herein by reference in its entirety, discloses numerous fermentation recipes which are based on vegetable peptone, including soybean-derived peptone, or vegetable-derived peptone plus fish gelatin. The methods described in this publication are suitable to produce growth of *Clostridium* and collagenase activities. These methods also are suitable and contemplated for use with the invention, however any method known in the art of producing collagenase enzyme activity may be used.

In preferred culture methods, the peptone is from a plant source selected from the group consisting of soy bean, broad bean, pea, potato, and a mixture thereof. The peptone may be selected from the group consisting of Oxoid VG100 Vegetable peptone No. 1 from pea (VG100), Oxoid VG200 Vegetable peptone phosphate broth from Pea (VG200), Merck TSB CASO-Bouillion animal-free (TSB), Invitrogen Soy bean peptone No 110 papainic digest (SP6), Fluka Broad bean peptone (BP), Organotechnie Plant peptone E1 from potato (E1P), BBL Phytone™ peptone and BD Difco Select Phytone™.

In a preferred embodiment of the invention, a single type of peptone is present in the nutrient composition of the invention, whereby the peptone is selected from the group consisting of BP, E1P, Soy bean peptone E110, VG100, and VG200, and whereby the concentration of the peptone in the composition is about 5% weight by volume. In yet another very much preferred embodiment of the invention, a single type of peptone is present in the nutrient composition of the invention, whereby the peptone is BBL phytone peptone or Difco Select Phytone™ UF, and whereby the concentration of the peptone in the composition is about 10-13% weight by volume.

Preferred methods of isolating collagenase avoid undesirable contaminating proteases such as clostripain. Clostripain, a cysteine protease, is believed to be a major cause of collagenase degradation and instability, and is present in *Clostridium* culture. When such proteases are present in a crude collagenase mixture, one must take extra precautions to neutralize the proteases, including using protease inhibitors, such as leupeptin, and performing all of the purification steps in specially designed cold rooms with chilled solutions to reduce protease activity. Preferred methods of isolation therefore take advantage of one of two approaches to avoid clostripain: remove clostripain as early as possible in the purification method or reduce clostripain production during the fermentation stage.

Preferred collagenase compositions are produced by fermenting *C. histolyticum* in medium free of animal material-derived ingredients and are substantially free of clostripain, and thus are highly stable. "Substantially free" indicates that the collagenase contains less than 10 U clostripain per mg total collagenase, more preferably less than 5 U/mg, and most preferably about 1 U/mg or less, and/or that no visible band appears representing clostripain and/or degraded collagenase on SDS-PAGE gel compared to a reference standard.

Preferred methods for purifying collagenase involve using a "low glucose" medium as described herein, which contains less than about 5 g/L glucose, more preferably less than about 1 g/L, even more preferably less than about 0.5 g/L glucose, or is glucose-free, for culture of *C. histolyticum*. High salt concentrations in the growth media can reduce the amount of clostripain produced in culture, thus preferred media for *C. histolyticum* culture contain greater than about 5 g/L (or 0.5% w/v) total salt, more preferably greater than about 7.5 g/L (or 7.5%) total salt, and more preferably about 9 g/L (or 9%) or more. It is contemplated that any salt known to be suitable for use in microbiological fermentation media may be used in the current invention. In a preferred embodiment, chloride, phosphate or sulfate salts may be used. In a more preferred embodiment, the salts may be sodium chloride, potassium chloride, monosodium phosphate, disodium phosphate, tribasic sodium phosphate, potassium monophosphate, potassium diphosphate, tripotassium phosphate, calcium chloride, magnesium sulfate or various combinations thereof. In certain embodiments, potassium diphosphate may be about 0.1-0.3%, potassium phosphate may be about 0.75% to 0.175%, sodium phosphate may be about 0.2-0.5%, and/or sodium chloride may be about 0.15-0.35%. Preferably, the medium further comprises magnesium sulfate and vitamins, including, riboflavin, niacin, calcium pantothenate, pimelic acid, pyridoxine and thiamine.

In another preferred embodiment, the nutrient composition may contain 0.5-5% yeast extract, more preferably about 1-4%, and most preferably about 1.5-2.5%. Yeast extract is available from a variety of suppliers, including Cole Parmer (Vernon Hills, Illinois) and Fisher Scientific (Pittsburgh, PA).

In yet a preferred embodiment of the invention, the pH of the media is between pH 7 and pH 8. Even more preferred is a pH between about pH 7.2 and about pH 7.7, most preferably about 7.4.

The collagenase contemplated for use with the invention can be any collagenase which is active under the necessary conditions. However, preferred compositions contain a mass ratio of collagenase I and collagenase II which is modified or optimized to produce a desired or even a maximal synergistic effect. Preferably, collagenase I and collagenase II are purified separately from the crude collagenase mixture produced in culture, and the collagenase I and collagenase II are recombined in an optimized fixed mass ratio. Preferred embodiments contain a collagenase I to collagenase II mass ratio of about 0.5 to 1.5, more preferably 0.6 to 1.3, even more preferably 0.8 to 1.2, and most preferably, 1 to 1, however any combination or any single collagenase activity may be used.

A preferred method of producing collagenase which is contemplated for use with the invention involves fermenting *C. histolyticum* in a non-mammalian or nonanimal medium, wherein the culture supernatant is substantially clostripain-free. The collagenases so produced can be isolated, purified, and combined to provide a composition for use in the invention which comprises a mixture of collagenase I and collagenase II in an optimized fixed mass ratio which is substantially clostripain-free. The crude collagenase obtained from fermentation of *C. histolyticum* may be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and/or metal chelation chromatography. Additionally, purification methods for collagenases are known, such as, for example, those described in U.S. Pat. No. 7,811,560, which is hereby incorporated by reference in its entirety.

Both collagenase I and collagenase II are metalloproteases and require tightly bound zinc and loosely bound calcium for their. Both collagenases have broad specificity toward all types of collagen. Collagenase I and Collagenase II digest collagen by hydrolyzing the triple-helical region of collagen under physiological conditions. Each collagenase shows different specificity (e.g. each have a different preferred target amino sequence for cleavage), and together they have synergistic activity toward collagen. Collagenase II has a higher activity towards all kinds of synthetic peptide substrates than collagenase I as reported for class II and class I collagenase in the literatures.

The preferred collagenase consists of two microbial collagenases, referred to as Collagenase ABC I and Collagenase ABC II. The terms "Collagenase I", "ABC I", and "collagenase ABC I" mean the same and can be used interchangeably. Similarly, the terms "Collagenase II", "ABC II", and "collagenase ABC II" refer to the same enzyme and can also be used interchangeably. These collagenases are secreted by bacterial cells. Preferably, they are isolated and purified from *Clostridium histolyticum* culture supernatant by chromatographic methods. Both collagenases are special proteases and share the same EC number (E.C 3.4.24.3). However, a collagenase or a combination of collagenases from other sources are contemplated for use with the invention. Collagenase ABC I has a single polypeptide chain consisting of approximately 1000 amino acids with a molecular weight of 115 kDa. Collagenase ABC II has also a single polypeptide chain consisting of about 1000 amino acids with a molecular weight of 110 kDa.

Collagenase acts by hydrolyzing the peptide bond between Gly-Pro-X, wherein X is often proline or hydroxyproline. Collagenase I acts at loci at ends of triplehelical domains, whereas Collagenase II cleaves internally. Hydrolysis continues over time until all bonds are cleaved.

Preferably, the collagenase product is at least 95% pure collagenase(s) and is substantially free of any contaminating proteases. More preferably, the collagenase product is 97% pure and most preferably 98% pure or more as determined by one or more of the following: sodium dodecyl sulfate polyacrylamide gel electrophoresis (SDS-PAGE); high performance liquid chromatography (HPLC); reverse-phase HPLC; or by enzymatic assays. The preferred collagenase product is essentially clostripain-free, and the purification preferably is performed in the absence of leupeptin. The preferred collagenase product for use with the invention has at least one specification selected from Table 1 below.

TABLE 1

Preferred Specifications for Collagenase Products

| Test | Specification | |
|---|---|---|
| | ABC-I | ABC-II |
| Appearance | Clear colorless and essentially free from particulate matter | |
| Endotoxin | <10 EU/mL | |
| Identity (and purity) by SDS-PAGE (Reduced conditions, Coomasie) | Major collagenase band between 98-188 kDa >95% | Major collagenase band between 97-200 kDa >95% |

TABLE 1-continued

Preferred Specifications for Collagenase Products

| Test | Specification | |
|---|---|---|
| | ABC-I | ABC-II |
| SRC assay (ABC-I) | 1967-3327 SRC units/mg | NA |
| GPA assay (ABC-II) | | NA81934 - 119522 GPA units/mg |
| Analysis of Proteins HPLC System (Aggregation by size exclusion chromatography) | >98% main peak; <2% aggregates by area | |
| Identity and purity by reverse phase liquid chromatography) | Major peak (ABC I or ABC II), >95% by area; Retention times of ABC-I and ABC-II within 5% of reference | |
| Clostripain assay (BAEE assay) | <1 U/mg | |
| Bioburden | <1 cfu/mL | |

The collagenase products described for use herein are useful for the treatment of collagen-mediated disease, including uterine fibroids. Examples of other collagen mediated-diseases that may be treated by the compositions of the invention include but are not limited to: Dupuytren's disease; Peyronie's disease; frozen shoulder (adhesive capsulitis), keloids; tennis elbow (lateral epicondylitis); scarred tendon; glaucoma; herniated discs; adjunct to vitrectomy; hypertrophic scars; depressed scars such as those resulting from inflammatory acne; post-surgical adhesions; acne vulgaris; lipomas, and disfiguring conditions such as wrinkling, cellulite formation and neoplastic fibrosis.

In addition to its use in treating specific collagen-mediated diseases, the compositions of the invention also are useful for the dissociation of tissue into individual cells and cell clusters as is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. In general, the compositions of the present invention are useful for any application where the removal of cells or the modification of an extracellular matrix, are desired.

The collagenase compositions according this invention are designed to administer to a patient in need thereof a therapeutically effective amount of a collagenase composition as described, or a therapeutically effective amount of a pharmaceutical collagenase formulation as described. A "therapeutically effective amount" of a compound, composition or formulation is an amount of the compound which confers a therapeutic effect on the treated subject, at a reasonable benefit/risk ratio applicable to any medical treatment. A therapeutic effect includes but is not limited to a shrinkage or reduction in the size (e.g., volume) of one or more uterine fibroids (including elimination of the fibroid), liquification, partial liquification, or reduction in stiffness (increase in softness) or bloating or pressure in or around a uterine fibroid, a change in viscoelastic properties, or reduction in symptoms such as pain, hemorrhage and the like.

The therapeutic effect may be objective (i.e., measurable by some test or marker) or subjective (i.e., subject gives an indication of or feels an effect), and may be determined by the clinician or by the patient. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, and diet of the patient; the time of administration, route of administration, and rate of excretion of the specific compound employed; the duration of the treatment; drugs used in combination or contemporaneously with the specific compound employed; and like factors well known in the medical arts.

The term "patient" or "patient in need" encompasses any mammal having a uterus and uterine fibroids or symptoms thereof. Such "patients" or "patients in need" include humans or any mammal, including farm animals such as horses and pigs, companion animals such as dogs and cats, and experimental animals such as mice, rats and rabbits. Preferred patients are human females of child-bearing age.

The pharmaceutical compositions of this invention preferably are administered by injection, insertion or implantation directly into or onto the uterine fibroid tissue to be treated, i.e. local administration to the tissue to be treated. Other modes of administration contemplated included, but are not limited to transvaginal instillation or application onto the affected tissues, instillation or application during surgery (such as laparoscopy or hysteroscopy) onto the affected tissues, i.e. topical administration to the fibroid tissue, by spray or other application of a liquid, fluid or gel formulation.

Formulations of the present invention are injected/inserted into uterine tissue in a variety of forms, by a variety of routes, using a variety of apparatuses. In some embodiments, the formulation is injected/inserted using an apparatus consisting of a simple needle (e.g., a 10 gauge or smaller needle) and sample pusher (e.g., a mandrel or modified obturator). For example, according to one embodiment, a formulation (e.g., a rod-shaped or other shaped solid or semi-solid formulation, beads, suspension, gel, polymer or the like) is placed in the needle or in a syringe or other chamber affixed to the needle. Once the needle is placed at the desired depth and location in the tissue, the pusher is used to push the sample from the needle and into the tissue. In some embodiments, the sample pusher is provided with a holding clip or it is provided with a hollow end to secure the sample up to the time of delivery.

In still other embodiments, formulations in accordance with the present invention are injected/inserted via jet injection without a physical delivery channel such as a needle, as is known in the art. Typically, a compression system (e.g., a mechanical system or a gas, such as helium, nitrogen, carbon dioxide, etc.) is used to accelerate the formulations to a high enough velocity so that the formulation can penetrate the tissue to a desired depth. Jet injector devices can be, for example, disposable, or reusable with medication cartridges that are prefilled or non-prefilled medication cartridges. Examples of jet injectors include Biojector® from Bioject, N.J., USA and the PowderJect® System from PowderJect, UK. In other embodiments, a device is employed that cores out a section of the fibroid (e.g., a biopsy device or tissue morcellator or laser radiation), thereby leaving behind a void for insertion of a dosage form.

The formulations for collagenase delivery to a patient generally are contemplated to comprise injectable or implantable formulations, or any fluid, liquid, solid, semi-solid, gel, or other composition which is suitable to administer the collagenase to the tissue to be treated as described herein. Formulations in accordance with the present invention may be formulated by any method known in the pharmaceutical arts. Thus, any injectable or implantable formulation known in the art and consistent with collagenase activity may be used. Formulations which create a depot or extended release of the active collagenase agent are contemplated. In particular, injectable extended or sustained release compositions are preferred, however any implantable formulation can be used. Such compositions produce or form a depot effect, where active agent is present in the tissue where administered and release active agent over a period of time to continuously treat the tissue. Immediate release injectable formulations, where the active agent is immediately released for activity upon administration, also are contemplated for use with the invention. These formulations are known in the art and can be adapted for use with the present invention by any person of skill.

In some embodiments, the injectable or insertable formulations of the present invention are solids, semi-solids or high-viscosity fluids. This improves dosage retention in the tissue, thereby improving delivery efficiency of the treatment agents and/or minimizing the adverse effects such as unintended, nonspecific tissue damage. "High viscosity" and other such terms are used herein to describe fluids having viscosities greater than 1000 centipoise as measured by any of a number of standard techniques, including, for example, a Brookfield Kinematic Viscometer, model HBDV-II+CP with a CPE-40 cone spindle, set at 37° C. and using a 0.5 rpm speed setting. "Low viscosity" fluids have viscosities less than this value.

In some embodiments, a formulation in accordance with the present invention is injected into a patient in a fluid state, whereupon it converts (or is converted) in vivo into a more readily retained form, for example, into a solid form (including conversion of an injected liquid into a solid, conversion of an injected semisolid into a solid and conversion of a liquid into a gel), into a semi-solid form (including conversion of an injected liquid into a semi-solid, conversion of an injected semi-solid into a semi-solid having increased yield stress and/or viscosity and conversion of a liquid into a gel), or into a high-viscosity fluid (including conversion of a low-viscosity fluid into a high-viscosity fluid, and conversion of a high-viscosity fluid into a higher-viscosity fluid).

Preferred formulations for injection into a uterine fibroid use a carrier or nanocarrier. Appropriate carriers include solid or semi-solid pellets, beads or gelforming polymers, high-viscosity liquids and the like to maintain the active collagenase in the tissue, protecting the active enzyme from action of the tissue or tissue components which could inactivate the collagenase, and allow steady release of the enzyme to the tissue for treatment. Any injectable dosage form which can protect and contain the active compound(s) in place may be used. In mammals, C. histolyticum collagenase is inhibited rapidly in the blood stream by serum. Therefore, systemic administration, or administration under conditions where the collagenase can be deactivated, or orally, where the collagenase can be degraded by digestive enzymes, is problematic.

Nanocarriers are designed to deliver and protect drug therapeutics (e.g. proteins, for example) from degradation. A nanocarrier formulation also is preferred because this method impedes diffusion and distribution of the drug away from the injected fibroid, prolongs release, delays inactivation, and therefore reduces the frequency of repeat injections. Any such nanocarrier known in the art can be used with the invention. Some of these nanocarriers also are referred to as thermoresponsive delivery systems.

Atrigel® comprises a water-insoluble biodegradable polymer (e.g., poly(lactic-co-glycolic acid, PLGA) dissolved in a bio-compatible, water-miscible organic solvent (e.g., N-methyl-2-pyrrolidone, NMP). In use, collagenase is added to form a solution or suspension. Both the PLGA molecular weight and lactide-glycolide molar ratio (L:G ratio) governs drug delivery. Using an L:G ratio of from 50:50 to 85:15 and a polymer concentration of from 34 to 50%, clinical studies have demonstrated a depot which was maintained for more than 3 months.

ReGel® is a 4000 Da triblock copolymer formed from PLGA and polyethylene glycol (PEG, 1000 Da or 1450 Da) in repetitions of PLGA-PEG-PLGA or PEG-PLGA-PEG. ReGel® is formulated as a 23 wt % copolymer solution in aqueous media. A drug is added to the solution and upon temperature elevation to 37° C. the whole system gels. Degradation of ReGel® to final products of lactic acid, glycolic acid and PEG occurs over 1-6 weeks depending on copolymer molar composition. Chemically distinct drugs like porcine growth hormone and glucagon-like peptide-1 (GLP-1) may be incorporated, one at a time, and released from ReGel®.

LiquoGel™ can work by mechanistically independent drug delivery routes: entrapment and covalent linkage. Two or more drugs can be delivered to the tumor site using this carrier. LiquoGel™ is a tetrameric copolymer of thermogelling N-isopropylacrylamide; biodegrading macromer of poly(lactic acid) and 2-hydroxyethyl methacrylate; hydrophilic acrylic acid (to maintain solubility of decomposition products); and multi-functional hyperbranched polyglycerol to covalently attach drugs. LiquoGel™ generally is formulated as a 16.9 wt % copolymer solution in aqueous media. The solution gels under physiological conditions and degrades to release drug contents within 1-6 days.

Any of the above carriers can be used as a nanocarrier with the invention. A preferred nanocarrier, however, contains hyperbranched polyglycerols (HPG), which have many desirable features. HPGs grow by imperfect generations of branched units and are produced in a convenient single step reaction. Previous problems of large polydispersities in molecular weight in their production have been overcome. The resulting polymers contain a large number of modifiable surface functional groups as well as internal cavities for drug interaction. Other polymer approaches cannot easily provide these properties without significant increases in the number of synthetic steps and, consequently, cost. HPG polymers are based on glycerol and because of structural similarity with polyethylene glycol, is biocompatible.

Additional components optionally can be added to the polymer, therefore, modified HPG polymers and co-polymers of HPG are contemplated. These additional components or monomers can include, for example, crosslinks, biodegradable moieties, and thermoresponsive moieties. For example, thermally responsive hydrogels are attractive for injection therapy since it is possible to inject the necessary fluid volume from a syringe maintained below body temperature and upon warming, the mechanical properties are increased, thereby restraining the material at the injection site. Poly(N-isopropylacrylamide) (poly-NIPAAm) is a thermally responsive polymer with a lower critical solution temperature (LOST) of approximately 32° C. Copolymers of HPG with NIPAAm are therefore contemplated for use with the invention, and are preferred. This nanocarrier has a versatile mesh size and can be customized to entrap small drug molecules, large proteins, or a mixture of components, and gels at body temperature to permit slow release as the nanocarrier biodegrades.

In preferred embodiments of the invention, formulations exist as a liquid at temperatures below body temperature and as a gel at body temperature. The temperature at which a transition from liquid to gel occurs is sometimes referred to as the LOST, and it can be a small temperature range as opposed to a specific temperature. Materials possessing an LOST are referred to as LOST materials. Typical LCST's for the practice of the present invention range, for example, from 10 to 37° C. As a result, a formulation injected below the LOST warms within the body to a temperature that is at or above the LOST, thereby undergoing a transition from a liquid to a gel.

Suitable LOST materials for use with the invention include polyoxyethylene-polyoxypropylene (PEO-PPO) block copolymers. Two acceptable compounds are Pluronic acid F127 and F108, which are PEO-PPO block copolymers with molecular weights of 12,600 and 14,600, respectively. Each of these compounds is available from BASF (Mount Olive, N.J.). Pluronic acid F108 at 20-28% concentration, in phosphate buffered Saline (PBS) is an example of a suitable LOST material. One beneficial preparation is 22.5% Pluronic acid F108 in PBS. A preparation of 22% Pluronic acid F108 in PBS has an LOST of 37°C. Pluronic acid F127 at 20-35% concentration in PBS is another example of a suitable LOST material. A preparation of 20% Pluronic acid F127 in PBS has an LOST of 37°C. Typical molecular weights are between 5,000 and 25,000, and, for the two specific compounds identified above are 12,600 and 14,600. More generally, materials, including other PEO-PPO block copolymers, which are biodisintegrable, and which exist as a gel at body temperature and as a liquid below body temperature can also be used according to the present invention. Further information regarding LOST materials can be found in U.S. Pat. Nos. 6,565,530 B2 and 6,544,227 B2, each of which is hereby incorporated by reference.

Pharmaceutical formulations of the collagenase compounds for the invention include a collagenase composition formulated together with one or more pharmaceutically acceptable vehicles or excipients. As used herein, the term "pharmaceutically acceptable carrier or excipient" means a non-toxic, inert, solid, semi-solid or liquid filler, diluent, encapsulating material, vehicle, solvent, or formulation auxiliary of any type, and may be made available in individual dosage forms or in bulk. Other dosage forms designed to create a depot of the active compound also are contemplated for use with the invention. Dosage forms for collagenase suitable for use with the invention include, but are not limited to lyophilized or other dried powder for reconstitution prior to injection, in multiple or single dose amounts, individual dosage units ready for injection (which preferably also include one or more preservatives), frozen unit dosage forms, or any mode of preparation known in the art. The formulations also may be provided in the form of a kit, which can contain the collagenase in solid form, liquid or solvent for reconstitution and injection, and any equipment necessary for administration, such as a syringe and needle, particularly a specialized syringe and/or needle for administration to a uterine fibroid. Preferably, the dosage form has a largest dimension between 1 mm and 20 mm. Preferably, the formulations are sterile. The products may be sterilized by any method known in the art, such as by filtration through a bacterial-retaining filter or are produced under aseptic conditions. Other methods include exposing the formulation or components thereof to heat, radiation or ethylene oxide gas.

Some examples of materials which can serve as pharmaceutically acceptable carriers are solvents for injection as known in the art. Examples include, but are not limited to sterile water, buffering solutions, saline solutions such as normal saline or Ringer's solution, pyrogen-free water, ethyl alcohol, non-toxic oils, and the like, or any solvent compatible with injection or other forms of administration as described herein for use with the invention.

In addition, any solid excipients known in the art for use in pharmaceutical products can be used with the invention as a vehicle or filler, for example. Sugars such as lactose, glucose and sucrose; starches such as corn starch and potato starch; cellulose and its derivatives such as microcrystalline cellulose, sodium carboxymethyl cellulose, ethyl cellulose and cellulose acetate; powdered tragacanth; malt; gelatin; gums; talc; glycols such as propylene glycol; esters such as ethyl oleate and ethyl laurate; agar, and the like can be used. Buffering agents compatible with the active compounds and the methods of use are contemplated for use, including acid or alkali compounds, such as magnesium hydroxide and aluminum hydroxide, citric acid, phosphate or carbonate salts and the like. Non-toxic compatible excipients such as lubricants, emulsifiers, wetting agents, suspending agents, binders, disintegrants, preservatives or antibacterial agents, antioxidants, sustained release excipients, coating agents and the like (e.g., sodium lauryl sulfate and magnesium stearate) also may be used, as well as coloring agents, perfuming agents, viscosity enhancing agents, bioadhesives, and the like, according to the judgment of the formulator.

For example, one or more biodisintegrable binders may be included in the formulations of the present invention, typically in connection with dosage forms having solid characteristics. Where employed, a wide range of biodisintegrable binder concentrations may be utilized, with the amounts varying based, for example, on the desired physical characteristics of the resulting dosage form and on the characteristics of the uterine fibroid treatment agent that is selected (e.g., the degree of dilution, release delay, etc. that is desired/tolerated), among other considerations. The concentration of biodisintegrable binder typically ranges are from about 1 to 80 wt % of biodisintegrable binder, more typically about 5 to 50 wt %. A "biodisintegrable" material is one that, once placed in tissue such as uterine tissue, undergoes dissolution, degradation, resorption and/or other disintegration processes. Where such materials are included, formulations in accordance with the present invention will typically undergo at least a 10% reduction in weight after residing in tissue such as uterine tissue for a period of 7 days, more typically a 50-100% reduction in weight after residing in the tissue for a period of 4 days. Suitable biodisintegrable binders for use in connection with the present invention include, but are not limited to biodisintegrable organic compounds, such as glycerine, and biodisintegrable polymers, or any known disintegrant compound known in the art of pharmaceutics.

Where used, viscosity adjusting agent(s) are typically present in an amount effective to provide the formulation with the desired viscosity, for example, by rendering the formulation highly viscous, for example, in an amount effective to provide a viscosity between about 5,000 and 200,000 centipoise, more typically between about 10,000 and 100,000 centipoise, more typically between about 10,000 and 50,000 centipoise, and even more typically between about 20,000 and 40,000 centipoise. By providing formulations having viscosities within these ranges, the formulations can be injected into tissue, such as uterine tissue, using conventional injection equipment (e.g., syringes). However, due to their elevated viscosities, the formulations have improved retention within the tissue at the injection site. The concentration of the viscosity adjusting agent(s) that is (are) used can vary widely. Commonly, the overall concentration of the viscosity adjusting agent(s) is between about 1 and 20 wt %. In many embodiments, the viscosity adjusting agents are polymers, which may be of natural or synthetic origin and are typically biodisintegrable. The polymers are also typically water soluble and/or hydrophilic. However, in some embodiments, for instance where an organic solvent such as dimethylsulfoxide (DMSO) is used as a liquid component, the viscosity adjusting agent can be relatively hydrophobic. The polymeric viscosity adjusting agents include homopolymers, copolymers and polymer blends.

Examples of viscosity adjusting agents for the practice of the present invention include, but are not limited to the following: cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, hydroxyethyl starch (HES), dextran, dextran derivatives, chitosan, and alginic acid and its various salts, carrageenan, various gums, including xanthan gum, guar gum, gum arabic, gum karaya, gum ghatti, konjac and gum tragacanth, glycosaminoglycans and proteoglycans such as hyaluronic acid and its salts, heparin, heparin sulfate, dermatan sulfate, proteins such as gelatin, collagen, albumin, and fibrin, other polymers, for example, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide and polyethylene oxide-propylene oxide) (e.g., Pluronic acid), polyoxyethylene (polyethylene glycol), polyethyleneamine and polypyrridine, poly-metaphosphate (Kurrol salts), polyvinyl alcohol, additional salts and copolymers beyond those specifically set forth above, and blends of the foregoing (including mixtures of polymers containing the same monomers, but having different molecular weights), and so forth. Many of these species are also useful as binders.

In other embodiments of the invention, formulations or carriers are crosslinked, either prior to use or in vivo. Crosslinking is advantageous, for example, in that it acts to improve formulation retention (e.g., by providing a more rigid/viscous material and/or by rendering the polymer less soluble in a particular environment). Where the formulation is crosslinked in vivo, a crosslinking agent is commonly injected into tissue either before or after the injection or insertion of a formulation in accordance with the present invention. Depending on the nature of the formulation and the crosslinking agent, the formulation may be converted, for example, into a solid, into a semi-solid, or into a high-viscosity fluid.

Crosslinking agents suitable for use in the present invention include, any non-toxic crosslinking agent, including ionic and covalent crosslinking agents. For example, in some embodiments, polymers are included within the formulations of the present invention, which are ionically crosslinked, for instance, with polyvalent metal ions. Suitable crosslinking ions include polyvalent cations selected from the group consisting of calcium, magnesium, barium, strontium, boron, beryllium, aluminum, iron, copper, cobalt, lead and silver cations ions. Polyvalent anions include phosphate, citrate, borate, succinate, maleate, adipate and oxalate anions. More broadly, crosslinking anions are commonly derived from polybasic organic or inorganic acids. Ionic crosslinking may be carried out by methods known in the art, for example, by contacting ionically crosslinkable polymers with an aqueous solution containing dissolved ions.

In some embodiments, polymers are included, which are covalently crosslinkable, for example, using a polyfunctional crosslinking agent that is reactive with functional groups in the polymer structure. The polyfunctional crosslinking agent can be any compound having at least two functional groups that react with functional groups in the polymer. Various polymers described herein can be both covalently and ionically crosslinked.

Suitable polymers for ionic and/or covalent crosslinking can be selected, for example, from the non-limiting list of the following: polyacrylates; poly(acrylic acid); poly(methacrylic acid); polyacrylamides; poly(N-alkylacrylamides); polyalkylene oxides; polyethylene oxide); polypropylene oxide); poly(vinyl alcohol); poly(vinyl aromatics); poly(vinylpyrrolidone); polyethylene imine); polyethylene amine); polyacrylonitrile; poly(vinyl sulfonic acid); polyamides; poly(L-lysine); hydrophilic polyurethanes; maleic anhydride polymers; proteins; collagen; cellulosic polymers; methyl cellulose; carboxymethyl cellulose; dextran; carboxymethyl dextran; modified dextran; alginates; alginic acid; pectinic acid; hyaluronic acid; chitin; pullulan; gelatin; gellan; xanthan; carboxymethyl starch; hydroxyethyl starch; chondroitin sulfate; guar; starch; and salts, copolymers, mixtures and derivatives thereof.

In one preferred embodiment, the collagenase is formulated as a lyophilized injectable composition formulated with lactose, sucrose or any suitable sugar. One preferred collagenase composition is a lyophilized injectable composition formulated with sucrose, Tris at a pH level of about 8.0. Most preferably, 1.0 mg of the drug substance of the invention is formulated in 60 mM sucrose, 10 mM Tris, at a pH of about 8.0 (e.g., about 20.5 mg/mL of sucrose and 1.21 mg/mL of Tris in the formulation buffer).

Preferred collagenase compositions for use in the invention comprise a mixture of collagenase I and collagenase II has a specific activity of at least about 700 SRC units/mg, such as at least about 1000 SRC units/mg, more preferably at least about 1500 SRC units/mg. One SRC unit will solubilize rat tail collagen into ninhydrin reaction material equivalent to 1 nanomole of leucine per minute, at 25° C., pH 7.4. Collagenase has been described in ABC units as well. This potency assay of collagenase is based on the digestion of undenatured collagen (from bovine tendon) at pH 7.2 and 37°C. for 20-24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute. One SRC unit equal approximate 6.3 ABC unit or 18.5 GPA unit. In one embodiment, each milligram of collagenase for injection will contain approximately 2800 SRC units.

Doses contemplated for administration by direct injection to the uterine fibroid tissue will vary depending on the size of the tissue to be treated and the discretion of the treating physician. However, doses can range from 0.005 mg to 10 mg, preferably about mg collagenase to about 1 mg collagenase per cm$^3$ of tissue to be treated or about mg collagenase to about 0.8 mg collagenase per cm$^3$ of tissue to be treated, or about 0.2 mg collagenase to about 0.6 mg collagenase per cm$^3$ of tissue to be treated. Examples of suitable doses include about 0.25 mg, about 0.5 mg, about 1 mg, about 1.68 mg, about 2 mg about 3.35 mg or about 5.028 mg.

Formulations that contain an additional active agent or medication also are contemplated. Optional additional agents which can be included in the formulation for concomitant, simultaneous or separate administration include, for example, any pharmaceutical known in the art for shrinkage, treatment or elimination of uterine fibroids or their symptoms, or to assist in performance of the present treatment methods. For example, one or more fibroid treatment agents such as aromatase inhibitors (e.g., letrozole, anastrozole, and exemestande), progesterone receptor agonists and modulators (e.g., progesterone, progestins, mifepristone, levonoergestrel, norgestrel, asoprisnil, ulipristal and ulipristal acetate, vilaprisan, telepristone), selective estrogen receptor modulators (SERMs) (e.g., benzopyran, benzothiophenes, chromane, indoles, naphtalenes, tri-phenylethylene compounds, arzoxifene, EM-652, CP 336,156, raloxifene, 4-hydroxytamoxifen and tamoxifen), gonadotrophin-releasing hormone analogs (GnRHa) (e.g., GnRH agonist peptides or analogs with D-amino acid alterations in position 6 and/or ethyl-amide substitutions for carboxyl-terminal Gly10-amide such as triptorelin or GnRH antagonists such as cetrorelix, ganirelix, degarelix and ozarelix), Elagolix, Relugolix, Linzagolix, Orilissa, growth factor modulators (e.g., TGFb neutralizing antibodies), leuprolide acetate (Lupron), non-steroidal antiinflammatory drugs, inhibitors of the mTOR pathway, inhibitors of the WNT signaling pathway, vitamin D, vitamin D metabolites, vitamin D modulators, and/or an additional anti-fibrotic compound (e.g., pirfenidone and halofuginone) may be co-administered with collagenase in the same or a separate administration.

The methods of the present invention can also be combined with herbal therapies, to improve uterine bleeding and shrink fibroids with Kue-chin-fuling-man (KBG), to reduce estrogen with augmented rambling powder, cinnamon twig, poria pill, dong quai, peony powder and four substance decoction, to modulate cell proliferation with green tea (catechins especially epigallocatechin-3-gallate or EGCG), to stop bleeding with cinnamon oil, and to stop pelvic inflammation with reishi.

Chemical ablation agents also can be included in the formulations of the present invention. In effective amounts, such compounds cause tissue necrosis or shrinkage upon exposure. Any known ablation agent can be used according to the art, in concentrations as appropriate to the conditions while avoiding inactivation of the collagenase, with the amounts employed being readily determined by those of ordinary skill in the art. Typical concentration ranges are from about 1 to 95 wt % of ablation agent, more typically about 5 to 80 wt %. Ablation agents suitable for use with the invention include, but are not limited to osmotic-stress-generating agents (e.g., a salt, such as sodium chloride or potassium chloride), organic compounds (e.g., ethanol), basic agents (e.g., sodium hydroxide and potassium hydroxide), acidic agents (e.g., acetic acid and formic acid), enzymes (e.g., hyaluronidase, pronase, and papain), free-radical generating agents (e.g., hydrogen peroxide and potassium peroxide), oxidizing agents (e.g., sodium hypochlorite, hydrogen peroxide and potassium peroxide), tissue fixing agents (e.g., formaldehyde, acetaldehyde or glutaraldehyde), and/or coagulants (e.g., gengpin). These agents may be combined with collagenase in the same formulation so long as they do not negatively affect the enzymatic activity of the collagenase, or they may be administered separately, at the same time or at different times.

The methods according to the invention may be used in conjunction with any known treatments to control symptoms caused by fibroids. For example, NSAIDs or other analgesics can be used to reduce painful menses, oral contraceptive pills are may be prescribed to reduce uterine bleeding, and iron supplementation may be given to treat anemia. A levonorgestrel intrauterine device can be used to reduce hemorrhage and other symptoms if the condition of the uterus does not result in expulsion of the device.

The ability to non-invasively image regions where the formulations of the present invention are being introduced and where they have been introduced is a valuable diagnostic tool for the practice of the present invention. Therefore, in addition to a uterine fibroid treatment agent and any of the various optional components discussed above, the uterine fibroid formulations of the present invention also optionally include one or more imaging contrast agents to assist with guiding the clinician to administer the collagenase compound to the fibroid or tissue to be treated or to determine that administration has been correctly located. Non-non-invasive imaging techniques include magnetic resonance imaging (MRI), ultrasonic imaging, x-ray fluoroscopy, nuclear medicine, and others. Any contrast agent suitable for use with such techniques and known in the art can be used as part of the inventive compositions and formulations.

Any real-time imaging technology can be used to guide injection or insertion in the invention. For example, X-ray based fluoroscopy is a diagnostic imaging technique that allows real-time patient monitoring of motion within a patient. To be fluoroscopically visible, formulations are typically rendered more X-ray absorptive than the surrounding tissue. In various embodiments of the invention, this is accomplished by the use of contrast agents. Examples of contrast agents for use in connection with X-ray fluoroscopy include metals, metal salts and oxides (particularly bismuth salts and oxides), and iodinated compounds. More specific examples of such contrast agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine.

Ultrasound and magnetic resonance imaging can provide two- and/or three-dimensional images of a portion of the body. Ultrasound and MRI are advantageous, inter alia, because they do not expose the patient or medical practitioner to harmful radiation and they can provide detailed images of the observed area. These detailed images are valuable diagnostic aids to medical practitioners and can be used to more precisely control the quantity and location of the formulations of the present invention.

Suitable ultrasonic imaging contrast agents for use in connection with the present invention include solid particles ranging from about 0.01 to 50 microns in largest dimension (e.g., the diameter, where spherical particles are used), more typically about 0.5 to 20 microns. Both inorganic and organic particles can be used. Examples include microparticles/microspheres of calcium carbonate, hydroxyapatite, silica, poly(lactic acid), and poly(glycolic acid). Microbubbles can also be used as ultrasonic imaging contrast agents, as is known in the imaging art. The ultrasonic imaging contrast agents for use in connection with the present invention are preferably biocompatible and stable in the formulation. Concentrations of the ultrasonic imaging contrast agents typically range from about 0.01 wt % to 10 wt % of the formulation, more typically about 0.05 to 2 wt %, where solid particles are used.

For contrast-enhanced MRI, a suitable contrast agent has a large magnetic moment, with a relatively long electronic relaxation time. Based upon these criteria, contrast agents such as Gd(III), Mn(II) and Fe(III) can be used. Gadolinium (III) has the largest magnetic moment among these three and is, therefore, a widely-used paramagnetic species to enhance contrast in MRI. Chelates of paramagnetic ions such as Gd-DTPA (gadolinium ion chelated with the ligand diethylenetriaminepentaacetic acid) also are suitable. Further information can be found, for example, in U.S. Patent Application No. 2003-0100830 entitled "Implantable or insertable medical devices visible under magnetic resonance imaging," the disclosure of which is incorporated herein by reference.

The collagenase formulations described here preferably are injected into one or more individual uterine fibroid tumors using a hollow delivery channel, such as a hollow needle or cannula. For instance, administration can be performed using a needle in association with a conventional or specially designed syringe, cannula, catheter, and the like. A source of manual, mechanical, hydraulic, pneumatic or other means to apply pressure (e.g., a conventional syringe plunger, a pump, aerosol, etc.) can be used to inject the formulation into the fibroid. One example of a suitable needle is a vitrolife needle (oocyte retrieval). Alternatively, the formulations can be administered during surgery, for example via a trocar during laparoscopic surgery and during hysteroscopic treatment.

Injection routes include, for example, transabdominal, transcervical and transvaginal routes. Where the formulations have fluid attributes, the injection volume will vary, depending, for example, on the size of the fibroid, the type and concentration of treatment agent, and so forth, and will typically range from about 0.01 to about 10 ml per injection, preferably about 0.025 ml to about 1 ml, most preferably about 0.05 to about 0.1 ml. Similarly, where formulations having solid attributes (e.g., pellets or powders) are used, the amount of formulation injected/inserted will also depend, for example, on the size of the fibroid, the type and concentration treatment agent utilized, etc. Multiple pellets or doses of collagenase composition can be administered at a single injection site. Regardless of the physical attributes of the formulation, multiple injection/insertion sites may be established within a single fibroid, with the number of injections depending on the size and shape of the fibroid as well as the type and/or concentration of the treatment agent that is used. Multiple fibroids or a single fibroid can be treated.

In various embodiments, the injection/insertion device is guided to the fibroid site under image guidance. Image guidance can include, for example, direct visual guidance (e.g., laparoscopic guidance in trans-abdominal procedures and hysteroscopic guidance in trans-vaginal procedures) and non-direct visual guidance (e.g., ultrasound guidance, fluoroscopic guidance, and/or MRI guidance).

As a specific example, visual guidance of the injection/insertion device is conducted laparoscopically using a scope that is positioned in the abdomen (e.g., by insertion through a trocar). In this way, a device (e.g., a delivery needle or canula) can be inserted percutaneously into the abdomen and guided under laparoscopic vision to the uterine fibroid. Once the fibroid is reached, fluoroscopy, MRI or ultrasound (e.g., trans-vaginal ultrasound, trans-abdominal ultrasound, intra-abdominal ultrasound, etc.; Hitachi) preferably is used to guide the tip of the delivery needle to a desired position within the fibroid, at which point the formulation is injected or inserted into the fibroid. To the extent that there is sufficient contrast between the formulation and the surrounding tissue, the location of the formulation within the fibroid will also be viewed.

In yet more detail, the present invention is described by the following items which represent preferred embodiments thereof:

1. A method for treating uterine fibroids in a patient comprising administering into the uterine fibroid a composition comprising *Clostridium histolyticum* collagenase.
2. The method of item 1, wherein said composition is delivered through a delivery channel into said fibroid, wherein the delivery channel is in a needle, syringe, cannula, catheter or jet injector.
3. The method of item 1, wherein the collagenase is a mixture of collagenase I and collagenase II.
4. The method of item 1, wherein the collagenase is bacterial.
5. The method of item 4, wherein the collagenase is from *Clostridium histolyticum*.
6. The method of item 1, wherein about 0.005 mg to about 10 mg collagenase is administered per $cm^3$ of tissue to be treated.
7. The method of item 1, wherein about 0.05 mg to about 1 mg collagenase is administered per $cm^3$ of tissue to be treated.
8. The method of item 1, wherein about 0.25 mg to about 1 mg collagenase is administered per $cm^3$ of tissue to be treated.
9. The method of item 1, wherein treatment is assessed by measuring fibroid size, volume, or stiffness.
10. The method of item 1, wherein treatment is assessed by measuring collagen content.
11. The method of item 1, wherein treatment is assessed by assessing apoptosis in the fibroid.
12. A method for treating symptoms associated with uterine fibroids comprising administering into the uterine fibroid in the patient a composition comprising *Clostridium histolyticum* collagenase.
13. The method of item 12, wherein said composition is delivered through a delivery channel into said fibroid, wherein the delivery channel is in a needle, syringe, cannula, catheter or jet injector.
14. The method of item 12, wherein the collagenase is a mixture of collagenase I and collagenase II.
15. The method of item 12, wherein the collagenase is bacterial.
16. The method of item 15, wherein the collagenase is from *Clostridium histolyticum*.
17. The method of item 12, wherein about 0.005 mg to about 10 mg collagenase is administered per $cm^3$ of tissue to be treated.
18. The method of item 12, wherein about 0.05 mg to about 1 mg collagenase is administered per $cm^3$ of tissue to be treated.
19. The method of item 12, wherein about 0.25 mg to about 1 mg collagenase is administered per $cm^3$ of tissue to be treated.

20. The method of item 12, wherein the symptom is pain, bloating, pressure, bleeding, pre-term labor.
21. The method of item 20, wherein the symptom is pain.
22. The method of item 21, wherein the pain is measured by McGill Pain Scale.
23. The method of item 21, wherein the pain is measured by Visual Analogue Scale for Pain.
24. The method of item 21, wherein the pain is measured by uterine fibroid symptom quality of life questionnaire (UFS-QoL).

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

EXAMPLES

Example 1. General Collagenase Production

To prepare an animal-material-free Clostridia cell bank, *Clostridium histolyticum* cells are suspended in a medium containing a vegetable peptone and optionally yeast extract. For example, one general method for accomplishing this is as follows.

TABLE 2

General Method to Produce Clostridium Cell Bank.

| Step 1 | Starting cells: any *Clostridium histolyticum* culture which is convenient and available, for example *Clostridium histolyticum* ATCC 21000, strain 004 |
| Step 2 | Inoculate 1 mL of step 1 into 300 mL of media containing 15.45 g Phytone, 2.55 g yeast extract, and water sufficient to produce 0.3 L (M#1); |
| | step 2 for 24 hours at 37° C. ($1^{st}$ culture); |
| Step 4 | Transfer 3 mL of step 3 ($1^{st}$ culture) to 1000 mL of M#1; |
| Step 5 | Incubate step 4 for 16 hours at 37° C. ($2^{nd}$ culture); |
| Step 6 | Centrifuge the $2^{nd}$ culture; |
| Step 7 | Re-suspend the pellet with the 5 mL of media #1 and 5 mL of 20% glycerol; |
| Step 8 | Freeze the aliquot of cells gradually; |
| Step 9 | Store the aliquot at −80° C. |

Once an animal material-free cell bank is established, the cells can be grown or fermented in convenient media known in the art, preferably non-animal-derived medium. The medium can optionally contain yeast extract. Exemplary, nonlimiting examples of such media are M #1, M #2, M #3, and M #4 as described in Table 3, below. In addition, see Table 4 for an exemplary, non-limiting general example of the steps of the fermentation process.

TABLE 3

Media recipes and preparation.

| | M #1 | M #2 | M #3 | M #4 |
|---|---|---|---|---|
| Phytone | 15.45 g | | 103 g | |
| Veggitone | | 15.45 g | | 103 g |
| Yeast extract | 2.55 g | 2.55 g | 17 g | 17 g |
| KH2PO4 | | | 1.92 g | 1.92 g |

TABLE 3-continued

Media recipes and preparation.

| | M #1 | M #2 | M #3 | M #4 |
|---|---|---|---|---|
| K2HPO4 | | | 1.25 g | 1.25 g |
| Na2HPO4 | | | 3.5 g | 3.5 g |
| NaCl | | | 2.5 g | 2.5 g |
| vol of water | 0.3 L | 0.3 L | 1 L | 1 L |

TABLE 4

Fermentation Process.

| Step 1 | Starting cells: Animal material free Clostridia cell bank |
| Step 2 | Inoculate 1 mL of step 1 into the 300 mL of M#1; |
| Step 3 | Incubate step 2 for 16 to 24 hours at 37° C. ($1^{st}$ culture); |
| Step 4 | Transfer 10 mL of step 3 ($1^{st}$ culture) and 10 mL Vitamin/Mg solution* to 1000 mL of M#3, or 4 respectively; |
| Step 5 | Incubate step 4 for about 22 hours at 37° C. ($2^{nd}$ culture); |
| Step 6 | Use $2^{nd}$ culture for downstream isolation and purification. |

*Prepared separately by dissolving 8 g MgSC>4, 1.2 g ferrous sulfate, 0.05 g riboflavin, 0.1 g Niacin, 0.1 g Calcium pantothenate, 0.1 g pimelic acid, 0.1 g pyridoxine, and 0.1 g thiamine in 1100 mL water, followed by sterilization by 0.22 urn filtration.

After preparation of "$2^{nd}$ culture," the collagenase I and collagenase II can be isolated and purified using any method capable of producing each enzyme separately to at least 95% purity. The method may combine one or more of the steps of ammonium sulfate precipitation, dialysis, hydroxyapatite (HA) chromatography, gel filtration and ion-exchange, for example, preferably in that order. The gel filtration is preferably G75 gel filtration. The ion-exchange is preferably anion-exchange: Q-Sepharose chromatography. In addition, when the Clostridia have been cultured in medium containing less glucose and more salt compared to the majority of known bacterial culture, as preferred, protease inhibitors such as leupeptin are not required.

Example 2. Preparation of Animal Material Free *Clostridium* Cell Bank

The starter cell culture was *Clostridium histolyticum* ATCC 21000, strain 004 which was originally created with bovine-derived materials. The cells were first grown in animal material free medium (M #1, Table 3). Briefly, the recipe includes: phytone, 51.5 g, yeast extract 8.5 g, 1000 mL water. The pH was adjusted to 7.30 with NaOH, and the medium sterilized at 121° C. for 20 minutes. One milliliter of the starting material was then inoculated into 300 mL of M #1 and incubated for 24 hours at 37° C. (1st culture). Three milliliters of the 1st culture was transferred to 1000 mL of M #1 and incubated for 16 hours (2nd culture). The 2nd culture was then centrifuged aseptically. The pellet was re-suspended in 5 mL M #1 with 5 mL 20% glycerol. The aliquots of cell suspension were frozen gradually and stored at −80° C.

Example 3. Fermentation Process

*Clostridium histolyticum* ATCC 21000, strain 004 was inoculated into the starting culture with M #1 or M #2 and incubated at 37° C. for 16 hours. Ten milliliters of the starting culture (M #1 or M #2) and 10 mL Mg/vitamin solution (prepared separately by dissolving 8 g MgSO4, 1.2 g ferrous sulfate, 0.05 g riboflavin, 0.1 g Niacin, 0.1 g Calcium pantothenate, 0.1 g pimelic acid, 0.1 g pyridoxine, and 0.1 g thiamine in 1100 mL water, followed by sterilization by 0.22 pm filtration) was then transferred to each liter of M #3 or M #4 (or a variation thereof), and incubated for 22 hours. *Clostridium histolyticum* grew well with the OD600 reaching >2.5.

Example 4. General Procedure for Isolation and Purification of Collagenase I and Collagenase II

TABLE 5

General Exemplary, Non-Limiting Isolation and Purification Procedure for Collagenase I and Collagenase II.

| Stages of Product | Operations |
|---|---|
| Fermentation broth | Centrifugation or 1.0 pm filtration; |
| Clarified fermentation broth | Add ammonium sulfate (590 g/liter); centrifugation; |
| Crude collagenase precipitate | Dissolve crude collagenase precipitate by adding purified water; |
| Crude collagenase solution (store at −20° C.) | Dialyze crude collagenase solution against purified water overnight with 10 kDa pore size dialysis membrane; |
| Dialyzed crude collagenase | Clarify the dialyzed crude collagenase solution with either centrifugation or filtration or the combination of both; |
| Clarified solution | Add potassium phosphate buffer, pH 6.7 to a final cone, of 0.1M; |
| Collagenase in phosphate buffer | Load collagenase solution to hydroxylapatite column and elute column with gradient of increasing $K_2PO_4$ cone, at ambient temp. (20° C.); |
| Collagenase HA eluate | Concentrate the eluate with ultrafiltration (30 kDa of pore size); |
| Concentrated collagenase | Load the concentrate onto a G75 gel filtration column at ambient temperature (20° C.) and elute with 20 mM Tris/150 mM NaCl; |
| Collagenase G75 eluate | Dialyze the eluate against a buffer (10 mM Tris, 3 mM calcium chloride (CaCL), pH 8.0) overnight; |
| Dialyzed G75 eluate | Load dialyzed eluate on to a Q-Sepharose anion-exchange column at ambient temperature (20° C.); elute using a gradient of 10 mM Tris HCl, 3 mM CaCL, pH 8.0 buffer and 10 mM Tris HCl, 3 mM CaCL, 1M NaCl, pH 8.0 buffer; |
| Collagenase class I and class II fractions | Store separately at −20° C. |

Example 5. Ex Vivo Treatment of Uterine Fibroid Tissue

Samples of fibroid tissue and myometrium were obtained posthysterectomy from women with consent and identified by evaluation by a surgical pathologist. The tissue samples were transported to the laboratory and cut into 1 $cm^3$ cubes. See FIG. 2 of U.S. Pat. No. 10,369,110. These cubes were injected with purified collagenase (0.06 or 0.2 mg in 100 pL) dissolved in media or serum and then incubated for 24, 48, 72, or 96 hours at 37° C. See FIG. 3 of U.S. Pat. No. 10,369,110. Each treatment was carried out in tissues from three different patients with two tissue samples per treatment because fibroid tissue is extremely variable. Control fibroid and myometrium cubes were injected with vehicle or sham injected. At the end of the incubation, the tissue samples were photographed to document gross appearance. Degree of liquefaction and softening was observed and documented using a 4-point subjective scale.

Samples were frozen for biomechanical assessment (compression analysis). Samples were fixed in formalin for histology and Masson trichrome and picrosirius red staining. They were analyzed by light microscopy for the presence or absence of collagen and assessed using computer morphometry to determine the extent of degradation. In the case of picrosirius red staining, polarized light microscopy was performed to determine collagen fiber orientation. Samples were fixed in glutaraldehyde and postfixed with osmium tetraoxide for electron microscopy to determine collagen fibril orientation and evidence of fibril degradation. Additional injections were done at a dose of 0.58 mg/injection (250 fil of 2.3 mg/ml).

These ex vivo studies have shown the efficacy of purified collagenase in softening and partial liquefaction of post-hysterectomy fibroid specimens, as well as a decrease in the collagen content. Treated fibroid-specimens were grossly softer and had partially liquefied centers. Masson trichrome and picrosirius red stains of theses tissues showed a dramatic subjective decrease in collagen content compared to fibroid tissue injected with vehicle.

Example 6. Treatment of Whole Uterine Fibroids Ex Vivo

Donated tissue was obtained from four female adult patients 18 years of age or older who can give legally effective consent and who were planning to undergo definitive treatment for fibroids by hysterectomy. After the removal of the hysterectomy specimen, the uterus was observed grossly by standard procedures by a surgical pathologist. Complete fibroids (submucosal (abutting the endometrium), intramural (within the myometrium), and subserosal (abutting the uterine serosa) fibroids, or pedunculated fibroids (attached to the uterus by a stalk) if they are present) from 1 to 4 cm (including the capsule) along with 1.5 cm of the surrounding adjacent myometrium and, if available, a 0.5 cm section of endometrium were dissected free from the specimen and placed in normal saline.

Tissues were brought to the laboratory immediately, washed and injected with purified *Clostridium histolyticum* collagenase (PCHC) (0.1 mg/100 pl/$cm^3$). Optionally, a higher concentration of the collagenase was used to decrease the volume of the injection. Purified collagenase was diluted in 0.3 mg/mL calcium chloride dihydrate in 0.9% sodium chloride, optionally combined with 1% methylene blue as a marker to visually assess the area of distribution of the injected material within the fibroid and uterus. Fibroids were injected with PCHC or vehicle in the center of the obtained specimen. See FIGS. 4A and 4B of U.S. Pat. No. 10,369,110. The amount of collagenase injected depended on the size of the fibroids (1-4 cm).

Generally, about 818 pL of material was injected into a fibroid with a diameter of about 2.5 cm. If injecting the entire treatment volume centrally was not feasible due to tissue resistance to the injection or other factors, multiple locations were injected within the fibroid. The fibroid tissue then was incubated in DMEM/F12 culture medium at 37° C. for 24 hours. At least one fibroid with attached myometrium served as the control. This specimen received an injection of 1% methylene blue in vehicle without collagenase as a non-randomized placebo injection, centrally into the fibroid.

Color photographs were taken of the uterus and of the fibroid and myometrial pieces pre- and post-injection. Fibroid diameters were measured with a metric ruler.

At the end of the incubation, the samples were reassessed grossly for size, consistency and firmness, and color photographs were obtained, as well as optional video recording to record fibroid manual distensibility and any liquefied portions upon sectioning. The degree of liquefaction and softening were observed and documented using a 4-point subjective scale.

Whether the collagenase can penetrate the capsule and affect the nearby myometrium was determined. Samples were obtained, including tissue from the injected fibroid and adjacent tissue, plus a section that included fibroid and adjacent myometrium and/or endometrium still attached, and myometrium alone. Samples were fixed in formalin for histology and Masson trichrome, picrosirius red, and hematoxylin-eosin staining. The samples were analyzed by light microscopy for the presence or absence of collagen and using computer morphometry to assess the extent of degradation. Picrosirius red staining was used with polarized light microscopy to determine collagen fiber orientation.

Figure 5:
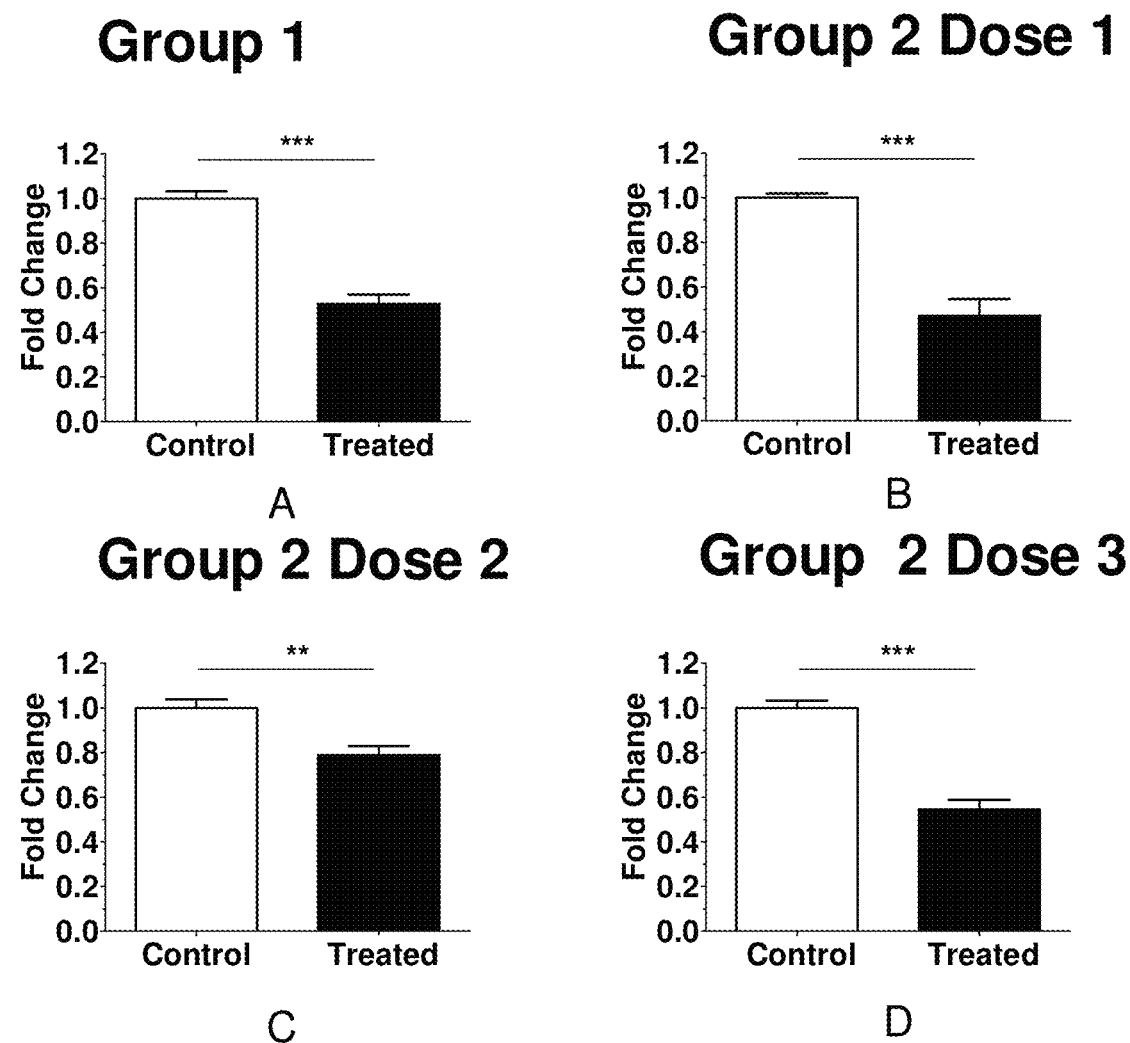
FIG. 5. Changes in collagen content among tissues summarized for each of the four study groups. To assess for possible dose-dependent effects, a grouped analysis was performed for the control and injected fibroid tissues. Analysis and data are those shown in FIG. 4, but combined and displayed with their respective study group allocation. Fold change represents reduction in collagen between control (set at 1.0) and injected samples. (A) Group 1, (B) Group 2 Dose 1, (C) Group 2 Dose 2, (D) Group 2 Dose 3. *p<0.05, p<0.01 and *p-value<0.001 (unpaired T-test)

Exemplary treatment schemes for each patient:
fibroid 1: inject 818 pL 1 mg/mL collagenase;
fibroid 2: inject 818 pL 1 mg/mL collagenase;
fibroid 3: inject 818 pL control vehicle;

Injections were given through the fibroid capsule into the center of the fibroid, through the myometrium into the center of the fibroid, or through the endometrium into the center of the fibroid, simulating in vivo injection routes. The fibroids here were liquefied in the same manner as shown in FIG. 5 of U.S. Pat. No. 10,369,110 (see below).

Example 7. Biomechanical Evaluation of Human Uterine Fibroids after Injection with Purified Clostridial Collagenase The two collagenases isolated from *Clostridium histolyticum* (ABC I and ABC II) were combined in a 1:1 mass ratio. Both collagenases are metalloproteases and have a broad hydrolyzing reactivity and degrade type I and III collagens. The biomechanical properties of uterine fibroid tissue were analyzed by rheometry in control and collagenase-treated specimens.

Uterine fibroids have been shown to contain about 70% Type I collagen compared to about 80% in myometrium; about 28% Type III collagen compared to about 20% in myometrium; and about 5% Type V collagen compared to about 2% in myometrium. Type I/III is lower at the center and the edge of fibroids as compared to myometrium.

Fibroid tissue was obtained after surgery (hysterectomy or myomectomy) from 4 different patients and cut into cubes (1 cm$^3$; n=43). Tissue cubes were injected into the center with 100 pL of purified collagenase (0, 0.25, 0.5, 1.0, 2.0 mg/mL; n=414 per dose) and incubated at 37° C. for 24, 48, or 96 hours. At the end of the incubation period, cubes were cut in half and snap-frozen in liquid nitrogen. Different degrees of softening and liquefaction at the center were noted. An AR-G2 rheometer was used to measure the sample stiffness dynamically (complex shear modulus (Pa) at 10 rad/sec), taking into account both the viscous and elastic behavior of the material. At least 2 specimens (5 mm diameter punch) from each tissue cube were measured. Data were analyzed by 2-way ANOVA and Dunnett's multiple comparisons test.

Overall, stiffness in control fibroid cubes (6585±707 Pa; n=13) was greater than in treated cubes (2003±275 Pa; n=30; $p<0.0001$). More specifically, stiffness in fibroid tissues was reduced in a time and dose dependent manner. At 48 hours, treatment with 0.25 mg/mL did not reduce stiffness (5032±1796 Pa), but treatment with mg/mL did (2014±1331 Pa; $p<0.05$). At 96 hours, both the 0.25 and the 0.5 doses were effective (1720±377 and 1072±160 Pa; $p<0.01$). The 1.0 and 2.0 mg/mL treatments reduced stiffness at 24 hours, but not significantly (2177±37 and 2480±984 Pa; n=4). However, doses of 1.0 and 2.0 mg/mL were effective at 48 hours (3588±637; $p<0.05$ and 1254±445 Pa; $p<0.01$; n=6;) and at 96 hours (921±305 and 1350±571 Pa; $p<0.0001$; n=10).

Figure 6:
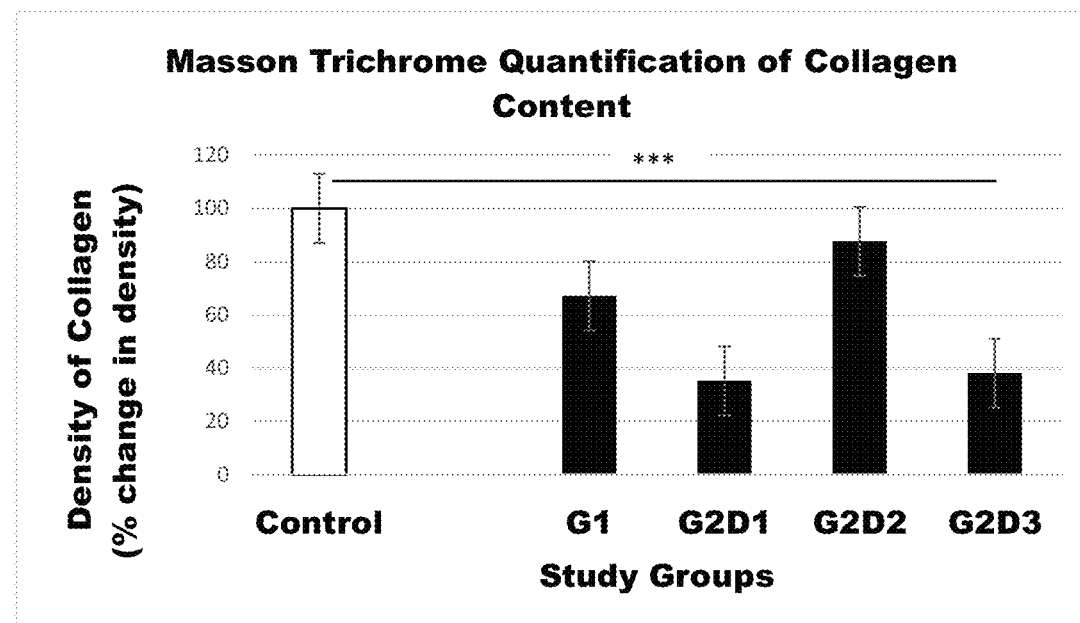
FIG. 6. Changes in collagen content compared between a pooled control and treated samples of all study groups. Actual density (sum of pixel values) values are plotted in the Y axis and the study groups on the X axis, Controls (pooled data), G1: Group 1; G2D1: Group 2 Dose 1, G2D2: Group 2 Dose 2, G2D3: Group 2 Dose 3. On average there was a 42.9% (range 12.3-64.7%) reduction in collagen content between pooled control and study group samples.

Using a torsional rheometer, tissue stiffness was quantitated over a wide range (very firm to liquefied). Data indicate that treatment of the fibroid tissue with defined doses of purified clostridial collagenase significantly decreased the stiffness (modulus) of the tissue. See FIG. 5 of U.S. Pat. No. 10,369,110, which shows collagenolysis in fibroid tissue after 48 hour incubation. The left photograph is tissue that was injected with vehicle (control) and the right photograph is tissue that was injected with collagenase. FIG. 6 of U.S. Pat. No. 10,369,110 shows micrographs of control (FIGS. 6A and 6B) and collagenase-treated (FIGS. 6C and 6D) tissue. Mason stain in Figures A and C (left) shows that collagen is decreased. Picrosirus red stain visualized under polarized light (FIG. 6D) clearly shows in the bottom right that collagen fibers are degraded.

Example 8. Treatment of Human Uterine Fibroids in Nude Mouse Model

The xenograft mouse model, in which three-dimensional organotypic cultures of human uterine fibroid cells are implanted under the skin of female nude mice, has been successfully employed to study keloids, a fibrotic skin disorder with biology similar to fibroids. This model is used to demonstrate effects of PCHC injection, in an HPG nanocarrier formulation, on fibroid tissue in vivo.

Polylactic acid sponges, other synthetic polylactic acid scaffolds, or any suitable commercially available scaffold is inoculated with human uterine fibroid cells to produce an organotypic 3-D culture of uterine fibroid cells that can be implanted into nude mice. These 3-dimensional organotypic cultures (3D-fibroids) are representative of human fibroids and produce and contain extracellular matrix.

Figure 7:
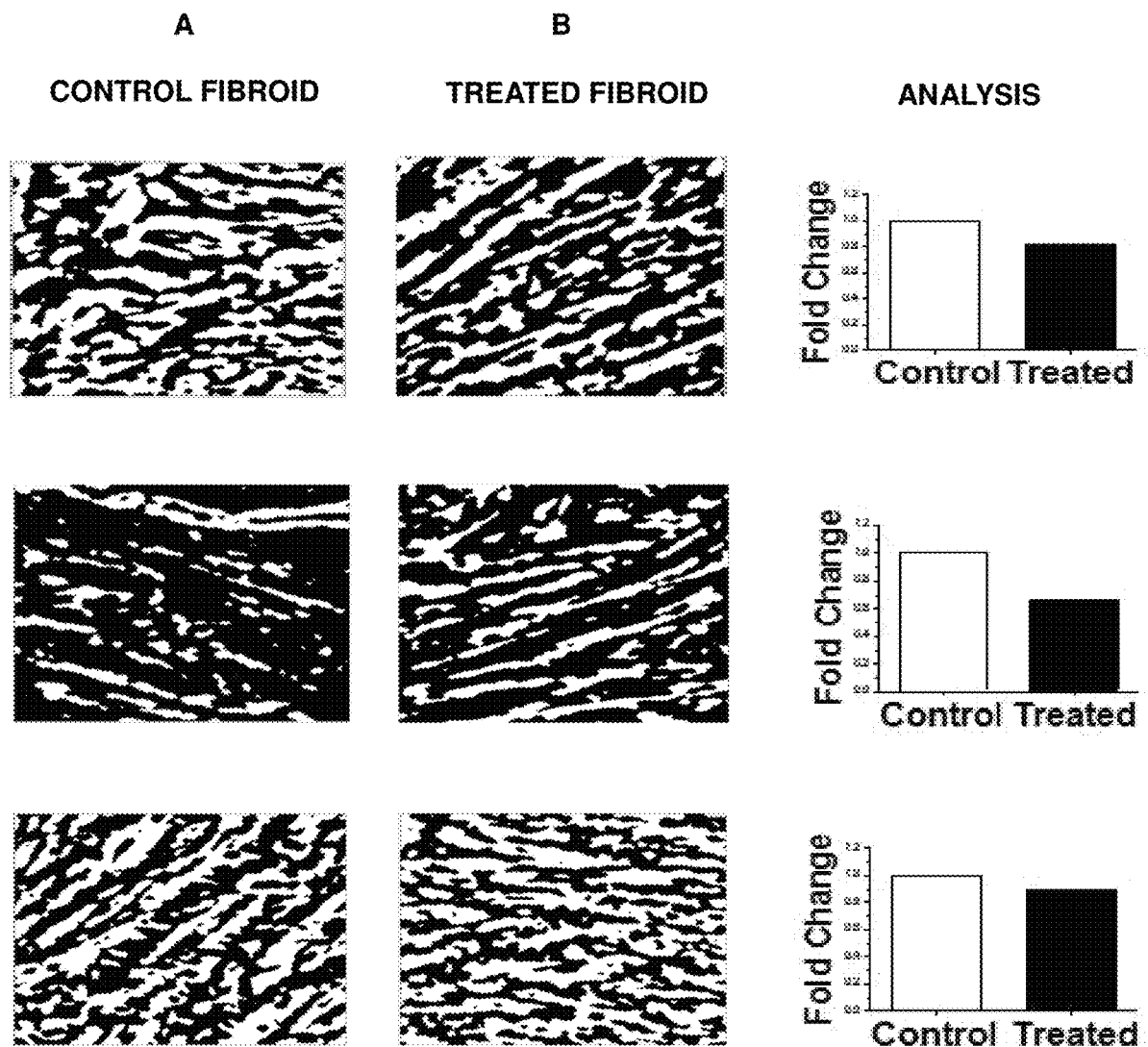
FIG. 7: Second Flarmonic Generation Imaging of the fibroid tissues for collagen distribution. A: Control fibroids; Treated fibroids, B. Fold change in collagen distribution as measured by Image J software, change in density of collagen fiber distribution was measured in pixels. (N=3)

OPLA® sponges (Open-Cell Polylactic Acid, BD Biosciences; FIG. 7 of U.S. Pat. No. 10,369,110) are synthetic polymer scaffolds that are synthesized from D,D-L,L polylactic acid. This material has a facetted architecture which is effective for culturing high density cell suspensions. The cells will be seeded onto the 3D spongelike scaffolds under dynamic conditions, leading to uniform cell population throughout the sponges and higher cell numbers per sponge than static seeding. Post-sterilization, the molecular weight of the OPLA® is 100-135 kD. They have an approximate size of 5 mm×3 mm (0.04 cm$^3$) with an average pore size of 100-200 pm.

Cells and scaffolds are placed into cell culture chambers of a bioreactor consisting of a fluid (culture media)-filled, rotating chamber that allows for constant floating of cells while minimizing shearing forces and gravitational settlement of cells and/or scaffolds (Synthecon, Inc.). Cells inside the rotating bioreactor chamber are suspended in virtual weightlessness.

Primary human fibroid cells from specimens obtained at hysterectomy are seeded statically or dynamically into OPLA® sponges and grown for 30 days to allow for production and assembly of extracellular matrix. Cells grow throughout the scaffold and can be formalin fixed, paraffin embedded and thin sectioned for observation, optionally with staining for multiple markers. See FIG. 8 of U.S. Pat. No. 10,369,110, which shows the formation of the cell lattice following the outlines of the sponge-like scaffold.

Figure 9:
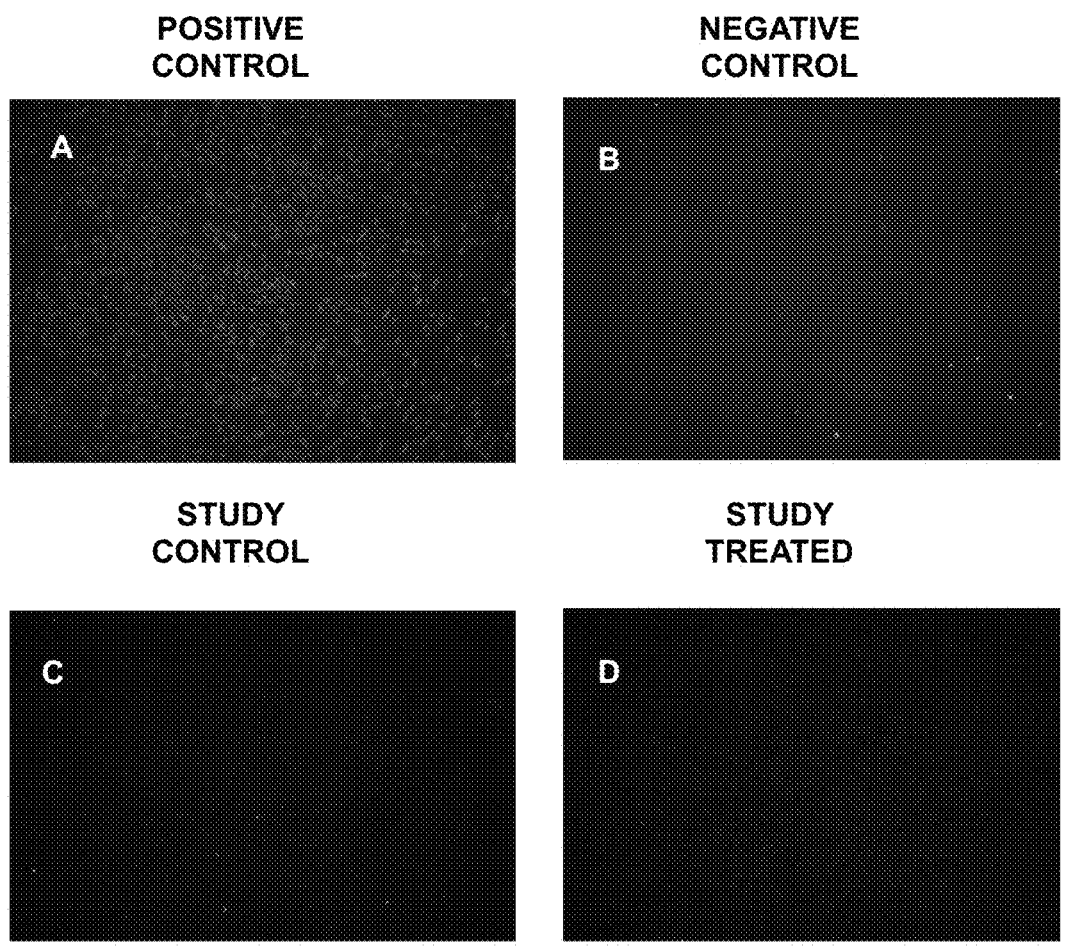
FIG. 9. TUNEL Assay to detect apoptosis. No increase in apoptosis was identified in the treated fibroid samples collected post hysterectomy. Image A: Positive Control, Image B: Negative Control, Image C: Study Control and Image D: Treated Sample. (N=12, one representative image shown)

FIG. 9 of U.S. Pat. No. 10,369,110 shows primary cultures of fibroid cells after static seeding. The cells are fixed on the scaffold and observed in situ. Scaffolds containing cells were fixed and were unstained (FIG. 9A) or stained for f-actin with fluorescent phalloidin (FIG. 9B). Cells were evenly distributed throughout the scaffold. The imaged scaffolds are >1 mm thick and therefore not all cells are in focus, indicating that the cells are growing not only on the surface, but also deep inside the scaffolds. FIG. 10 of U.S. Pat. No. 10,369,110 shows the population of cells throughout the sponge-like scaffolds using confocal microscopy (FIGS. 10A and 10B).

OPLA® sponges and used to verify the expression of two genes of interest. Versican and TGFβ3 are known to be highly expressed in fibroid tissue and cells. Results in Table 6 show that both a fibroid cell line and primary cultures of fibroid cells in this 3D-culture system express these two genes in high amounts.

TABLE 6

Real Time PCR Assay Results

| | cDNA (ng) per reaction | Threshold Cycle Ct (mean ± SEM) | |
|---|---|---|---|
| | | Versican | TGFβ3 |
| Fibroid Cell Line | 50 | 22.1 ± 0.07 | 26.8 ± 0.07 |
| Primary Fibroid Cells | 25 | 22.2 ± 0.21 | 24.0 ± 0.04 |

Example 9. Treatment of Uterine Fibroids In Vivo

Uterine leiomyomas or fibroids are the most common benign tumors of the female reproductive system and pose a significant problem for millions of women. (Baird et al. 2003). By age 50, uterine fibroids are diagnosed in more than 80% of African American and 70% of Caucasian women. (Drayer et al. 2015). The estimated direct annual costs of medical and surgical management for fibroids range from approximately 4 to 9 billion USD. (Cardozo et al. 2012).

Fibroids are tumors of smooth muscle cells. Flowever, multiple studies show that the bulk of these tumors is composed of an extracellular matrix (ECM) mostly consisting of disorganized, altered, highly cross-linked collagen fibers. (Flake et al. 2013, Berto et al. 2003, Behera et al. 2007, Catherino et al. 2004, Leppert et al. 2004). The ECM component of the fibroid has a direct effect on tumor growth by induction of fibrosis that leads to a decreased rate of apoptosis and increased collagen deposition. (Leppert et al. 2014, Norian et al. 2012). Untreated fibroids are collagen-rich with fibrosis ranging from 37%-77%. After ex vivo treatment with collagenase for 96 hours, fibrosis ranged from 2.4% to 5.3%. (Jayes et al. 2016). The reduction was associated with a decrease in tissue stiffness and loss of collagen fibers in treated fibroids as compared to control tissues. (Jayes et al. 2016, Brunengraber et al. 2014).

Purified collagenase *Clostridium histolyticum* (EN3835) was FDA-approved for the treatment of Dupuytren's contracture by local injection in 2010 and for Peyronie's disease in 2013. (Thomas and Bayat 2010, Badalamente and Hurst 2007, Glbard et al. 2013). EN3835 consists of collagenases of classes I and II with a potent binding affinity to interstitial collagens, especially collagens I and III. Class I EN3835 has an especially high affinity to mature triple helical interstitial collagen at the N and C termini with a preferred cleavage site. Class II EN3835 cleaves the inner peptides and its preferred substratum is small denatured peptides. (Han et al. 2010, Bromley et al. 1980, Friedman et al. 1986, Mallya et al. 1992, Miyabashi et al. 1992, Toyoshima et al. 2001). The extracellular matrix in a fibroid is abundantly composed of collagens type I, Ill, and V, making fibroids a logical target for EN3835. (Leppert et al. 2014). Notably, EN3835 digests types I and III collagens which are abundant in fibroids (Norian et al. 2012, Toyoshima et al. 2001) but does not degrade the type IV collagen found in the basement membranes of the nerves and blood vessels. (Thomas and Bayat 2010, Badalamente and Hurst 2007). This is important as fibroids can be highly vascularized. Furthermore, EN3835 is inhibited by serum proteins and is rapidly degraded in the circulation. (Badalamente and Hurst 2007, Borth et al. 1981, Nagase et al. 1994). These features were confirmed in clinical trials for Peyronie's disease. After treatment, antibodies directed against EN3835 I and II were detected in serum, however, no adverse effects were noted. (Thomas and Bayat 2010, Badalamente and Hurst 2007).

Evidence from minimally invasive therapies currently available for uterine fibroids, such as uterine artery embolization or uterine fibroid ablation using MR-guided focused ultrasound, support the tenet that reduction in fibroid size can translate into a reduction in fibroid-related symptoms. (Munro 2011, Taylor and Leppert 2012, Sabry and Al-Hendy 2012, Chudnoff et al. 2013). The present study was performed to assess whether by digesting the ECM of fibroids, the subsequent debulking of the tumor results in reduced fibroid symptoms such as pain or bleeding. (Norian et al. 2012, Brunengraber et al. 2014).

The aim of this study was to explore the safety and tolerability of using collagenase *Clostridium histolyticum* (EN3835) in human subjects with symptomatic uterine fibroids. With regard to safety, several issues were kept in mind. For example, bowel injury from the injection technique was avoided by patient position (lithotomy). Inadvertent peritoneal exposure was avoided by ultrasound guidance. Vascular injection was avoided using doppler sonography. Retention of drug in the fibroid was confirmed with ultrasound visualization. Fibroid resistance to effective insertion of the needle into the fibroid was shown to not be an issue where fibroids were injected with a clear path.

Results show that safe and tolerable treatment of clinically-relevant leiomyomas with collagenase EN3835, a non-hormonal treatment, is feasible and reduces the collagen content of the fibroids, thus affording patients a new minimally invasive option for fibroid treatment.

Materials and Methods

Study Design

This was an open-label, dose-escalation study of EN3835 in women with symptomatic uterine fibroids undergoing hysterectomy at Johns Flopkins Hospital, Baltimore, MD, USA. The Institutional Review Board at Johns Flopkins School of Medicine approved the study protocol and all procedures. All study drug injections were performed by Dr. James Segars with ultrasound assistance provided by Dr. Bhuchitra Singh at the Johns Flopkins Outpatient Center Surgery Center. This was a pilot study with a sample size of 15. This study was conducted in accordance with US and international standards of Good Clinical Practice (FDA Title 21 CFR part 312 and International Conference on Flarmonization guidelines), applicable government regulations, and institutional research policies and procedures.

The safety and tolerability of EN3835 was evaluated using a stepwise approach for the administration of the study drug (FIG. 1). The three subjects in the Saline-only Group (n=3) were injected with normal saline and methylene blue, immediately prior to their hysterectomy. This served as the feasibility group for the injection procedure and drug delivery. Group 1 (n=3) was the fixed dose group; all three subjects received 1.16 mg of the study drug 24-48 h prior to hysterectomy. This dose was selected based on previously approved dosing in Dupuytren's disease. Group 2 (n=9) was further divided into three subgroups (n=3/subgroup), each receiving a higher dose of the study drug than the last subgroup (1.68, 3.35, and 5.028 mg, respectively, as the maximum doses). Each subgroup included three subjects who underwent hysterectomy 60-90 days post study drug injection.

Injected fibroids were collected post hysterectomy and gross examination was performed. The fibroid samples collected at hysterectomy were assessed for collagen content and distribution, percentage change of collagen content by histology stains, and apoptosis by TUNEL staining.

Study Subjects

Recruitment occurred through referrals from gynecologists and radio advertisements. The discussion for enrollment was deferred until the women made an independent decision with their gynecologist to undergo surgical management for fibroids such as hysterectomy or myomectomy. Patients who expressed interest and qualified per study criteria signed the consent form to be enrolled in the study.

Inclusion and Exclusion Criteria

Women aged 35-50 years-old with symptomatic uterine fibroids, with at least one typical intramural fibroid with diameter 3-10 cm, who had completed child bearing and were willing to practice contraception throughout the duration of the study were included in the study. Estrogen and progesterone levels were checked for all subjects to confirm pre-menopausal state at the time of study enrollment. Hormonal treatment in the interim until hysterectomy was allowed (only one subject received hormonal treatment while being enrolled in the study). MRI was performed for all study subjects and only those with "typical" fibroids, visualized as hypo-intense on a T-2 weighted MRI scan, were selected. A screening ultrasound with doppler was performed for all study subjects to identify the best route for the study drug injection.

Women with BMI >40 kg/m 2, history of allergic reaction to EN3835, cancer within the past 5 years, abnormal liver function test (>20% elevation), severe anemia (HCT<30), recent rapid growth of fibroids, and type 0 submucosal, pedunculated, and subserosal fibroids were excluded from this study. The subjects were assigned to the next available study group based upon the date of their enrollment in the study and the timing of their hysterectomy.

Study Drug Administration

All subjects received a single injection of either saline (Saline-only Group, n=3) or EN3835 (Groups 1 and 2, n=12) into one intramural fibroid. For the injection, subjects were sedated, positioned in lithotomy position and fibroids were injected. To avoid injury to blood vessels, color flow doppler was used to identify the best route to the center of the selected fibroid. A conventional 17G, 350 mm, conventional single lumen follicle aspiration needle (manufactured by Vitrolife) was used for the study drug injection. All injections were accurately administered within 3-5 centimeters of the vaginal mucosa and all injections were visualized via ultrasound (FIG. 2). The study drug was injected into the center of the fibroid to ensure safe distribution of the study drug and for accurate assessment of collagen content change once the sample was collected post hysterectomy. Slight repositioning was done to ensure localized infusion and delivery of the study drug. The injection took on average between 1.2 to 2 minutes to complete. The entire procedure, including time to sedate and position the subject, required 20-25 minutes. The subjects in Groups 1 and 2 remained at Johns Flopkins for 4 hours post study drug injection to be monitored for possible immediate adverse events, including hypersensitivity reactions. All subjects were assessed at 24 hours post-injection for any untoward effects.

Study Drug Dosage

The first 3 subjects in the study received methylene blue 1% in saline in the OR immediately prior to hysterectomy. The dye was injected to confirm the injection site in the fibroid sample upon inspection of the uterus post hysterectomy. Upon completion of the saline only group, three subjects (Group 1) received 1.16 mg of EN3835, regardless of fibroid size. Most fibroids are spherical in shape, hence the volume of EN3835 was calculated according to the formula of volume of a sphere. Approximately 50-70 microliters was injected for each 1 $cm^3$ fibroid volume, to a maximum volume of 1.676 ml/fibroid regardless of fibroid volume. For Group 2 subjects, using an injection volume of 0.05 $ml/cm^3$ of fibroid volume, doses of study drug delivered per escalation group was 0.05, 0.1 and 0.2 $mg/cm^3$ of the fibroid, but no subject was to receive more than 1.68, 3.35, and 5.028 mg for Dose 1, 2, and 3, respectively, in Group 2. The maximum doses were capped at 2 and 3 folds of dose 1 since this was the first safety study of EN3835 injection into uterine fibroids.

Assessments and Data Analysis

The primary outcomes of this study were to assess the safety and tolerability of EN3835 following a one-time injection directly into a uterine leiomyoma. Changes in collagen content and rates of apoptosis were also assessed. For each subject, the injected (treated) fibroid and one additional non-injected fibroid (control) was harvested post hysterectomy. The samples were hemisected to expose the center of the fibroid, paraffin-embedded, and sectioned in 5-pm slices. Effects on collagen content and distribution were compared between control and treated fibroids using Masson's Trichrome and Picrosirius Red stains. Second Flarmonic Generation (SFIG), a multiphoton electron microscopy technique, directly visualized protein assemblies without use of exogenous labels to extract structural information through polarization and directional resolved methods. 29 SFIG was used to compare collagen organization and distribution between control and treated fibroids.

Collagen content was quantified in Masson Trichrome stained slides of control and treated fibroids from each subject. ImageJ was used to obtain pixel counts representing areas of stained collagen in 9 grids with equal area in the center of each fibroid. (Schindelin et al 2012). Treated and control fibroids were compared within each subject. Flowever, fibroids can be heterogeneous in collagen density and stiffness and the control fibroids may not be representative of other fibroids from the same women. (Jayes et al. 2019). Therefore, additional analysis was performed combining all controls (n=12) to control for the biological variability of fibroids and each treatment group was compared against this pooled control of uninjected patient-matched fibroid samples. TUNEL assay was used to compare rates of apoptosis between control and treated fibroids. Tissue sections incubated with DNase I for 10 minutes at 15-25° C., prior to labeling solution introduction, was used as positive control, and sections incubated with label solution alone was used as negative control.

Patient-Reported Outcomes

Subjects completed study related questionnaires. Part 1 of the Uterine Fibroid Symptom Quality of Life questionnaire (UFS-QOL) specifically evaluated severity of physical symptoms associated with fibroids and part 2 of the UFS- QOL evaluated health-related quality of life associated with fibroids. (Spies et al. 2002, Flarding et al. 2008, Coyne et al. 2018). The McGill Pain Scale questionnaire collected detailed data about the pain associated with fibroids and evaluated the impact on pain from the study drug injection. (Feng et al. 2010, Bouwsma et al. 2011). The Visual Analogue Scale (VAS) for Pain) was used to evaluate fibroid related pain on a 0-10 likert scale (higher score=worse pain). (Giray et al. 2018, Fennessy et al. 2011). The questionnaires were administered at baseline and post study drug injection (Group 1: 24-48 hrs. post study drug injection, 2 weeks post hysterectomy; Group 2: 4-8 days post study drug injection, 60-90 days post study drug injection) to assess their fibroid-related symptoms such as menorrhagia and pain.

Statistical Analysis

The sample size of the study was not designed to detect statistical significance for differences in outcome reported symptoms, but the data were collected to assess trends in safety and tolerability. To compare the changes in outcomes between treatment and control by group, generalized linear mixed effects models with random intercepts for the person and paired t-tests were used (Stata/IC 14.0 and Excel 2013 software); all tests were performed at 0.05 level of statistical significance. The models included treatment groups and their interaction as the primary predictors. Blood samples were collected for pharmacokinetic studies pre-injection and then at 5, 10, 30, 60, and 240 minutes post-injection. Blood samples for anti-AUX I and anti-AUX II, antibodies for EN3835, were collected at baseline and at the last follow up visit at 3 months post hysterectomy for Group 1 and at 60-90 days post study drug injection and 3 months post hysterectomy for Group 2 subjects.

Results

Demographics

Of the 19 patients screened, all of whom planned on hysterectomy, 15 women who met the study's eligibility criteria were enrolled. The average age of the study subjects was 44.7±2.6 years. The ratio of black to white women was 3:2, similar to the epidemiology of fibroids. During the screening visit, a detailed medical history and concomitant medication review, physical exam with pelvic exam, and laboratory blood test were performed to ensure eligibility. The baseline characteristics of the 15 subjects are presented in FIG. 10.

Gross Fibroid Exam

Figure 2A:
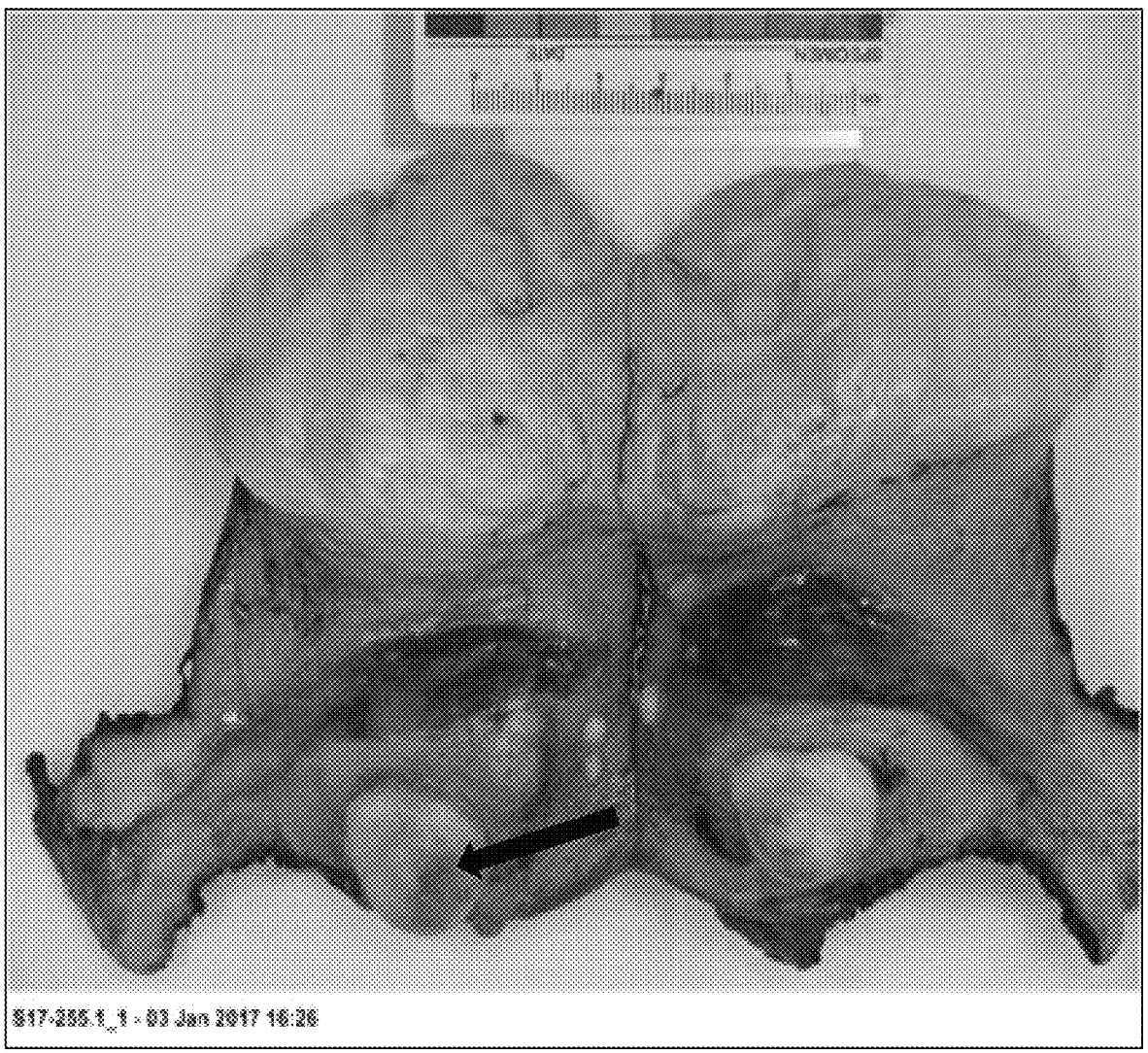
FIG. 2a. Representative image of the fibroids injected in the Saline only group. The black arrow points to the methylene blue injected into the center of the fibroid.
Figure 3:
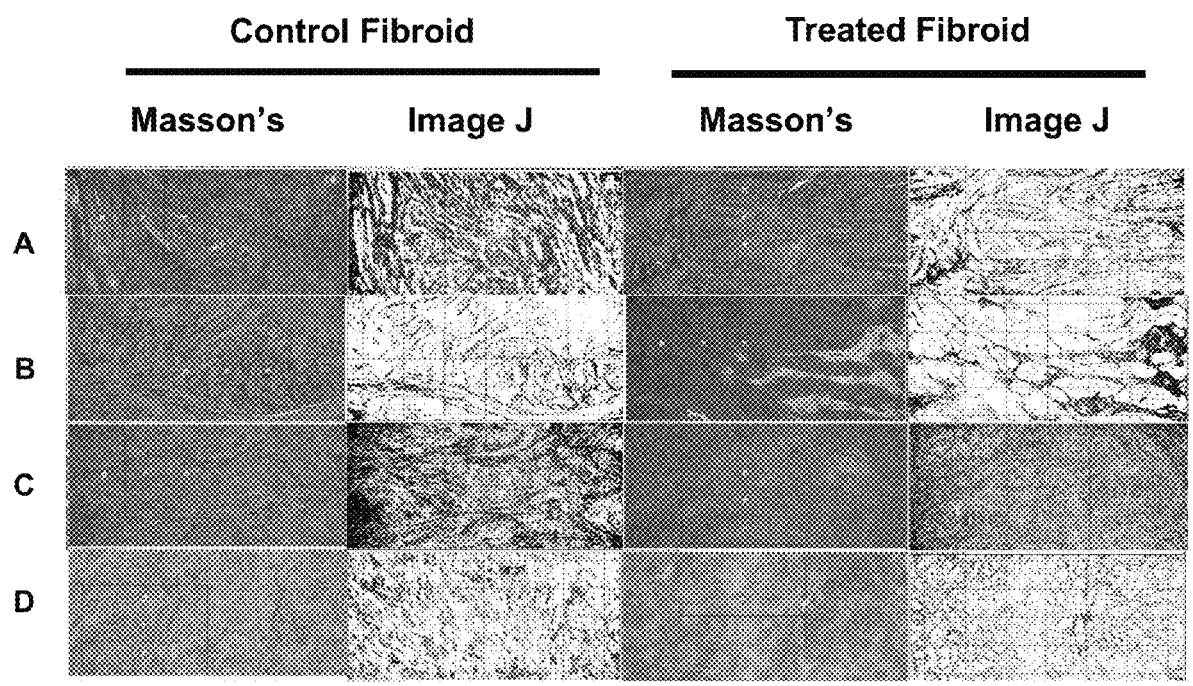
FIG. 3: Representative images of Masson's Trichrome stained Control and Treated fibroid tissue collected at hysterectomy from 4 subjects at various doses of collagenase for GroupI, 1.16 mg (Row A), and Group 2 Dose 1, (Row B), Dose 2, (Row C), & Dose 3, (Row D), with 1.68, 3.35, and 5.028 mg as the maximum doses respectively. The blue green color represents the collagen in the colored images. The black & white images were generated using ImageJ software to analyze the collagen content. The black color represents the collagen. Collagen density was quantified using 9 grids with approximately 500.000 pixels. All treated samples showed a statistically significant reduction in collagen. Magnification is ×5.

The targeted delivery to the center of the fibroids was feasible based on the three Saline only group subjects FIG. 2a demonstrates the extent of spread of methylene blue when injected transvaginally under ultrasound guidance. Treated fibroid tissues were noticeably soft to palpation on gross examination. Some samples injected with higher dosages of EN3835 showed liquefaction at the area of injection (FIG. 2b). The digestion of collagen did not extend beyond the capsule of any fibroid. FIG. 13 details the size of the fibroid injected and the study drug dosage.

Collagen Density and Distribution

Quantitative analysis of Masson's Trichrome stained slides showed that all treated samples had a statistically significant reduction in collagen content compared to the controls (median reduction 39%, range 16-78%; $p<0.001$; FIGS. 3-5, 11). To assess for possible dose-dependent effects, a grouped analysis was performed to compare control and injected fibroid tissues. There was a statistically significant reduction in the collagen content between control and treated fibroids in each study group (FIGS. 5, 11). The additional analysis of comparing collagen content of treated fibroids to a pooled control confirmed a notable reduction (median reduction 42.9%, range 12-64%, FIG. 6).

SFIG analysis showed that treated samples had an average of 21% (range 10-34%) reduction in distribution of collagen bundles compared to controls in each study group (FIG. 7). Picrosirius red stain, imaged under polarized light, showed that collagen fibers in collagenase treated tissues were less dense and shorter than in control tissues. Loss of collagen fibers was noted in treated fibroid tissues (FIG. 8).

Apoptosis

TUNEL assays did not detect an increase in apoptosis in all treated tissue sections compared to control. (FIG. 9). The tissue for analysis was obtained at the time of tissue harvesting post-hysterectomy. The control sections were obtained from matched fibroids from the same subject, and the treated fibroid sections were obtained from the injected fibroid from the subject.

Study Questionnaires

Questionnaires completed by subjects in the Saline-only group showed no distinguishable trends due to the short time interval between administration of questionnaires (baseline and hysterectomy); therefore only Groups 1 and 2 questionnaire results were included in the analysis.

McGill Pain Questionnaire: In Group 1, no subject reported an increase in pain between baseline and 24-48 hours post injection, and two reported an average 5 point decrease in pain. For Group 2, only one of the nine subjects reported an increase in pain by one point between baseline and 4-8 days post study drug injection and no increase in pain was reported at day 60-90 (pre-hysterectomy). On average there was a 14 point reduction in pain at 4-8 days for the other eight subjects in Group 2, and the trend continued for all subjects with an average 15 point reduction at 60-90 days from baseline.

Visual Analogue Scale (VAS)

In Group 1, none of the subjects reported an increase in pain from baseline to 24-48 hours post study drug injection. In Group 2, seven out of nine subjects reported no increase in pain from baseline to 4-8 days post study drug injection, three out of nine subjects reported a mild increase in pain associated with fibroids at 60-90 days post study drug injection. None of the changes were statistically significant.

Uterine Fibroid Symptom Health-Related Quality of Life Questionnaire

Part 1: In Group 1, 2 out of 3 subjects reported an increase in severity of symptoms associated with fibroids between baseline and 24-48 hours post study drug injection. In Group 2, 5 out of 9 subjects reported a mild decrease, 2 out of 9 reported a mild increase, and 2 subjects reported no change in symptom severity between baseline and 4-8 days post study drug injection. Five out of 9 subjects reported a decrease and 4 out of 9 subjects reported a mild increase in symptom severity associated with fibroids between baseline and 60-90 days post study drug injection.

Part 2: In Group 1, all subjects reported an improvement in health-related quality of life between baseline and 24-48 hrs post study drug injection. In Group 2, 4 out of 9 subjects reported a mild improvement, 3 out of 9 reported no change, and 2 out of 9 reported a decrease in quality of life from baseline to 4-8 days post study drug injection. Four out of 9 subjects reported a mild improvement, 4 out of 9 reported a decrease, and one subject reported no change in quality of life associated with fibroids between baseline and 60-90 days post study drug injection.

Safety and Tolerability

No serious adverse event occurred in any subject and no adverse events led to discontinuation of a subject in the study. No allergic reactions were observed in the 12 subjects that received study drug. Eleven of 15 subjects (73.3%) experienced at least one adverse event of which 68.18% were mild and 31.18% were moderate adverse events. Four of the 30 mild adverse events were possibly treatment emergent, vaginal discharge (1) and vaginal spotting (3) but did not require any medical intervention (FIG. 12). Symptoms such as pain and bleeding that are normally associated with fibroids were not recorded as adverse events unless the condition worsened or was unusual for the subject. No subject reported an increase in either pain or bleeding related to fibroids due to the study drug injection. The adverse events labelled as possibly related to the study drug consisted of vaginal spotting and vaginal discharge and were all mild in severity.

There was no association between the dose of collagenase received and the number and severity of adverse events. No other safety concerns such as changes in laboratory tests or abnormal vital signs occurred throughout the study duration for any of the subjects.

Blood samples for pharmacokinetic studies were collected pre-dose, and at 5, 10, 30, 60, and 240 minutes following study drug injection. None of the study subjects had a serum concentration of the drug prior to start of the injections. Plasma concentrations peaked between 7.6 and >160 ng/ml at 5-10 minutes and fell to undetectable by 4 hours post injection. Anti-AUX-I and Anti-AUX-II antibodies were analyzed in serum samples obtained from subjects in Groups 1 and 2 at baseline and the final study visit (3 months post hysterectomy), and an additional sample was taken from subjects in Group 2 at 60-90 days post study drug injection. Exposure to EN3835 resulted in a minimal increase in anti-AUX-1 and anti-AUX-II antibodies, with the highest titers present in Group 2, Dose 3.

Discussion

The results of this phase 1, open-label, and dose-escalation clinical trial found that injectable collagenase *Clostridium histolyticum* was safe and well tolerated when injected directly into the center of a uterine leiomyoma. Uterine fibroids were easy to inject using a follicle aspiration needle under ultrasound guidance. Most obstetricians and gynecologist are qualified to perform ultrasounds and can be trained to execute the injection procedure. Particularly, reproductive endocrinologist and infertility specialists perform similar procedures routinely.

The capsules of all injected fibroids were intact at the time of collection post hysterectomy. When hemi-sectioned, all treated leiomyomas were soft to palpation or showed liquefaction in the center of the fibroid as compared to the periphery of the treated fibroid and the control fibroid from the same subject on gross examination. Histopathological examination using Masson's Trichrome stain revealed that treated leiomyomas have a statistically significant reduction in collagen content. Reduction in density and distribution of the collagen fibrils were observed using Second Harmonic Generation multiphoton electron microscopy analysis and Picrosirius staining. The collagen fibers were shorter in length and fewer in number in the treated versus control tissues on the Picrosirius stained slides.

In this study, injectable collagenase *Clostridium histolyticum* significantly reduced the collagen content in the treated fibroid compared to the control at all treated doses. The gross findings, complemented by the histopathological findings, supported the hypothesis that EN3835 was safe and well tolerated when injected directly into uterine fibroids, thus satisfying the primary outcome of the study.

Eight out of nine subjects in Group 2 reported a notable reduction in fibroid related pain at both the 4-8 day and 60 to 90 day post-injection time points, as evaluated by the McGill Pain questionnaire. All subjects in this phase 1 study received the study drug in the OR under heavy sedation. However none of the subjects experienced significant levels of pain post injection during recovery, and if pain relief was needed, Tylenol always provided sufficient relief.

New drugs for medical management of uterine fibroids such as selective progesterone receptor modulators, oral GnRH antagonists have a reported 50-60% reduction in fibroid size, but larger fibroids tend to persist and may cause symptoms. EN3835 is an effective combination agent to induce regression of fibroids, during or following treatment with other medical therapies to ensure better long term outcomes in fibroid management. Specifically, patients interested in fibroid management with fertility preservation are prime candidates for this therapy. EN3835 and the drug delivery method described herein provide a new, non-hormonal treatment for uterine fibroids.

Conclusions

Collagenase *Clostridium histolyticum* (EN3835) was safe and well tolerated when injected directly into uterine leiomyomas under ultrasound guidance. Treatment resulted in a significant reduction in collagen content in all treated fibroid samples.

Example 10

Abstract

Objective

Uterine fibroids (leiomyomas) are common benign tumors of the myometrium but their molecular pathobiology remains elusive. These stiff and often large tumors contain abundant extracellular matrix (ECM), including large amounts of collagen, and can lead to significant morbidities. After observing structural multiformities of uterine fibroids, this heterogeneity was explored by focusing on collagen and tissue stiffness.

Methods

For 19 fibroids, ranging in size from 3 to 11 centimeters, from eight women gross appearance and evaluated collagen content were documented by Masson trichrome staining. Collagen types were determined in additional samples by serial extraction and gel electrophoresis. Biomechanical stiffness was evaluated by rheometry.

Results

Fibroid slices displayed different gross morphology and some fibroids had characteristics of two or more patterns: classical whorled (n=8); nodular (n=9); interweaving trabecular (n=9); other (n=1). All examined fibroids contained at least 37% collagen. Tested samples included type I, Ill, and V collagen of different proportions. Fibroid stiffness was not correlated with the overall collagen content (correlation coefficient 0.22). Neither stiffness nor collagen content was correlated with fibroid size. Stiffness among fibroids ranged from 3028 to 14180 Pa (CV 36.7%; p<0.001, one-way ANOVA). Stiffness within individual fibroids was also not uniform and variability ranged from CV 1.6 to 42.9%.

Conclusions

The observed heterogeneity in structure, collagen content, and stiffness highlights that fibroid regions differ in architectural status. These differences can be associated with variations in local pressure, biomechanical signaling, and altered growth. The design of all fibroid studies should account for such heterogeneity because samples from different regions have different characteristics. Understanding of fibroid pathophysiology greatly increases through the investigation of the complexity of the chemical and biochemical signaling in fibroid development, the correlation of collagen content and mechanical properties in uterine fibroids, and the mechanical forces involved in fibroid development as affected by the various components of the ECM.

Introduction

Uterine fibroids, also called leiomyomas, are benign tumors that arise from myometrium. Seventy to eighty percent of women will develop uterine fibroids by age 50 (Baird et al. 2003), and many suffer from pressure, pain, infertility, and severe bleeding. While these widespread tumors have been the subject of basic and translational studies for decades (Stewart et al. 2016, Stewart et al. 1994, Cramer et al. 1990, Konishi et al. 1983), their molecular pathobiology remains elusive and as a result current treatment options are limited. These tumors are fibrotic and enveloped by a pseudocapsule that separates the benign tumor tissue from the surrounding myometrium. A reduction in pain may be due to loss of pressure on the pseudocapsule.

It has been shown by different techniques that uterine fibroids are two to four-fold stiffer than myometrium (Jayes et al. 2016, Rogers et al. 2008, Norian et al. 2012, Brunengraber et al. 2014). The stiffness of fibroids results from their abundant extracellular matrix (ECM) which includes large amounts of glycosaminoglycans and more importantly large amounts of disordered, highly cross-linked interstitial collagens (Rogers et al. 2008, Norian et al. 2012, Flake et al. 2013, Barker et al. 2016, Leppert et al. 2004, Leppert et al. 2014, Flake et al. 2013, Kamel et al. 2017). In addition, studies have linked the increased stiffness to altered biomechanical signaling in the tumors (Rogers et al. 2008, Norian et al. 2012). In addition, there are a smaller number of vessels with decreased diameter in fibroids. The average pressure of interstitial fluid in fibroids is 4 mm Fig, while that in myometrium is 1 mm Fig.

Fleterogeneity of uterine fibroids is often not appreciated and therefore not considered in the design and conduct of basic, translational, and clinical studies. As a result, there are numerous shortcomings in understanding the pathobiology of these tumors. Without clear characterization of samples, it is challenging to define and compare phenotypes. An appreciation of sample differences better enables comparisons between studies and improve understanding of these benign but problematic fibrotic tumors. Fleterogeneity has been documented on the genetic/genomic, proteomic, metabolomic and histologic level (Stewart et al. 2016, Catherino et al. 2003, Flodge et al. 2008, Makinen et al. 2011, McGuire et al. 2012, Yatsenko et al. 2017, Mahine 2015, Fleinonen et al. Sci Rep. 2017, Fleinonen et al. Br J Cancer 2017, Jamaluddin et al. Endorinology 159(2), 2018, Jamaluddin et al. Endorinology 159(7), 2018, Floldsworth-Carson et al. 2016). During ongoing research on the development of treatments for uterine fibroids, additional heterogeneity has been noted. The gross pathologic appearance of uterine fibroids is usually described as well circumscribed, firm, white to greyish whorled tissue (D'Angelo et al. 2014). Flowever, a wide range of gross appearances and variability in fibroid stiffness has been observed. The intra and interfibroid variations observed by gross appearance, mechanical properties, and content of interstitial cross-linked helical collagens which provide stiffness to fibroids are characterized.

Methods

Collection of Fibroid Tissues for Appearance, Amount of Fibrosis and Stiffness

Studies were approved by the Duke Institutional Review Board. Women over 18 years of age with a diagnosis of uterine fibroids provided written consent. Fibroid tissue from 20 tumors was obtained post-hysterectomy in nine subjects. All tumors were considered to be common benign uterine fibroids by the examining pathologist and none of the tumors were from patients with the hereditary leiomyomatosis and renal cell cancer (HLRCC) syndrome.

The fibroids varied in size from three to eleven centimeters in diameter. Tissue from one subject was excluded from the analysis because the tissue was recalled by the pathologist for further examination. Therefore, 19 fibroids from eight subjects were included in the analysis.

Immediately following surgery, slices (cross sections) of approximately 1 cm thickness from each fibroid were obtained. The tissues were transported to the laboratory and washed as described previously (Jayes et al. 2016). The gross appearance of the cut surface was observed and recorded; photographs were successfully obtained for 18 fibroids. Tissue slices were then cut into smaller pieces and either snap frozen at $-80°$ C. for mechanical stiffness studies or fixed in formalin for histology.

Masson Trichrome Staining

Fixed tissues were paraffin embedded, sectioned (5 pm), and stained with Masson trichrome in the Duke Histology Core Laboratory. Masson trichrome is commonly used to differentiate collagen (stained blue-green) from surrounding muscle cells (stained red). Briefly, slides were stained with Weigert's iron hematoxylin followed by Ponceau acid fuchsin. After treatment with phosphomolybdic-phosphotungstic acid slides were stained with Light Green in acetic acid. Whole slides were scanned at 20×(Aperio Scanscope, Leica Biosystems Inc., Buffalo Grove, IL). Aperio ImageScope and ADOBE® Photoshop (ADOBE® Systems Inc., San Jose, CA) CS6 software was used to analyze the entire section on each slide. The quantity of blue-green pixels as a proportion of total pixels was used to determine percent (%) collagen as previously described (Jayes et al. 2016, Brunengraber et al. 2014).

Mechanical Stiffness Studies

Each fibroid described above was evaluated for the biomechanical property of stiffness by rheometry as described previously (Jayes et al. 2016). Briefly, from each fibroid, two to three random 5 mm diameter punches were obtained (n=44) and measured dynamically to determine sample stiffness (complex shear modulus Pascal [Pa] at 10 rad/sec) taking into account both the viscous and elastic behavior of the tissue. Freezing and thawing and repeat measures of fibroid tissue did not affect stiffness measurements (Jayes et al. 2016). The punches from each fibroid were used to calculate variability within fibroids. Samples from each fibroid were averaged to calculate fibroid stiffness for comparison among fibroids. Five subjects had more than one fibroid (2-4 fibroids per subject) and average stiffness per subject was calculated for comparison among subjects.

Determination of type I, Ill, and V collagen content Uterine fibroid samples. From five additional consented subjects, fibroid tissue samples immediately following hysterectomy were obtained as described previously (Behera et al. 2007). Fibroid size ranged from 4 to 12.5 cm and tissue samples (1 cm3) were obtained within 1 cm from the fibroid edge (E) and from the center (C) of each fibroid. These tissues were immediately frozen and stored at $-80°$ C. until analysis for types I, Ill, and V collagen by classical, stringent collagen extraction techniques. The collagen type I/III ratios were calculated as a classical indicator for tissue remodeling.

Collagen extraction and analysis. To extract collagen, 10-30 mg of minced tissue from each sample was incubated overnight at 4° C. in 1 ml of freshly prepared 0.1 mg/ml pepsin/0.5 Macetic acid (HAc) solution. The remaining insoluble tissue was removed by centrifugation and subjected to repeated extractions under the same conditions. The collagen yield became negligible in the fourth extract, which was discarded together with the tissue. The first three extracts were combined. Collagen was precipitated by adding sodium chloride (NaCl) to 2M final concentration, separated by centrifugation, resuspended in 50 mM Tris/0.1 MNa-carbonate/0.5MNaCl (pH 7.58.5), and treated with 0.1 mg/ml pronase for 4-5 h at 4° C. The pronase treatment was stopped with 0.5MHAc (final concentration) and collagen was purified by precipitation with 2M NaCl (final concentration). This treatment was utilized to disrupt pepsin-resistant intramolecular cross-links, minimizing the amount of cross-linked a 1 (I)2a 2(I) trimers that migrate close to disulfide-bonded a 1 (III)3 trimers on unreduced gels.

The purified collagen was fluorescently labeled with amino-reactive Cy5 (GE HEALTHCARE®) as previously described (Makareeva et al. 2010). Its chain composition was analyzed in triplicate by gel electrophoresis on precast 3-8% Tris-acetate gradient mini-gels (Invitrogen) with and without the reducing agent, Tris (2-carboxyethyl) phosphine (TCEP, Invitrogen). The fraction of each chain was determined from the fluorescence intensity of the corresponding band on the gel. The intensities were calibrated using purified types I, III and V collagen. Globular molecular weight standards are not useful for collagen SDS/PAGE analysis, because collagen chain migration is strongly affected by their high proline content. Only collagen bands were present in these gels and identified by their relative position. Type III collagen chains were identified based on their migration as trimers without TCEP and comigration with a 1 (I) in the presence of TCEP. To accurately determine the intensities of a 1 (I) and a 2(V) bands that migrate close to each other on the gel, depleted and enriched fractions of type V collagen were analyzed. The type V collagen depleted fraction was purified by selective precipitation of types I and III collagen from 0.5 MHAc solution with 0.7MNaCl. The type V collagen enriched fraction was purified by subsequent precipitation of the remaining type V collagen with 2MNaCl. The ratio of a 1 (1)/a 2(1) band intensities was determined by analyzing the type V collagen depleted fraction and the ratio of a 1 (V)/a 2(V) band intensities by analyzing the type V collagen enriched fraction. These ratios were then utilized to recalculate the fractions of a 1 (I), a 2(1), a 1 (III), a 1 (V), a 2(V), and a 3 (V) chains in initial samples and thereby determine the fractions of types I, III and V collagen in extracts from different fibroids.

Statistics

Tissue stiffness was determined as the average of the measurements from 2-3 punches from each sample. Stiffness data measured in Pascal [Pa] is presented in the results as mean±SD. Stiffness in fibroid samples ranged widely and therefore the variability was also expressed as CV (coefficient of variation calculated as the standard deviation divided by the mean). This statistic describes the percent standard deviation from the mean and allows for the relative comparisons of variability even if means are considerably different from one another. Analysis of variance (Oneway ANOVA) followed by Sidak's multiple comparison test was performed using GRAPHPAD PRISM® (La Jolla, CA) to compare stiffness among fibroids. Differences were considered significant at P☐0.05. Pearson's correlation coefficient was calculated for tissue stiffness and collagen content using the formula function in MICROSOFT® EXCEL® 2016.

Results

Gross Anatomy Reveals Diverse Architectural Patterns

Figure 14:
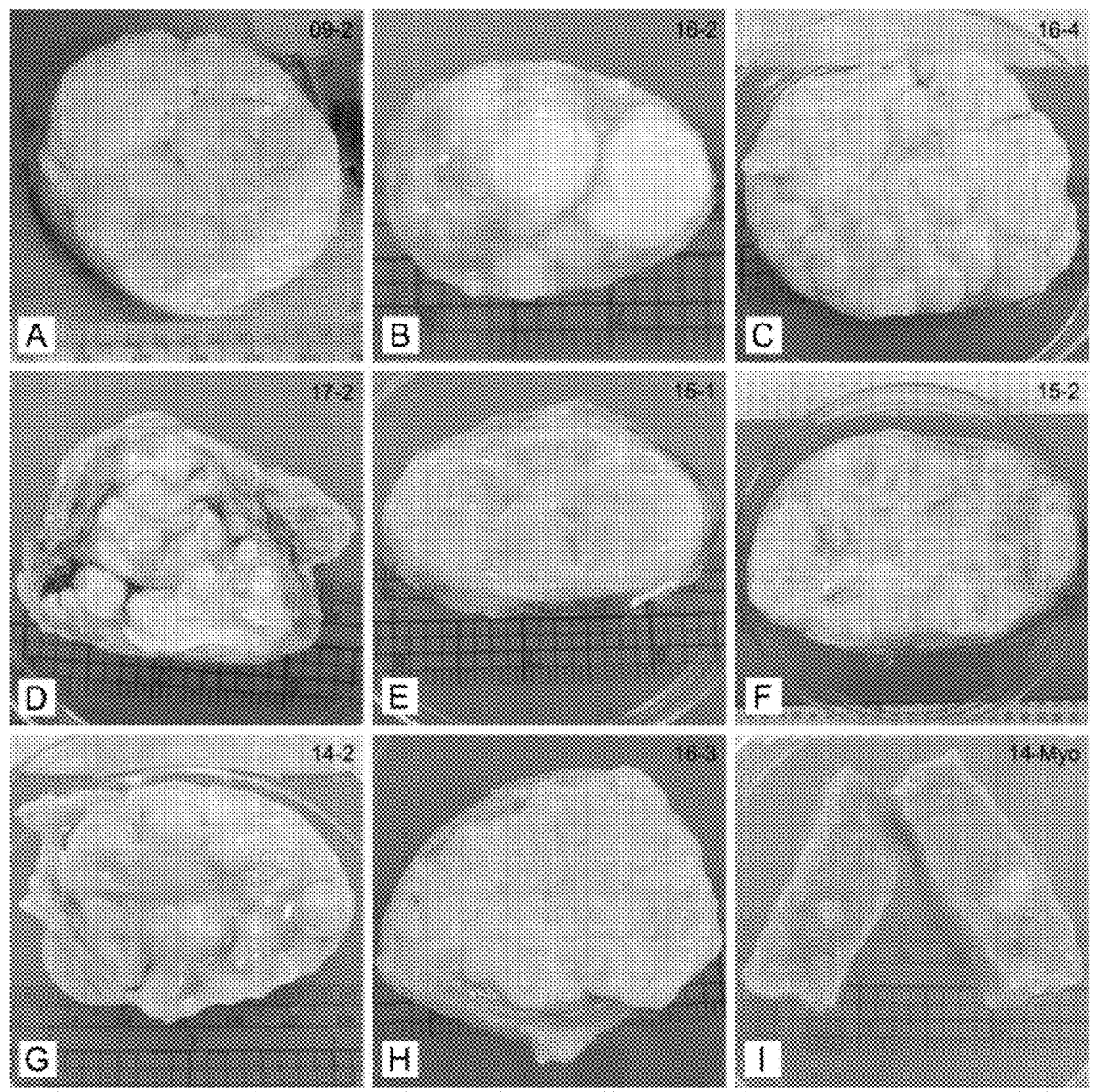
FIG. 14. Representative photographs of tissue slices showing differences in gross appearance of fibroids. A: Classical irregular whorled pattern; B, C, D: Patterns of nodules; E, F: Trabecular structures; G: Characteristics of multiple patterns. This example shows a trabecular/nodular pattern; H: Not categorized. This example shows a tightly gyrated pattern. I: Myometrial tissue shown for comparison. Note the seedling fibroid embedded in the tissue (white appearance). Ruler (cm) shown for size.

On the cut surface of the 19 tumor slices studied, a spectrum of tissue architectural patterns was observed. Eight fibroids displayed the classical whorled pattern traditionally described in textbooks (FIG. 14A). In nine fibroids, a nodular pattern with small and large nodules was observed. Upon cutting the slices, most nodules immediately protruded above the cut surface. These nodules varied in size from 2 to 14 mm and were stiffer to palpation than surrounding areas (FIGS. 14B, 14C and 14D). In nine fibroids an interweaving trabecular pattern was observed (FIGS. 14E and 14F), and six fibroids displayed characteristics of two or more of these patterns (FIG. 15 and FIG. 14G). Two fibroids could not be assigned to one of the three main categories. In one of these fibroids a pattern reminiscent of gyri in brain tissue was observed (FIG. 14H). Myometrial tissue is shown for comparison (FIG. 14I). This particular sample contained the coincidental finding of a small seedling fibroid that was firm to palpation. In in fibroids and also observed patterns not commonly described. Some fibroids displayed multiple patterns.

Masson Trichrome Staining (Collagen Content)

We found an abundance of positive Masson trichrome staining in fixed tissues and confirmed that collagen is a large component of uterine fibroids. Tissue samples (approximately 1×1 cm) from each fibroid, had been stained with Masson trichrome and the entire section was captured as a digital microscopic scan (FIG. 15). The representative images in FIG. 15 were chosen to show examples of high and low collagen content with a similar overall shape of the tissue section for better direct comparison. The circular holes visible in each sample in FIG. 15 are due to 5 mm punches taken for rheometry before samples were fixed and stained for collagen. The entire tissue area from each sample was used for analysis and contained on average 3.5× 108±2.4×107 pixels (mean±SEM). All examined fibroid slices contained at least 37% collagen and collagen staining varied widely (FIG. 15). Fibroid size was not correlated with collagen content (correlation coefficient=0.065).

Mechanical Stiffness Highlights Fibroid Variability Profile

Figure 16:
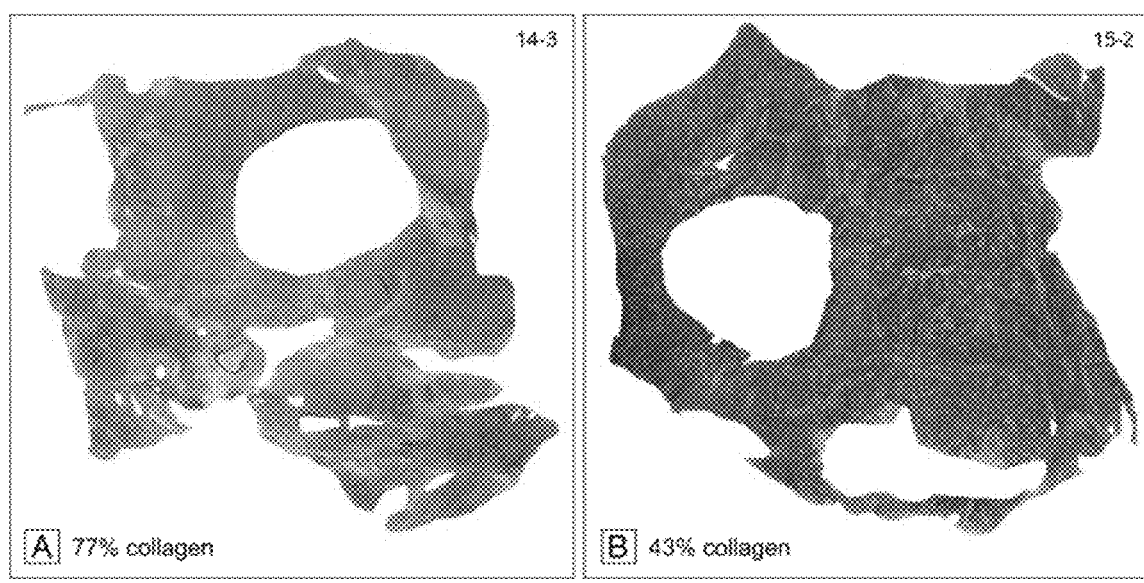
FIG. 16. Representative samples of Masson trichrome-stained fibroid tissues (collagen stained blue-green; muscle cells stained red) examined under digital microscopy (20×). Samples (approx. 1×1 cm) from 2 different fibroids were chosen representing a high collagen content (A: 14-3) and a relatively low collagen content (B: 15-2). The circular holes are due to 5 mm punches taken for rheometry before samples were fixed and stained. Collagen was quantified using pixel counts and is denoted underneath each sample.

A total of 44 samples were measured by rheometry utilizing settings previously used in fibroid tissues (Jayes et al. 2016). Stiffness among all individual tissue punches (within and between fibroids) varied widely (range=2027-16130 Pa; mean=7628 Pa; median=7216 Pa; SD=3254 Pa; CV=42.7%). Data reported in FIG. 15 lists the sample averages from the 2-3 punches from each fibroid slice. Averages ranged from 3028 to 14180 Pa (FIGS. 15 and 16; CV 36.7%; p<0.001, oneway ANOVA), and revealed among-fibroid variability. Within-fibroid variability is visualized by the error bars (SD) in FIG. 16; standard deviations ranged from 70 to 4110 Pa (FIG. 16; CV 1.6 to 42.9%, median CV 22.1%). Within-subject variability was also observed in the five subjects with more than one fibroid (SD 800 to 3500 Pa; CV 12.2 to 36.4%). For example, the three fibroids from Subject 17 have stiffness values ranging from 7325 to 14180 Pa (FIGS. 15 and 16). Interestingly, fibroid stiffness was neither correlated with the percent collagen content (FIG. 16; correlation coefficient=0.22), nor with fibroid size (correlation coefficient=0.002).

Type I, III, and V Collagen Content in Five Fibroids

Figure 17:
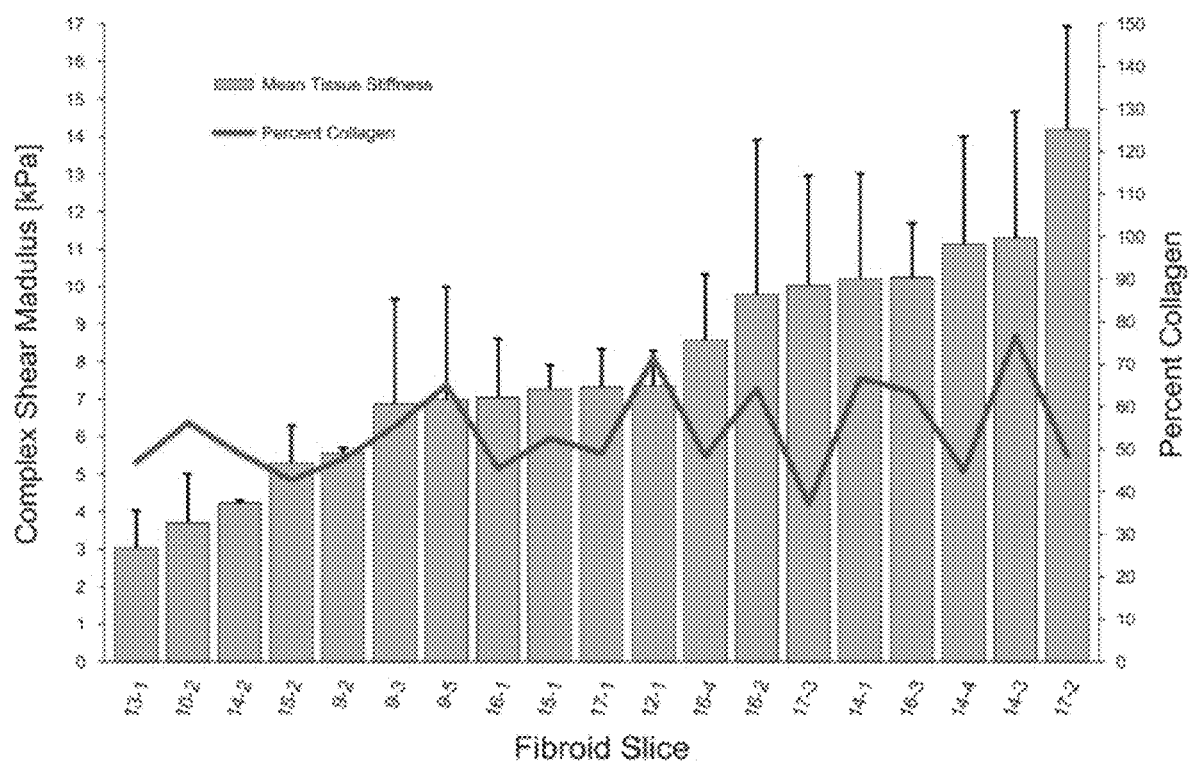
FIG. 17. Stiffness and percent collagen in fibroids. Columns represent mean tissue stiffness (complex shear modulus [kPa]) in 19 fibroid slices from 8 different subjects. X-axis labels indicate the subject number followed by the fibroid number. Five subjects contributed more than one fibroid to the study. Error bars indicate within-fibroid variability (SD). The pink line represents percent collagen in each fibroid slice as determined by analysis of Masson trichrome staining. The correlation coefficient of stiffness to percent collagen was 0.22.
Figure 18:
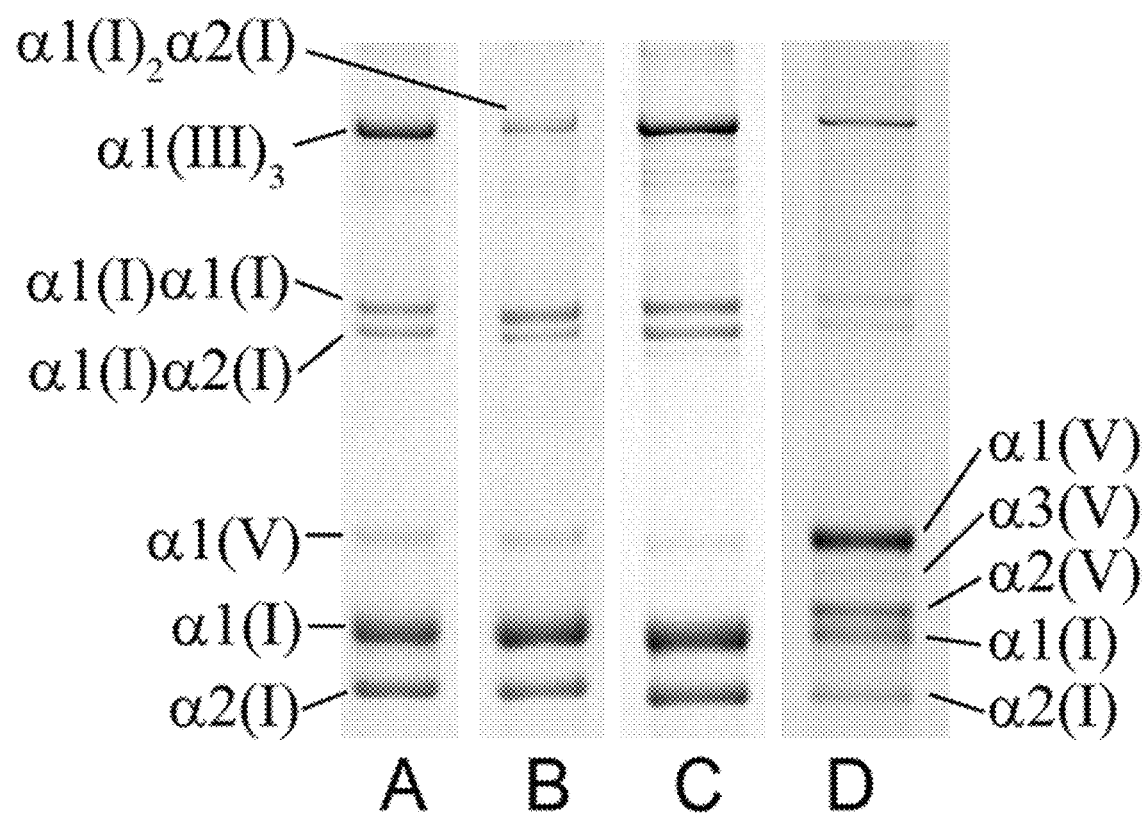
FIG. 18. SDS-PAGE analysis of collagen in a representative fibroid sample. Lane A: Total collagen extract under nonreducing conditions. Lane B: Total collagen extract under reducing conditions (with TCEP). Lane C: Collagen extract depleted of type V by selective salt precipitation. Lane D: Collagen extract enriched in type V by selective salt precipitation. Sample shown is from 395-E.
Figure 21:
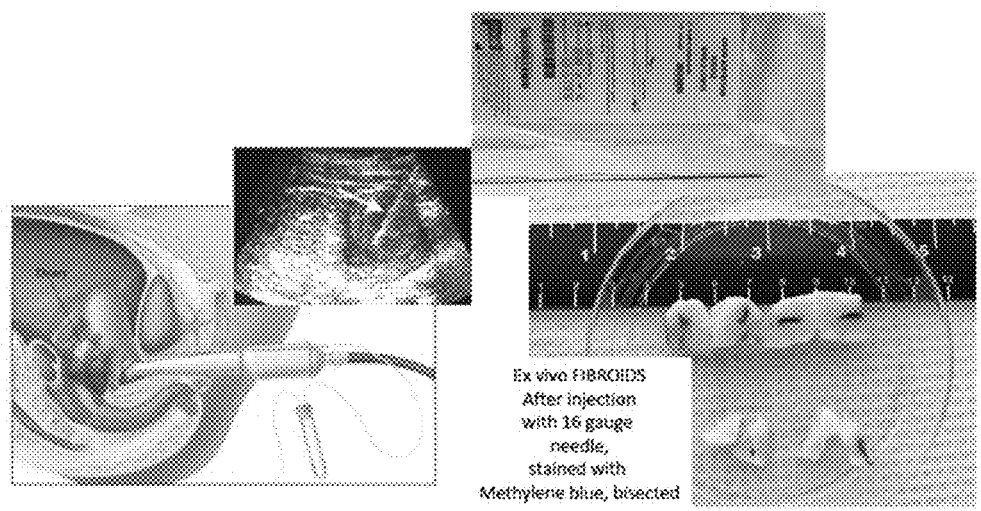
FIG. 21. Procedure for injection of EN3835.
Figure 22:
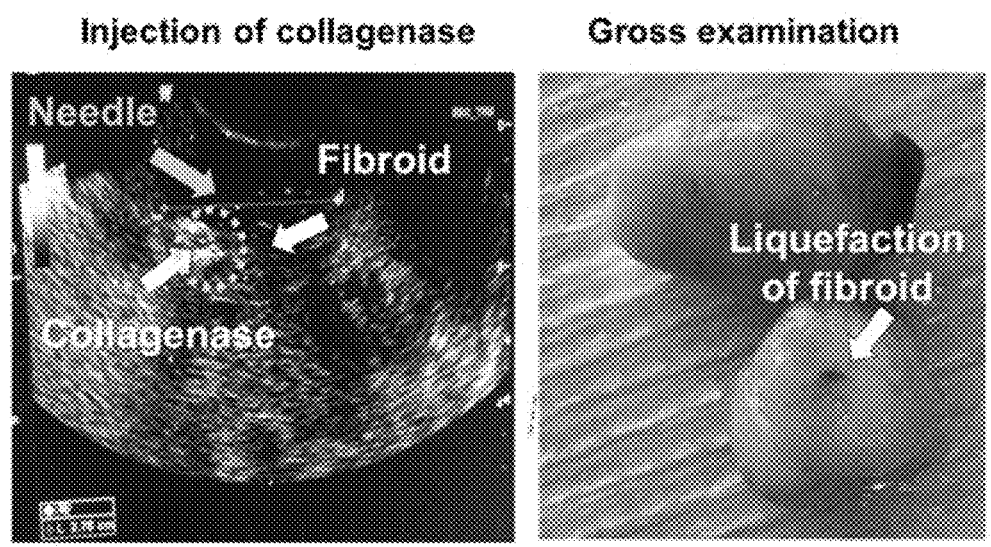
FIG. 22. Shows an ultrasound of a fibroid, showing a needle for injecting the collagenase, and the injected collagenase, as well as a gross examination of an injected fibroid.
Figure 24:
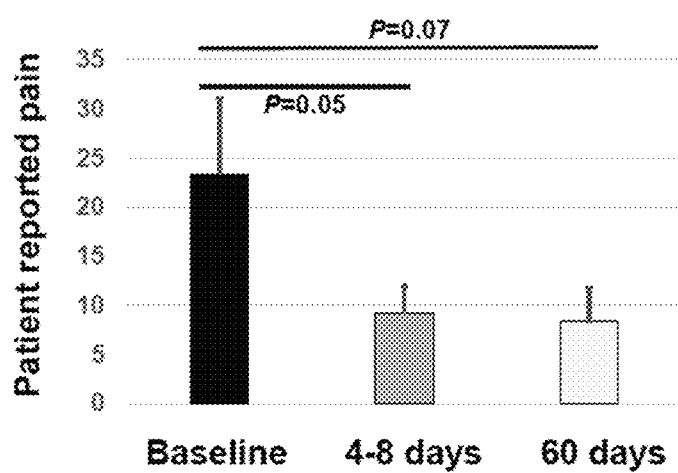
FIG. 24. McGill Pain Score: Group 2. Error bars=SEM, Paired t-test, n=9 study subjects.
Figure 25:
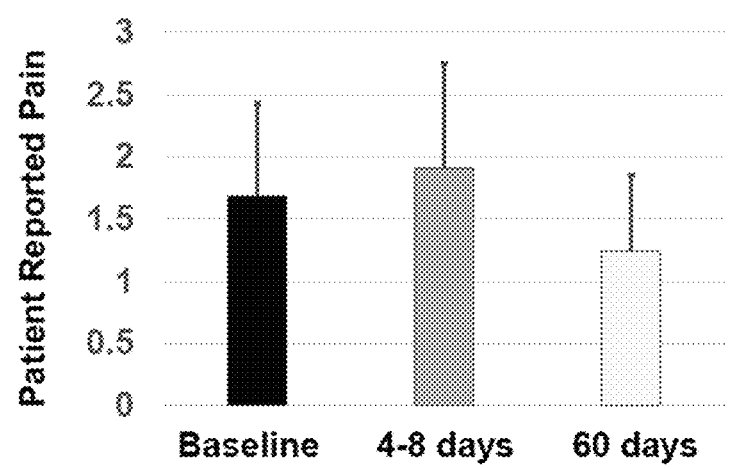
FIG. 25. Visual Analog Pain Scale: Group 2. Error bars=SEM, Paired t-test, n=9 study subjects, P=0.68.
Figure 26:
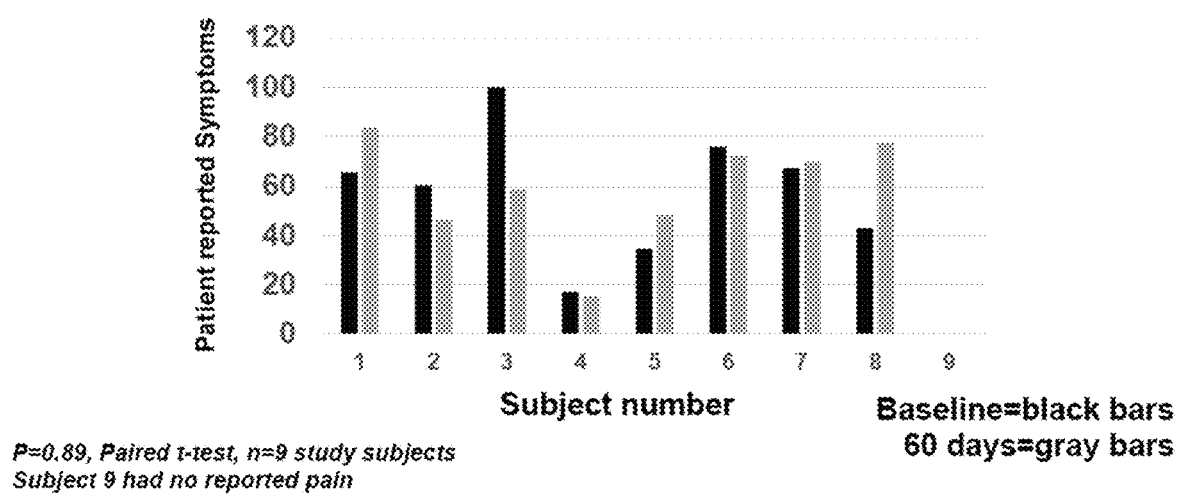
FIG. 26. UFS-QoL: Group 2. P=0.89, Paired t-test, n=9 study subjects. Subject 9 had no reported pain. Baseline=black; 60 days=gray.
Figure 27:
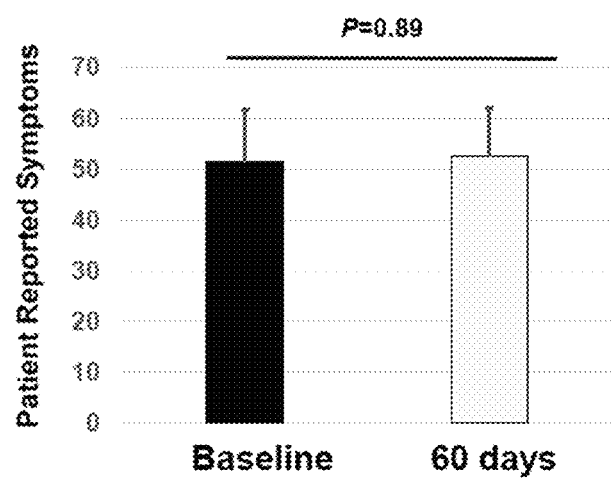
FIG. 27. UFS-QoL: Group 2. Error bars=SEM, Paired t-test, n=9 study subjects.
Figure 29:
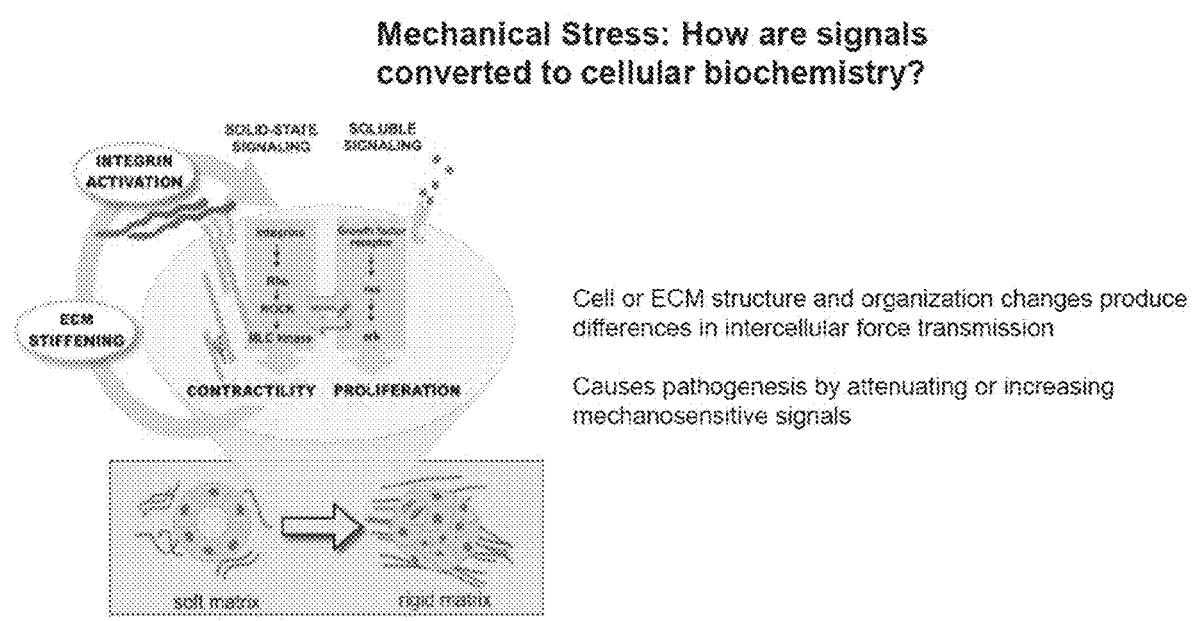
FIG. 29. Mechanical stress and how signals are converted to cellular biochemistry in uterine fibroids.
Figure 30:
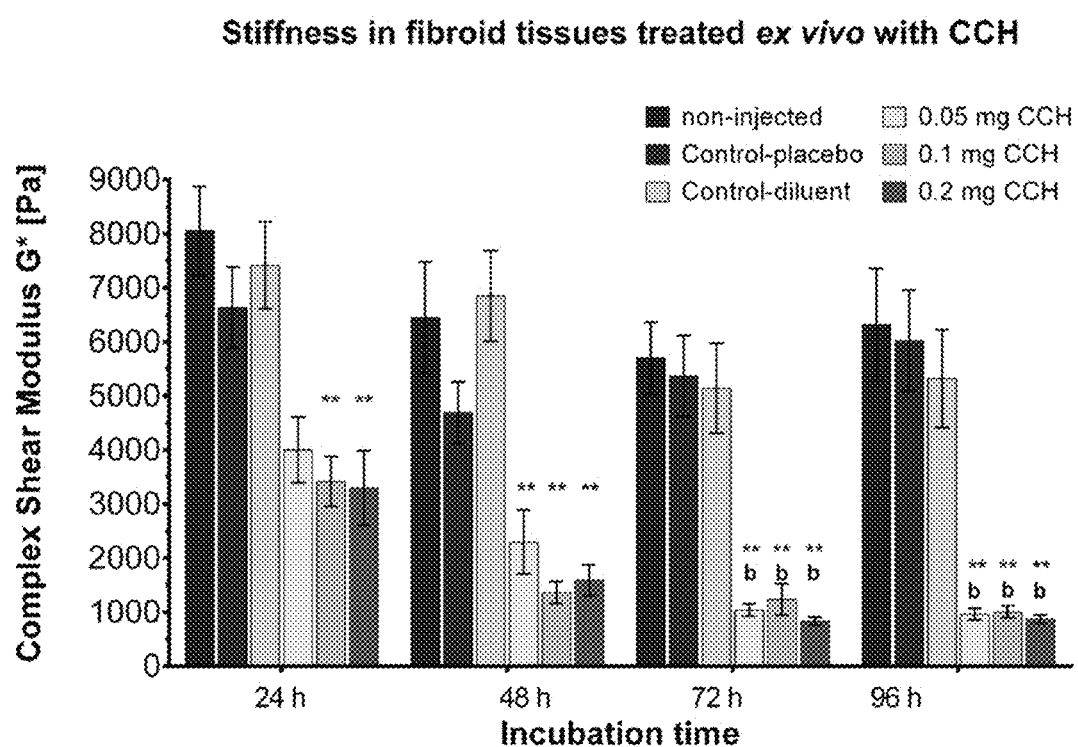
FIG. 30. Stiffness in fibroid tissues treated ex vivo with collagenase *Clostridium histolyticum* (CCH).

The examined fibroid tissues, taken from the center (C) and edge (E) of each of five additional subjects, were studied by classical, stringent collagen extraction techniques. They contained interstitial collagens types I, III, and V of different proportions (FIGS. 17 and 19). While type V collagen was found in all examined fibroid samples, type I and type III collagens were predominant. The proportions of types I, III, and V collagen varied among fibroids samples and ranged from 37-74%, 22-55%, and 2.0-7.4%, respectively. In 4 out of 5 fibroids type I collagen was the major component, but in one fibroid sample (#8), type III was present in higher amounts than type I.

Discussion

Previously, there have been reports on the abundant extracellular matrix, especially collagen and glycosaminoglycans content in fibroids and their contribution to mechanical signaling mechanisms and fibroid stiffness (Rogers et al. 2008, Norian et al. 2012, Flake et al. Obstet Gynecol Int. 2013:528376 (2013), Barker et al. 2016, Leppert et al. Fertil Sertil. 2004, Leppert et al. Obstet Gynecol Int. 2014, Kamel et al. 2017). The present observations provide novel evidence that fibroid structural properties and collagen content vary widely. The variations found in gross appearance of uterine fibroids were striking. In addition, large differences in collagen content and composition as well as stiffness were noted both within and among individual fibroids. Variations in fibroid biology may be associated with different stages of growth and underlying differences in gene expression, protein synthesis, and mechanical signaling and other second messenger production or release. Increased awareness of these differences and intentional consideration of these variations when designing studies and interpreting data leads to a better understanding of the etiology and pathophysiology of uterine fibroids. Early research involving uterine fibroids has mostly focused on the cellular components of fibroids. Now, the important role of the ECM in fibroid growth has been increasingly accepted (Leppert et al. 2006, Islam et al. 2018). This study validates that fibroids contain a large percentage of interstitial collagens (Brunengraber et al. 2014, Flake et al. Obstet Gynecol Int. 2013:528376 (2013)), substantiating that these proteins are an important component of uterine fibroids. Understanding the collagen content, composition, and metabolism in fibroids greatly improves overall understanding of uterine fibroid etiology and pathophysiology. Findings of high variability in collagen content within and among fibroids indicate that collagen metabolism in these benign tumors is active (Leppert et al. 2006, Islam et al. 2018), and that this metabolism also varies from fibroid to fibroid. Furthermore, several individuals with more than one fibroid stiffness varied among their fibroids, strongly suggesting that in addition to systemic hormonal milieu, local conditions and mechanotransduction may determine fibroid development, growth, and regression. Cells sense the physical force surrounding them and translate this force into biochemical signals that modulate biological responses (reviewed in Paluch et al. 2015). The mammalian cell responds to physical cues such as stiffness in its environment through a complex system of ECM receptors and transmembrane molecules that interconnect with the cytoskeleton, integrin subunits, and surface glycoproteins (reviewed in Leppert et al. 2014). The process of mechanotransduction is dynamic and reciprocal and is as important as traditional biochemical signaling. The ECM stiffness alters signaling within the cell while the cells in turn can modulate the ECM, remodeling the matrix to be either stiff or flexible.

Mechanical forces within collagen-rich fibrotic tissue are known to stimulate cells to secrete more collagen and other components of the ECM. Subsequently, cells develop resistance to programmed cell death (apoptosis) which leads to the persistence of cells and continued secretion of collagen (Ho et al. 2014). Mechanical forces consisting of highly cross-linked collagen surrounding individual cells act as localized stimuli for changes in cell biology and behavior, including gene expression. (Leppert et al. 2014, Thorne et al. 2015, Jorge et al. 2014). The size of the fibroids in this study ranged from 3 to 11 cm in diameter and significant amounts of collagen in fibroids regardless of size were found. In uterine fibroids, the degree of hydration and osmotic forces and glycoaminoglycans also play a part in mechanotransduction. (Thorne et al. 2015, Jorge et al. 2014, McCarthy-Keith et al. 2011).

Multiple gene expression studies have been carried out with variable results. Some studies suggest that the wide range of expression profiles are due to subtle differences in the characteristics of subjects or laboratory conditions. (Catherino et al. 2003). Fibroids are of clonal origin and certain variations and mutations in specific chromosomes have been found in some fibroids but not in others, revealing genetic heterogeneity among tumors. (Stewart et al. 2016, Hodge et al. 2008). Whole genome sequencing has reported three genetic triggers of fibroids: FH inactivation, HMGA2 overexpression and COL4A5 and COL4A6 deletion. (Mehine et al. 2013). In addition, two recent studies found MED12 mutations in up to 70% of fibroids examined (Makinen et al. 2011, McGuire et al. 2012), but a similar study revealed remarkable genomic heterogeneity (Yatsenko et al. 2017). Through focal adhesions and stress fibers leading to the nucleus, alterations in gene expression can be part of the process of mechanotransduction (discussed in Leppert et al. 2014, Paluch et al. 2015) and understanding the precise mechanisms of how mechanical clues are transduced to the nucleus to influence gene transcription is useful. (Uhler et al. 2017). Variations in fibroid biology can be associated with differences in genetic and non-genetic initiation factors, stages of growth, and, ultimately, gene expression, protein synthesis, and second messenger production or release induced by mechanotransduction. The localized process of mechanotransduction causes individual fibroid cells to change behavior in discrete areas of fibroids. This creates intra-fibroid tissue variability in gene and protein expression, collagen accumulation of different types, and cytokine release. It is interesting to note that distinct spatial differences in expression of vascular endothelial growth factor (VEGF) were reported a decade ago. (Wei et al. 2006). Microarray data indicate that gene expression within the same fibroid can vary depending on location. Differences in the expression of 15 genes between two differing regions has been analyzed (Evans et al. 2016), and these could be due to differences in the underlying localized pathophysiology as a result of mechanical factors. Increased understanding of differences in gene expression within and among fibroids assists in the development of targeted therapies. It has been reported that uterine fibroids grow at different rates within the same woman, and spontaneous regression of these benign tumors can occur (Peddada et al. 2008). Furthermore, fibroid size does not predict growth rate. (Peddada et al. 2008).

Studies designed to determine the exact characteristics of fibroid growth and to determine the growth status of surgically obtained tissue are needed and will advance the field. Future studies of fibroid growth should take mechanotransduction into consideration. When sliced, considerable variation in gross appearance of fibroids became apparent. Not only did were the whorled pattern traditionally described in textbooks observed, but distinct nodular, trabecular, and combination patterns were also seen.

Underlying differences in biochemistry and thus pathophysiology may be responsible for the whorled, nodular, trabecular, and combination patterns appearances of the individual samples. For example, one indicator that the tissue was under tension was that nodules immediately protruded from the surface upon cutting. The localized process of mechanotransduction could lead to varied amounts of force exerted on cells in discrete areas of individual fibroids, resulting in structural changes and thus variations in gross appearances.

Interstitial collagen, a major component of the ECM, is one contributor to the stiffness of the matrix. Fibroids have been shown to be stiffer than myometrium in several studies and their results show two to four-fold differences using various measures of mechanical properties (Jayes et al. 2016, Rogers et al. 2008, Norian et al. 2012, Brunengraber et al. 2014). All fibroids examined in this study contained large amounts of collagen. (FIG. 17). Increases in collagen cross-linking contribute to the biomechanical properties of stiffness in fibroid tissue (Jayes et al. 2016, Norian et al. 2012), and a recent study has shown that uterine fibroids contain more collagen cross-links than surrounding myometrium (Kamel et al. 2017). Higher levels of glycosaminoglycans in uterine fibroids compared to surrounding myometrium also contribute to their stiffness. (Norian et al. 2012, Barker et al. 2016, Leppert et al. 2014).

Collagen accumulation in tissues is also a hallmark of many localized fibrotic diseases and systematic fibrosis. This collagen accumulation occurs after injury and wound healing or other mechanical stimuli. Masson trichrome does not allow for the determination of the types of collagen present or the amount of cross-linking of the accumulated collagen molecules. The uterine myometrium contains some type IV collagen found in blood vessels, but the most predominant collagens are the interstitial types I, III and V collagen (Kao et al. 1977). Uterine fibroids arise from the myometrium and thus these same collagen types are prominent in these tumors.

Genes of other collagen types have been reported in microarray studies of uterine fibroids and their adjacent myometrium, (Tsibris et al. 2002) but no previous studies have reported biochemical evidence of mature interstitial collagen proteins. Using classical techniques of pepsin digestion, serial precipitation of collagen by NaCl gradient, and separation on SDS gels, the types of interstitial collagens in five fibroids were determined (FIG. 19). Not only was there a notable variation in proportions of types I, III and V collagen, there was also a variation in the type I/III ratios. In one of the examined fibroids the main component of the tissue was type III (58%) as opposed to type I collagen, which is typically the main collagen component of almost all tissues. In the same fibroid, collagen type V was also elevated. Elevated type III results in decreased collagen type I/III ratios. Such decreased type I/III ratios, as well as elevated type V, are reported in early granulation tissue and restored in late wound healing in scar formation. (Latha et al. 1999, Gabbiani et al. 2003, Gabbiani et al. 1976). The present findings support the conclusions of other reports suggesting the involvement of the reparative process in the development of uterine fibroids. (Leppert et al. 2006, Malik et al. 2010, Feng et al. 2016, Protic et al. 2016).

There is considerable variation in total collagen content and interstitial collagen types within and among individual fibroids. In other tissues that have been studied, the fibrotic process involves the release of multiple growth factors, cytokines (Gabbiani et al. 2003), and enzymes such as metalloproteinases. The myriad changes in these factors in uterine fibroid tissue are also associated with the fibrotic process in uterine fibroids.

Fibroid pathobiology and biochemistry is difficult to study as there is no universally accepted animal model for this tumor. (Taylor et al. 2015). In addition, the nature of the tumor (whether it is growing, regressing or its age) is not ascertained. Understanding of these tumors, therefore, will continue to be based on studies utilizing uterine fibroid tissue obtained from women following surgery. Heterogeneity among and within uterine fibroids has been described at many levels and especially genetic heterogeneity seems to be an obvious grouping factor. The structural differences described here are easily observed upon collection of the fibroids.

Documentation of the heterogeneity among and within fibroids has important ramifications for the design and interpretation of cell culture studies as well. Studies utilizing cell culture or cell lines reflect only the characteristics of the tumor or the part of the tumor from which the culture or cell line was derived and are thus not representative of all fibroid tumors (Markowski et al. 2010) or all regions within the same fibroid. Fibroids usually contain regions with high amounts of ECM/low cellularity and other regions with greater cellularity; fewer cells can be isolated from the former. Therefore, cell cultures derived from heterogeneous fibroid tissue will be enriched in cells from the high cellularity regions of that fibroid and contain fewer cells from the high ECM regions. Experiments performed with this mixed cell population will not adequately represent the characteristics of the cells underrepresented in this mix, and thus many of the cell culture experiments reported in the literature underrepresent the cells from high ECM areas of the fibroid. One must keep in mind that different areas of the same fibroid may be in varied physiological stages of development. Therefore, cell populations may be dissimilar due to differences in the biomechanical signaling environments from which they were derived.

The present study revealed heterogeneity among and within uterine fibroids as revealed by differences in total collagen, collagen types, gross appearance, and mechanical variations.

Our understanding of fibroid pathophysiology is enhanced through the investigation of a) growth factors, collagen content, collagen types, and collagen cross-links to understand the complexity of the chemical and biochemical signaling in fibroid development; b) the correlation of biochemical and mechanical properties to more precisely understand mechanical signaling in uterine fibroids; and c) the mechanical forces involved in fibroid development as affected by the various components of the ECM.

Example 11

Nineteen patients with fibroids were screened, all of whom planned a hysterectomy, and 15 women met the study's eligibility criteria and were enrolled. The average age of the study subjects was 44.7±2.6 years. The ratio of black to white women was 3:2, similar to the race ratio in epidemiology of fibroids.

A stepped dosage was used. Three subjects (Group 1) received 1.16 mg of EN3835, regardless of fibroid size. Approximately 50-70 microliters volume of collagenase was injected for each 1 $cm^3$ fibroid volume, to a maximum volume of 1.676 ml/fibroid regardless of fibroid volume. For Group 1, samples were studied at 24-48 hours after injection. For Group 2 subjects, all samples were removed 60 days following injection with CCFI. For this group an injection volume of 0.05 ml/cm$^3$ of fibroid volume was used. Group 2 (n=9) was further divided into three subgroups (n=3/subgroup), each subgroup receiving a higher dose of the study drug than the last subgroup (1.68, 3.35, and 5.028 mg, respectively, as the maximum doses). A dose-dependent effect was observed in new results as described below.

Figure 32:
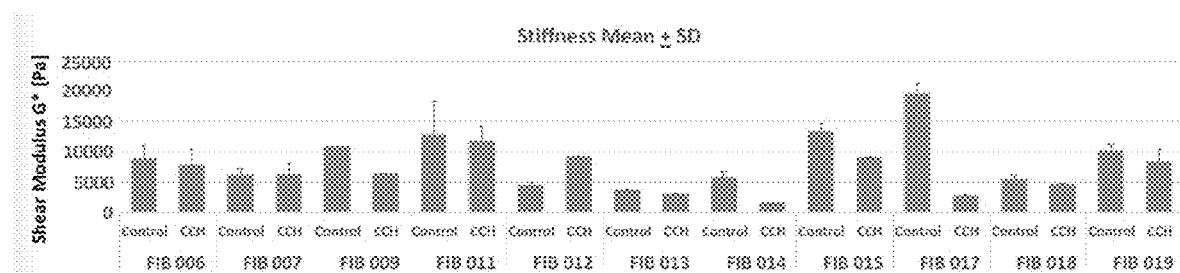
FIG. 32. Tissue samples injected with collagenase, EN3835 (CCH) or patient-matched control samples (Control) were cored with 8 mm diameter punch, trimmed to a 2 mm height and strain sweep was performed on each sample to ensure linearity at selected strain: 10 rad/sec—0.1 to 1.0% strain. Complex shear modulus (G*) in [Pa] at 5, 7, and 10 rad/sec were measured. Data from 1st frequency sweep at 7 rad/sec are shown (+SD). Injection of collagenase led to a significant reduction in stiffness (p<0.05) in treated versus control samples for fibroids (FIB) in study samples. Numbers (eg, FIB 017) correspond to the numbers of the study subjects. Group 1=FIB 006 and FIB 007. FIB 008 is not present because the sample was removed in piecemeal at surgery (morcellated) and could not be analyzed. Group 2=FIB 009 through 019, with each 3 samples reflecting an increase in CCH dosage.

Treated fibroid tissues were noticeably soft to palpation on gross examination. Some samples injected with higher dosages of CCFI showed liquefaction at the area of injection. The digestion of collagen did not extend beyond the pseudocapsule of any fibroid. Notably, the fibroids differed in stiffness, but injection with EN3835 led to a reduction in stiffness (FIG. 32). The stiffness was variable and in all but one sample, injection of EN3835 led to a reduction in stiffness, though a dose-dependent effect was not observed for this assay.

To confirm whether injection of collagenase leads to cell responses in the fibroid, differences in markers of cell death (apoptosis and autophagy), and a cell proliferation marker (PCNA) were assessed. For these studies, immunofluorescence examination of study samples proved superior to immuno-histochemical stains.

Figure 33:
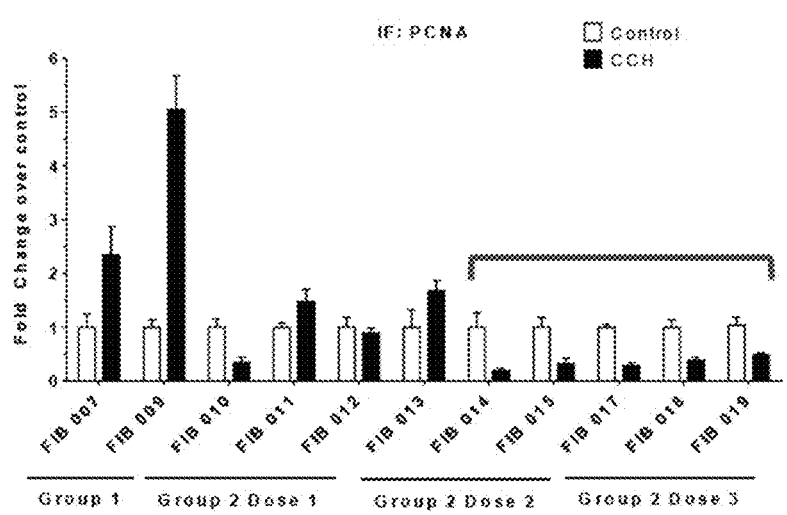
FIG. 33. Reduced levels of the proliferation marker, PCNA, in CCH-treated fibroids. PCNA expression was measured in control (open bars) or collagenase-treated fibroid samples (black bars). CCH injection increased PCNA expression in 2 out of 2 subjects in 24-48 hrs treatment group, and decreased in 6 out of 9 subjects in 6090 days at higher doses (Group 2, dose 3). Levels of PCNA expression were quantified by immunofluorescence and Image J analysis. Data=mean±SD of 5 images (20×). Red bar shows reduction at higher doses of CCH.

PCNA was used to assess changes in cell proliferation. Notably, PCNA staining was increased at 24-48 hours after EN3835 injection (Group 1), but was decreased in fibroids 60 days following EN3835 injection (Group 2; FIG. 33). Notably, there was a dose-dependent effect as the fibroids at the highest doses showed significant reduction in PCNA expression (FIB samples 014-019, FIG. 33). This important finding suggests that injection with collagenase led to a reduced cell proliferation in the EN3835-injected fibroid tissues at 60-90 days and would favor regression of the fibroid tumors.

When the dose per sample was analyzed, there appeared to be a dose-dependent effect for collagenase at levels in Group 2-dose 2 and Group 2-dose 3. The doses per mg of tissue are shown in FIG. 34. Taken together with the results in FIG. 33, the data suggest that at 2-3 mg injected (or 0.42-0.94 mg/cm3), there was a reduction in the proliferation marker, PCNA. A reduction in PCNA would suggest that, over time, the fibroids treated with this dose undergo a regression, or at least a stabilization in size.

Interestingly, staining for the autophagy marker, LC3B (FIG. 35), showed a several fold increase in the collagenase-treated samples. Given the fold increase in the autophagy marker, this observation suggests that collagenase treatment activates autophagic cell death, which also favors a long-term reduction in fibroid size.

Figure 36:
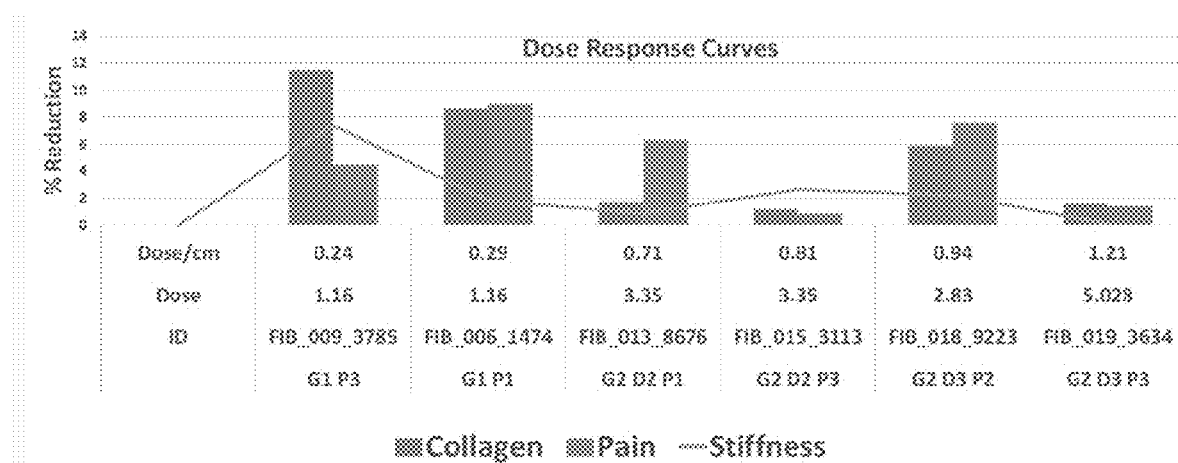
FIG. 36. Quantification of pain in women before and after injection with collagenase, by dose of study drug, and size of fibroid and stiffness. For this graph, we only considered women with pain at baseline and the McGill Questionnaire data. Group 1, no subject reported an increase in pain between baseline and 24-48 hours post injection. For Group 2, only one of the nine subjects reported an increase in pain by one point between baseline (FIB 013) and 4-8 days post study drug injection (p=0.057) and no increase in pain was reported at day 60-90 post study drug injection (pre-hysterectomy, p=0.079). On average there was a 14 point reduction in pain at 4-8 days for the other eight subjects in Group 2, and the trend continued for all subjects with an average 15 point reduction at 60-90 days from baseline. G=Group; D=Dose; Dose varied by fibroid size in Group 3. Y-axis=% Reduction.

No significant adverse events were reported for injecting EN3835 into uterine fibroids. Notably, eight out of nine subjects in Group 2 reported a reduction in fibroid related pain at both the 4-8 day and 60 to 90-day post-injection time points, as determined by the McGill Pain Questionnaire (FIG. 36).

Figure 35:
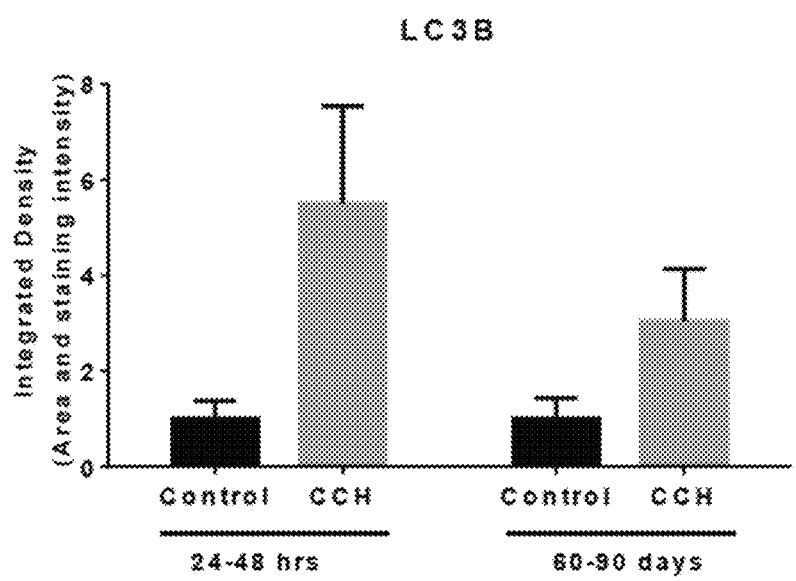
FIG. 35. Autophagic cell death in collagenase-treated fibroid tissues. Injection of fibroids with EN3835 increased LC3B expression by 5.5±2.0 fold at 24-48 hrs treatment group, and by 3.0±1.1 fold in 60-90 days treatment groups. While the changes were not significant (p<0.11), the fold changes are consistent with a treatment effect. Expression levels of the autophagic cell death marker LC3B were quantified by immunofluorescence and Image J analysis. Data are presented as mean±SD of 2 fibroid subjects (for 24-48 hrs), and 9 subjects (for 60-90 days). CCH=collagenase, EN3835.

In summary, injection of fibroids with collagenase is possible and is associated with a significant reduction in mechanical stiffness of the injected fibroid. This decreased stiffness was accompanied by a reduction in collagen density. Dose-dependent changes in cell proliferation marker, PCNA, were observed with a reduction in proliferation at the higher collagenase doses (FIG. 33). Thus, EN3835 treatment may lead to a reduction in fibroid size. This finding is accompanied by the observation of an increase in the autophagy marker, LC3B (FIG. 35). Based on reduction in proliferation, a dosage of at 2-3 mg injected (or 0.42-0.94 mg/cm$^3$) appears sufficient for beneficial tissue effects.

The patent and scientific literature referred to herein establishes the knowledge that is available to those with skill in the art. All United States patents and published or unpublished United States patent applications cited herein are incorporated by reference in their entireties for all purposes. All published foreign patents and patent applications cited herein are hereby incorporated by reference in their entireties for all purposes. All other published references, documents, manuscripts and scientific literature cited herein are hereby incorporated by reference in their entireties for all purposes.

While this invention has been particularly shown and described with references to preferred embodiments thereof, it will be understood by those skilled in the art that various changes in form and details may be made therein without departing from the scope of the invention encompassed by the appended claims.

REFERENCES

Abedin et al., Biochem Biophys Res Commun 1981; 102(4): 1237-1245.
Aitken et al., Flum. Reprod. 2006; 21 (10): 2669-2678.
Arici et al., Fertil Steril 2000; 73(5): 1006-1011.
Arslan et al., Hum Reprod 2005; 20(4): 852-863.
Aviles et al., Advances in Uterine Leiomyoma Research: 3rd NIH International Congress, 2010.
Badalamente M A, Hurst L C. Efficacy and safety of injectable mixed collagenase subtypes in the treatment of Dupuytren's contracture. J Hand Surg Am. 2007; 32(6): 767-774.
Bae et al., Pharm Res 1991; 8(4): 531-537.
Baird D D, Dunson D B, Hill M C, Cousins D, Schectman J M. High cumulative incidence of uterine leiomyoma in black and white women: ultrasound evidence. Am J Obstet Gynecol 2003; 188(1):100e7.
Barker N M, Carrino D A, Caplan A I, Hurd W W, Liu J H, Tan H, et al. Proteoglycans in Leiomyoma and Normal Myometrium: Abundance, Steroid Hormone Control, and Implications for Pathophysiology. Reprod Sci. 2016; 23(3):302-9. Epub 2015/10/02. 10.1177/1933719115607994.
Barrett J C. Molecular Characterization of Uterine Leiomyoma. In: Presented at: Advances in Leiomyoma Research: 2nd NIH Int'l Congress. Bethesda, MD; 2005.
Behera M A, Feng L, Yonish B, Catherino W, Jung S H, Leppert P C. Thrombospondin-1 and Thrombospondin-2 mRNA and TSP-1 and TSP-2 Protein Expression in Uterine Fibroids and Correlation to the Genes COL1A1 and COL3A1 and to the Collagen Cross-link Hydroxyproline. Reprod Sci. 2007; 14(8_suppl):63-76.
Berto A G A, Sampaio L O, Franco C R C, Cesar R M, Michelacci Y M. A comparative analysis of structure and spatial distribution of decorin in human leiomyoma and normal myometrium. Biochim Biophys Acta—Gen Subj. 2003; 1619(1):98-112.
Bolgen et al., Biomater Sci Polym Ed 2007; 18(9): 1165-1179.
Borth W, Menzel E J, Salzer M, Steffen C. Human serum inhibitors of collagenase as revealed by preparative iso-electric focusing. Clin Chim Acta. 1981; 117(2):219-225.
Bouwsma E V, Hesley G K, Woodrum D A, et al. Comparing focused ultrasound and uterine artery embolization for uterine fibroids-rationale and design of the Fibroid Interventions: reducing symptoms today and tomorrow (FIRSTT) trial. *Fertil Steril.* 2011; 96(3):704-710. doi: 10.1016/j.fertnstert.2011.06.062.

Breech et al., "Leiomyomata uteri and myomectomy". In: TeLinde's Operative Gynecology, 9th ed. Philadelphia: Lippincott, Williams and Wilkins; 2003: 753-799.

Bromley J W, Osman M, Steinlauf P, Gennace T, Stern H. Collagenase: an experimental study of intervertebral disc dissolution. Spine. 1980; 5(2):126-136.

Brunengraber L N, Jayes F L, Leppert P C. Injectable *Clostridium histolyticum* collagenase as a potential treatment for uterine fibroids. Reprod Sci. 2014; 21 (12):1452-1459. doi:10.1177/1933719114553449.

Cardozo E R, Clark A D, Banks N K, Flenne M B, Stegmann B J, Segars J H. The estimated annual cost of uterine leiomyomata in the United States. Am J Obstet Gynecol 2012; 206(03):211. e 1-211, e9.

Catherino W F I, "Annual Meeting of the American Society for Reproductive Medicine." 42nd Annual Postgraduate Program 2009: P 35.

Catherino W F I, Segars J H. Microarray analysis in fibroids: which gene list is the correct list? Fertil Steril. 2003; 80(2):293-4. Epub 2003/08/12.

Catherino W F I, Leppert P C, Stenmark M H, et al. Reduced dermatopontin expression is a molecular link between uterine leiomyomas and keloids. Genes Chromosom Cancer. 2004; 40(3):204-217.

Chen et al., J Clin Endocrinol Metab. 2006 April; 91 (4):1296-304.

Chudnoff S G, Berman J M, Levine D J, Harris M, Guido R S, Banks E. Outpatient procedure for the treatment and relief of symptomatic uterine myomas. Obstet Gynecol. 2013 May; 121 (5):1075-82.

Chung et al., J Biol Chem 2008; 283(38): 25879-25886.

Chwalisz et al., Endocrine Reviews 2005; 26(3): 423-438.

Chwalisz et al., Fertility & Sterility 2007; 87(6): 1399-1412.

Coyne K S, Harrington A, Currie B M, Mo Y, Gillard P, Spies J. A meaningful response on the uterine fibroid symptom and health-related quality of life questionnaire (UFS-QOL). *Fertil Steril.* 2018; 110(4):e135-e136.doi: 10.1016/j.fertnstert.2018.07.402.

Cramer S F, Patel A. The frequency of uterine leiomyomas. Am J Clin Pathol. 1990; 94(4):435-8. Epub 1990/10/01.

D'Angelo E, Quade B J, Prat J. Uterine Smooth Muscles Tumors In: Mutter G L, Prat J, editors. Pathology of the Female Reproductive Tract. 3rd ed Edinburgh: Churchill Livingstone/Elsevier; 2014. p. 402-24.

Das et al., Endocrinology 1992; 130(6): 3459-3466.

Drayer S M, Catherino W H. Prevalence, morbidity, and current medical management of uterine leiomyomas. Int J Gynaecol Obstet 2015; 131 (02):117-122.

Evans J P, Leppert P C. "Feeling the force" in reproduction: Mechanotransduction in reproductive processes. Connect Tissue Res. 2016; 57(3):236-44. Epub 2016/04/14. 10.3109/03008207.2016.1146715.

Feng L, Jayes F L, Johnson L N C, Schomberg D W, Leppert P C. Biochemical Pathways and Myometrial Cell Differentiation Leading to Nodule Formation Containing Collagen and Fibronectin. Curr Protein Pept Sci. 2016; 18(2): 155-66. Epub 2016/03/24. 10.2174/1389203717666160322145731.

Feng C, Meldrum S, Fiscella K. Improved quality of life is partly explained by fewer symptoms after treatment of fibroids with mifepristone. *Int J Gynaecol Obstet.* 2010; 109(2):121-124. doi:10.1016/j.ijgo.2009.11.019.

Feng et al., Reproductive Sciences 17, 3; 711, 2010.

Feng et al., Thrombospondin-1 in an early uterine fibroid development model. American Society for Matrix Biology Biennial Meeting 2008; Abstract #168.

Fennessy F M, Kong C Y, Tempany C M, Swan J S. Quality-of-life assessment of fibroid treatment options and outcomes. *Radiology.* 2011; 259(3):785-792. doi: 10.1148/radiol111100704.

Flake G P, Moore A B, Sutton D, et al. The natural history of uterine leiomyomas: light and electron microscopic studies of fibroid phases, interstitial ischemia, inanosis, and reclamation. Obstet Gynecol Int. 2013; 2013:528376.

Flake G P, Moore A B, Flagler N, Wicker B, Clayton N, Kissling G E, et al. The natural history of uterine leiomyomas: morphometric concordance with concepts of interstitial ischemia and inanosis. Obstet Gynecol Int. 2013; 2013:285103 Epub 2013/11/08. 10.1155/2013/285103.

Frey and Flaag, Rev. Mol. Biotechnol. 2002; 90: 257-267.

Friedman K, Poliak S V, Manning T, Pennell S R. Degradation of porcine dermal connective tissue by collagenase and by hyaluronidase. Br J Dermatol. 1986; 115(4):403-408.

Gabbiani G. The myofibroblast in wound healing and fibrocontractive diseases. J Pathol. 2003; 200(4):500-3. Epub 2003/07/08. 10.1002/path.1427.

Gabbiani G, Le Lous M, Bailey A J, Bazin S, Delaunay A. Collagen and myofibroblasts of granulation tissue. A chemical, ultrastructural and immunologic study. Virchows Arch B Cell Pathol. 1976; 21 (2):133-45. Epub 1976/08/11.

Geever et al., Eur Polym J 2006 42(1): 69-80.

Gelbard M, Goldstein I, Flellstrom W J, et al. Clinical efficacy, safety, and tolerability of collagenase *Clostridium histolyticum* for the treatment of peyronie disease in 2 large double-blind, randomized, placebo controlled phase 3 studies. J Urol. 2013; 190(1):199-207. doi: 10.1016/j.juro.2013.01.087.

Giray B, Esim-Buyukbayrak E, Flallac-Keser S, Karageyim-Karsidag A Y, Turkgeldi A. Comparison of Nerve Fiber Density between Patients with Uterine Leiomyoma with and without Pain: a Prospective Clinical Study. *Geburtshilfe Frauenheilkd.* 2018; 78(4):407-411. doi:10.1055/a-0591-1751.

Graham et al., Nucleic Acid Res 1993; 21 (16): 3737-3743.

Han S, Makareeva E, Kuznetsova N V, et al. Molecular mechanism of type I collagen homotrimer resistance to mammalian collagenases. J Biol Chem. 2010; 285(29): 22276-22281.

Harding G, Coyne K S, Thompson C L, Spies J B. The responsiveness of the uterine fibroid symptom and health-related quality of life questionnaire (UFS-QOL). *Health Qual Life Outcomes.* 2008; 6:99. Published 2008 Nov. 12. doi:10.1186/1477-7525-6-99.

Hatefi et al., Journal of controlled Release 2002 80(1-3): 9-28.

Heinonen H R, Pasanen A, Heikinheimo O, Tanskanen T, Palin K, Tolvanen J, et al. Multiple clinical characteristics separate MED12-mutation-positive and -negative uterine leiomyomas. Sci Rep. 2017; 7(1):1015 Epub 2017/04/23. 10.1038/S41598-017-01199-0.

Heinonen H R, Mehine M, Makinen N, Pasanen A, Pitkanen E, Karhu A, et al. Global metabolomic profiling of uterine leiomyomas. Br J Cancer. 2017; 117(12):1855-64. Epub 2017/10/27. 10.1038/bjc.2017.361.

Hennessy et al., Lancet Oncol 2004; 5(6): 341-353.

Heskins M, Guillet J E; J Macromol Sci. Part A—Chem 1968; 2(8): 1441-1455.

Ho Y Y, Lagares D, Tager A M, Kapoor M. Fibrosis—a lethal component of systemic sclerosis. Nat Rev Rheumatol. 2014; 10(7):390-402. Epub 2014/04/23. 10.1038/nrrheum.2014.53.

Hodge J C, Quade B J, Rubin M A, Stewart E A, Dal Cin P, Morton C C. Molecular and cytogenetic characterization of plexiform leiomyomata provide further evidence for genetic heterogeneity underlying uterine fibroids. Am J Pathol. 2008; 172(5):1403-10. Epub 2008/04/12. 10.2353/ajpath.2008.071102.

Holdsworth-Carson S J, Zhao D, Cann L, Bittinger S, Nowell C J, Rogers P A. Differences in the cellular composition of small versus large uterine fibroids. Reproduction (Cambridge, England). 2016; 152(5):467-80. Epub 2016/08/17. 10.1530/rep-16-0216.

Huang et al., Macromolecules 2008; 41 (22): 8339-8345.

Ibraheem et al., Towards water-soluble star copolymer-drug conjugates. Proc. of 58th Conf. of South East Regional Amer. Chem. Society, Nov. 1-4, 2006, Augusta GA.

Islam M S, Ciavattini A, Petraglia F, Castellucci M, Ciarmela P. Extracellular matrix in uterine leiomyoma pathogenesis: a potential target for future therapeutics. Hum Reprod Update. 2018; 24(1):59-85. Epub 2017/12/01. 10.1093/humupd/dmx032.

Jamaluddin M F B, Ko Y A, Kumar M, Brown Y, Bajwa P, Nagendra P B, et al. Proteomic Profiling of Human Uterine Fibroids Reveals Upregulation of the Extracellular Matrix Protein Periostin. Endocrinology. 2018; 159 (2):1106-18. Epub 2017/12/16. 10.1210/en.2017-03018.

Jamaluddin M F B, Nahar P, Tanwar P S. Proteomic Characterization of the Extracellular Matrix of Human Uterine Fibroids. Endocrinology. 2018; 159(7):2656-69. Epub 2018/05/23. 10.1210/en.2018-00151.

Jayes F L, Liu B, Feng L, Aviles-Espinoza N, Leikin S, et al. (2019) Evidence of biomechanical and collagen heterogeneity in uterine fibroids. PLOS ONE 14(4): e0215646.

Jayes F L, Liu B, Moutos F T, Kuchibhatla M, Guilak F, Leppert P C. Loss of stiffness in collagen-rich uterine fibroids after digestion with purified collagenase *Clostridium histolyticum*. Am J Obstet Gynecol. 2016; 215(5):596.e1-596.e8. doi:10.1016/j.ajog.2016.05.006.

Jemal et al., Cancer statistics, 2005. CA Cancer J Clin 2005; 55(1): 10-30.

Jenison et al., Antisense & Nucleic Acid Drug Dev., 1998; 8(4): 265-279.

Joffe et al., Mod Pathol 2009; 22(3): 450-459.

Jorge S, Chang S, Barzilai J J, Leppert P, Segars J H. Mechanical signaling in reproductive tissues: mechanisms and importance. Reprod Sci. 2014; 21 (9):1093-107 Epub 2014/07/09. 10.1177/1933719114542023.

Joseph et al., Fertil Steril 2010; 93(5):1500-8.

Kainthan et al., Macromolecules 2006; 39(22): 7708-7717.

Kamel M, Wagih M, Kilic G S, Diaz-Arrastia C R, Baraka M A, Salama S A. Overhydroxylation of Lysine of Collagen Increases Uterine Fibroids Proliferation: Roles of Lysyl Hydroxylases, Lysyl Oxidases, and Matrix Metalloproteinases. Biomed Res Int. 2017, 2017:5316845. Epub 2017/10/31. 10.1155/2017/5316845

Kao et al., Connect Tissue Res 1977; 5(2): 127-129.

Kohori et al., Journal of Controlled Release 1998; 55(1): 87-98.

Konishi I, Fujii S, Ban C, Okuda Y, Okamura H, Tojo S. Ultrastructural study of minute uterine leiomyomas. Int J Gynecol Pathol. 1983; 2(2):113-20. Epub 1983/01/01.

Kose O, Waseem A., Dermatol Surg 2008; 34(3): 336-346.

Kuroda et al., J Invest Dermatol 1999; 112(5): 706-710.

Lacomb R, Nadiarnykh O, Townsend S S, Campagnola P J. Phase Matching considerations in Second Harmonic Generation from tissues: Effects on emission directionality, conversion efficiency and observed morphology. *Opt Commun.* 2008; 281 (7):1823-1832. doi:10.1016/j.optcom.2007.10.040.

Latha B, Ramakrishnan M, Jayaraman V, Babu M. Physicochemical properties of extracellular matrix proteins in post-burn human granulation tissue. Comp Biochem Physiol B Biochem Mol Biol. 1999; 124(3):241-9. Epub 2000/01/13.

Laughlin et al. (2009) Obstet. Gynecol. 113:630.

Lee B H, Vernon B, Macromol Biosci 2005; 5(7): 629-635.

Lee B S, Nowak R A., J Clin Endocrinol Metab 2001; 86(2): 913-920.

Leppert et al., American Journal of Obstetrics and Gynecology 195(6): 415-420, 2006. Leppert P C, Baginski T, Prupas C, Catherino W H, Pletcher S, Segars J H. Comparative ultrastructure of collagen fibrils in uterine leiomyomas and normal myometrium. Fertil Steril. 2004; 82(SUPPL. 3):1182-1187.

Leppert P C, Jayes F L, Segars J H. The extracellular matrix contributes to mechanotransduction in uterine fibroids. Obstet Gynecol Int. 2014; 2014:783289. doi: 10.1155/2014/783289.

Le Ray et al., J. Pharm. Sci. 1994; 83(6): 845-851.

Makareeva E, Han S, Vera J C, Sackett D L, Holmbeck K, Phillips C L, et al. Carcinomas contain a matrix metalloproteinase-resistant isoform of type I collagen exerting selective support to invasion. Cancer Res. 2010; 70(11): 4366-74. Epub 2010/05/13. 10.1158/0008-5472.CAN-09-4057.

Makinen N, Mehine M, Tolvanen J, Kaasinen E, Li Y, Lehtonen H J, et al. MED12, the mediator complex subunit 12 gene, is mutated at high frequency in uterine leiomyomas. Science. 2011; 334(6053):252-5. Epub 2011/08/27. 10.1126/science. 1208930.

Malik M, Catherino W H., Fertil Steril 2007; 87(5): 1166-1172.

Malik M, Norian J, McCarthy-Keith D, Britten J, Catherino W H. Why leiomyomas are called fibroids: the central role of extracellular matrix in symptomatic women. Semin Reprod Med. 2010; 28(3):169-79. Epub 2010/04/24. 10.1055/S-0030-1251475.

Malik et al. Matrix Biol. (2012) 31 (7-8):389-97.

Mallya S K, Mookhtiar K A, van Wart H E. Kinetics of hydrolysis of type I, II, and III collagens by the class I and II *Clostridium histolyticum* collagenases. J Protein Chem. 1992; 11 (1):99-107.

Markowski D N, Bartnitzke S, Beige G, Drieschner N, Helmke B M, Bullerdiek J. Cell culture and senescence in uterine fibroids. Cancer Genet Cytogenet. 2010; 202(1): 53-7. Epub 2010/09/02. 10.1016/j.cancergencyto.2010.06.010.

Marsh et al. (2013) Fertil. Steril. 99(7):1951-1957.

Matchar et al., Evid Rep Technol Assess (Summ) 2001 (34): 1-6.

McCarthy-Keith D M, Malik M, Britten J, Segars J, Catherino W H. Gonadotropin-releasing hormone agonist increases expression of osmotic response genes in leiomyoma cells. Fertil Steril. 2011; 95(7):2383-7. Epub 2011/04/19.

McGuire M M, Yatsenko A, Hoffner L, Jones M, Surti U, Rajkovic A. Whole exome sequencing in a random sample of North American women with leiomyomas identifies MED12 mutations in majority of uterine leiomyomas. PLoS One. 2012; 7(3):e33251 Epub 2012/03/20. 10.1371/journal.pone.0033251.

Mehine M, Kaasinen E, Makinen N, Katainen R, Kampjarvi K, Pitkanen E, et al. Characterization of uterine leiomyomas by whole-genome sequencing. N Engl J Med. 2013; 369(1):43-53. Epub 2013/06/07. 10.1056/NEJMoa1302736.

Mehine M, Heinonen H-R, Sarvilinna N, Pitkanen E, Makinen N, Katainen R, et al. Clonally related uterine leiomyomas are common and display branched tumor evolution. Hum Mol Genet. 2015; 24(15):4407-16. Epub 2015/05/13. 10.1093/hmg/ddv177.

Mitsiades et al., Cancer Cell 2004; 6(5): 439-444.

Miyabashi T, Lord P F, Dubiolzig P R, Biller D S, Manley P A. Chemonucleolysis with collagenase: a radiographic and pathologic study in dogs. Vet Surg. 1992; 21 (3):189-194.

Moulin et al., J Cell Physiol 2004; 198(3): 350-358.

Mulabecirovic A., et al. (2016) Ultrasound in Med. and Biol. 42(11):2572-2588.

Munro M G. Uterine leiomyomas, current concepts: pathogenesis, impact on reproductive health, and medical, procedural, and surgical management. Obstet Gynecol Clin North Am. 2011; 38(4):703-731.

Nagase H, Itoh Y, Binner S. Interaction of alpha 2-macroglobulin with matrix metalloproteinases and its use for identification of their active forms. Ann N Y Acad Sci. 1994; 732:294-302.

Naitoh et al., Genes Cells 2005; 10(11): 1081-1091.

Ng. et al. J. Clin. Endocrinol. Metab. (2019) 104(3):970-980.

Norian J M, Owen C M, Taboas J, et al. Characterization of tissue biomechanics and mechanical signaling in uterine leiomyoma. Matrix Biol. 2012; 31 (1):57-65. doi: 10.1016/j.matbio.2011.09.001.

Norian et al., Reproductive Sciences 2007; 14: 79A.

Norian et al., Reprod Sci 2009 16(12): 1153-1164.

Oudshoorn et al., Biomaterials 2006; 27(32): 5471-5479.

Paluch E K, Nelson C M, Biais N, Fabry B, Moeller J, Pruitt B L, et al. Mechanotransduction: use the force(s). BMC Biol. 2015; 13:47 Epub 2015/07/05. 10.1186/S12915-015-0150-4.

Peddada et al., Proc Natl Acad Sci USA 2008; 105(50): 19887-19892.

Pfaffl M W. Nucleic Acids Res 2001; 29(9): e45.

Protic O, Toti P, Islam M S, Occhini R, Giannubilo S R, Catherino W H, et al. Possible involvement of inflammatory/reparative processes in the development of uterine fibroids. Cell Tissue Res. 2016; 364(2):415-27. Epub 2015/11/29. 10.1007/s00441-015-2324-3.

Rogers et al., Am. J. Obstet. Gynecol. 2008; 198(4): 474.e1-11.

Sabry M, Al-Hendy A. Medical treatment of uterine leiomyoma. Reprod Sci. 2012; 19(4):339-353.

Sasaki et al., J Clin Endocrinol Metab 2007; 92(2): 616-623.

Schindelin, J.; Arganda-Carreras, I. & Frise, E. et al. (2012), "Fiji: an open-source platform for biological-image analysis", Nature methods 9(7): 676-682.

Schmittgen T D, Zakrajsek B A. J Biochem Biophys Methods 2000; 46(1-2): 69-81.

Sigrist, R. M. S.; Liau, J., Kaffas, A. E., Chammas, M. C., Willmann, J. K. (2017) Theranostics 7(5):1303-1329.

Sosic et al., J Gynaecol Obstet 1996; 54: 245-250.

Spies J B, Coyne K, Guaou Guaou N, Boyle D, Skyrnarz-Murphy K, Gonzalves S M. The UFS-QOL, a new disease-specific symptom and health-related quality of life questionnaire for leiomyomata. Obstet Gynecol. 2002; 99(2):290-300.

Stewart E A, Laughlin-Tommaso S K, Catherino W H, Lalitkumar S, Gupta D, Vollenhoven B. Uterine fibroids. Nat Rev Dis Primers. 2016; 2:16043 Epub 2016/06/24. 10.1038/nrdp.2016.43.

Stewart E A, Friedman A J, Peck K, Nowak R A. Relative overexpression of collagen type I and collagen type III messenger ribonucleic acids by uterine leiomyomas during the proliferative phase of the menstrual cycle. J Clin Endocrinol Metab. 1994; 79(3):900-6. Epub 1994/09/01. 10.1210/jcem 0.79.3.8077380.

Sunder et al., Macromolecules 1999; 32(13): 4240-4246.

Takamoto et al., Connect Tissue Res 1998; 37(3-4): 163-175.

Taylor D K, Holthouser K, Segars J H, Leppert P C. Recent scientific advances in leiomyoma (uterine fibroids) research facilitates better understanding and management. FIOOORes. 2015; 4(F1000 Faculty Rev):183 Epub 2015/08/04. 10.12688/f1000research.6189.1.

Taylor D K, "The Flyperbranched Polyglycerol Platform: Approaching the ideal-drug delivery system." Proceedings of Abstracts for Duke University Research Day May 6, 2009, Duke University.

Taylor D K, Leppert P C. Treatment for uterine fibroids: searching for effective drug therapies. Drug Discov Today Ther Strateg. 2012; 9(1):e41-e49.

Thomas A, Bayat A. The emerging role of *Clostridium histolyticum* collagenase in the treatment of Dupuytren disease. Ther Clin Risk Manag. 2010; 6:557-572.

Thorne J T, Segal T R, Chang S, Jorge S, Segars J H, Leppert P C. Dynamic reciprocity between cells and their microenvironment in reproduction. Biol Reprod. 2015; 92(1):25, 1-10. Epub 2014/11/21. 10.1095/biolreprod.114.121368.

Toyoshima T, Matsushita O, Minami J, Nishi N, Okabe A, Itano T. Collagen-binding domain of a *Clostridium histolyticum* collagenase exhibits a broad substrate spectrum both in vitro and in vivo. Connect Tissue Res. 2001; 42(4):281-290.

Trueb B, Bornstein P, J Biol Chem 1984; 259(13): 8597-8604.

Tsibris J C, Segars J, Coppola D, Mane S, Wilbanks G D, O'Brien W F, et al. Insights from gene arrays on the development and growth regulation of uterine leiomyomata. Fertil Steril. 2002; 78(1):114-21. Epub 2002/07/04.

Uhler C, Shivashankar G V. Regulation of genome organization and gene expression by nuclear mechanotransduction. Nat Rev Mol Cell Biol. 2017; 18(12):717-27. Epub 2017/10/19. 10.1038/nrm.2017.101.

Walocha et al., Hum Reprod 2003; 18(5): 1088-1093.

Wang et al., Hum Reprod 2006; 21 (7): 1869-1877.

Wei et al., Fertil Steril 2006, 85(1): 179-187.

Weston et al., Mol Hum Reprod 2003; 9(9): 541-549.

Wu et al., Cochrane Database Syst Rev. 2007: CD005287.

Wu et al., Matrix Biol 2005; 24(1): 3-13.

Xu et al., J Clin Endocrinol Metab 2005; 90: 953-961.

Yatsenko S A, Mittal P, Wood-Trageser M A, Jones M W, Surti U, Edwards R P, et al. Highly heterogeneous genomic landscape of uterine leiomyomas by whole exome sequencing and genome-wide arrays. Fertil Steril. 2017; 107(2):457-66. Epub 2016/11/23. 10.1016/j.fertnstert.2016.10.035.

Yu et al., Proc Soc Exp Biol Med 1995; 209: 360-368.

Zhao et al., Mol Hum Reprod 2007; 13: 343-349.

The invention claimed is:

1. A method for reducing the size of a uterine fibroid in a patient, the method comprising:
   administering into the uterine fibroid a composition comprising *Clostridium histolyticum* collagenase I and collagenase II in a 1:1 mass ratio to thereby reduce the size of the uterine fibroid, wherein there is an at least two fold increase in LC3B expression within the uterine fibroid as measured at 60 days following the administration.

2. The method of claim 1, wherein said composition is delivered through a delivery channel into said fibroid, wherein the delivery channel is in a needle, syringe, cannula, catheter or jet injector.

3. The method of claim 1, wherein about 0.005 mg to about 10 mg collagenase is administered per cm³ of tissue to be treated.

4. The method of claim 1, wherein about 0.05 mg to about 1 mg collagenase is administered per cm³ of tissue to be treated.

5. The method of claim 1, wherein about 0.25 mg to about 1 mg collagenase is administered per cm³ of tissue to be treated.

6. The method of claim 1, wherein the method results in an at least three fold reduction in expression of proliferating cell nuclear antigen (PCNA) as measured at 60 days following the administration.

7. A method for reducing pain associated with a uterine fibroid in a patient, the method comprising:
   administering into the uterine fibroid in the patient a composition comprising *Clostridium histolyticum* collagenase I and collagenase II in a 1:1 mass ratio to thereby reduce the pain associated with the uterine fibroid, wherein the patient has a reduction of at least 1 point on the McGill Pain Scale as measured at 60 days following the administration.

8. The method of claim 7, wherein said composition is delivered through a delivery channel into said fibroid, wherein the delivery channel is in a needle, syringe, cannula, catheter or jet injector.

9. The method of claim 7, wherein about 0.005 mg to about 10 mg collagenase is administered per cm³ of tissue to be treated.

10. The method of claim 7, wherein about 0.05 mg to about 1 mg collagenase is administered per cm³ of tissue to be treated.

11. The method of claim 7, wherein about 0.25 mg to about 1 mg collagenase is administered per cm³ of tissue to be treated.

12. The method of claim 7, wherein at 60 days following the administering the patient has a reduction of about 15 points on the McGill Pain Scale.

* * * * *

SEQUENCE LISTING

<160> NUMBER OF SEQ ID NOS: 2

<210> SEQ ID NO 1
<211> LENGTH: 1118
<212> TYPE: PRT
<213> ORGANISM: Clostridium histolyticum

<400> SEQUENCE: 1

```
Met Lys Lys Asn Ile Leu Lys Ile Leu Met Asp Ser Tyr Ser Lys Glu
1               5                   10                  15

Ser Lys Ile Gln Thr Val Arg Arg Val Thr Ser Val Ser Leu Leu Ala
            20                  25                  30

Val Tyr Leu Thr Met Asn Thr Ser Ser Leu Val Leu Ala Lys Pro Ile
        35                  40                  45

Glu Asn Thr Asn Asp Thr Ser Ile Lys Asn Val Glu Lys Leu Arg Asn
    50                  55                  60

Ala Pro Asn Glu Glu Asn Ser Lys Lys Val Glu Asp Ser Lys Asn Asp
65                  70                  75                  80

Lys Val Glu His Val Lys Asn Ile Glu Glu Ala Lys Val Glu Gln Val
                85                  90                  95

Ala Pro Glu Val Lys Ser Lys Ser Thr Leu Arg Ser Ala Ser Ile Ala
            100                 105                 110

Asn Thr Asn Ser Glu Lys Tyr Asp Phe Glu Tyr Leu Asn Gly Leu Ser
        115                 120                 125

Tyr Thr Glu Leu Thr Asn Leu Ile Lys Asn Ile Lys Trp Asn Gln Ile
    130                 135                 140

Asn Gly Leu Phe Asn Tyr Ser Thr Gly Ser Gln Lys Phe Phe Gly Asp
145                 150                 155                 160

Lys Asn Arg Val Gln Ala Ile Ile Asn Ala Leu Gln Glu Ser Gly Arg
                165                 170                 175

Thr Tyr Thr Ala Asn Asp Met Lys Gly Ile Glu Thr Phe Thr Glu Val
            180                 185                 190

Leu Arg Ala Gly Phe Tyr Leu Gly Tyr Tyr Asn Asp Gly Leu Ser Tyr
        195                 200                 205

Leu Asn Asp Arg Asn Phe Gln Asp Lys Cys Ile Pro Ala Met Ile Ala
    210                 215                 220

Ile Gln Lys Asn Pro Asn Phe Lys Leu Gly Thr Ala Val Gln Asp Glu
225                 230                 235                 240

Val Ile Thr Ser Leu Gly Lys Leu Ile Gly Asn Ala Ser Ala Asn Ala
                245                 250                 255

Glu Val Val Asn Asn Cys Val Pro Val Leu Lys Gln Phe Arg Glu Asn
            260                 265                 270

Leu Asn Gln Tyr Ala Pro Asp Tyr Val Lys Gly Thr Ala Val Asn Glu
        275                 280                 285

Leu Ile Lys Gly Ile Glu Phe Asp Phe Ser Gly Ala Ala Tyr Glu Lys
    290                 295                 300

Asp Val Lys Thr Met Pro Trp Tyr Gly Lys Ile Asp Pro Phe Ile Asn
305                 310                 315                 320

Glu Leu Lys Ala Leu Gly Leu Tyr Gly Asn Ile Thr Ser Ala Thr Glu
                325                 330                 335

Trp Ala Ser Asp Val Gly Ile Tyr Tyr Leu Ser Lys Phe Gly Leu Tyr
            340                 345                 350

Ser Thr Asn Arg Asn Asp Ile Val Gln Ser Leu Glu Lys Ala Val Asp
        355                 360                 365
```

```
Met Tyr Lys Tyr Gly Lys Ile Ala Phe Val Ala Met Glu Arg Ile Thr
    370             375             380
Trp Asp Tyr Asp Gly Ile Gly Ser Asn Gly Lys Lys Val Asp His Asp
385             390             395             400
Lys Phe Leu Asp Asp Ala Glu Lys His Tyr Leu Pro Lys Thr Tyr Thr
                405             410             415
Phe Asp Asn Gly Thr Phe Ile Ile Arg Ala Gly Asp Lys Val Ser Glu
            420             425             430
Glu Lys Ile Lys Arg Leu Tyr Trp Ala Ser Arg Glu Val Lys Ser Gln
        435             440             445
Phe His Arg Val Val Gly Asn Asp Lys Ala Leu Glu Val Gly Asn Ala
    450             455             460
Asp Asp Val Leu Thr Met Lys Ile Phe Asn Ser Pro Glu Glu Tyr Lys
465             470             475             480
Phe Asn Thr Asn Ile Asn Gly Val Ser Thr Asp Asn Gly Gly Leu Tyr
                485             490             495
Ile Glu Pro Arg Gly Thr Phe Tyr Thr Tyr Glu Arg Thr Pro Gln Gln
            500             505             510
Ser Ile Phe Ser Leu Glu Glu Leu Phe Arg His Glu Tyr Thr His Tyr
        515             520             525
Leu Gln Ala Arg Tyr Leu Val Asp Gly Leu Trp Gly Gln Gly Pro Phe
    530             535             540
Tyr Glu Lys Asn Arg Leu Thr Trp Phe Asp Glu Gly Thr Ala Glu Phe
545             550             555             560
Phe Ala Gly Ser Thr Arg Thr Ser Gly Val Leu Pro Arg Lys Ser Ile
                565             570             575
Leu Gly Tyr Leu Ala Lys Asp Lys Val Asp His Arg Tyr Ser Leu Lys
            580             585             590
Lys Thr Leu Asn Ser Gly Tyr Asp Asp Ser Asp Trp Met Phe Tyr Asn
        595             600             605
Tyr Gly Phe Ala Val Ala His Tyr Leu Tyr Glu Lys Asp Met Pro Thr
    610             615             620
Phe Ile Lys Met Asn Lys Ala Ile Leu Asn Thr Asp Val Lys Ser Tyr
625             630             635             640
Asp Glu Ile Ile Lys Lys Leu Ser Asp Ala Asn Lys Asn Thr Glu
                645             650             655
Tyr Gln Asn His Ile Gln Glu Leu Ala Asp Lys Tyr Gln Gly Ala Gly
            660             665             670
Ile Pro Leu Val Ser Asp Asp Tyr Leu Lys Asp His Gly Tyr Lys Lys
        675             680             685
Ala Ser Glu Val Tyr Ser Glu Ile Ser Lys Ala Ser Leu Thr Asn
    690             695             700
Thr Ser Val Thr Ala Glu Lys Ser Gln Tyr Phe Asn Thr Phe Thr Leu
705             710             715             720
Arg Gly Thr Tyr Thr Gly Glu Thr Ser Lys Gly Glu Phe Lys Asp Trp
                725             730             735
Asp Glu Met Ser Lys Lys Leu Asp Gly Thr Leu Glu Ser Leu Ala Lys
            740             745             750
Asn Ser Trp Ser Gly Tyr Lys Thr Leu Thr Ala Tyr Phe Thr Asn Tyr
        755             760             765
Arg Val Thr Ser Asp Asn Lys Val Gln Tyr Asp Val Val Phe His Gly
    770             775             780
Val Leu Thr Asp Asn Ala Asp Ile Ser Asn Asn Lys Ala Pro Ile Ala
```

-continued

```
785                 790                 795                 800

Lys Val Thr Gly Pro Ser Thr Gly Ala Val Gly Arg Asn Ile Glu Phe
                805                 810                 815

Ser Gly Lys Asp Ser Lys Asp Glu Asp Gly Lys Ile Val Ser Tyr Asp
            820                 825                 830

Trp Asp Phe Gly Asp Gly Ala Thr Ser Arg Gly Lys Asn Ser Val His
        835                 840                 845

Ala Tyr Lys Lys Ala Gly Thr Tyr Asn Val Thr Leu Lys Val Thr Asp
    850                 855                 860

Asp Lys Gly Ala Thr Ala Thr Glu Ser Phe Thr Ile Glu Ile Lys Asn
865                 870                 875                 880

Glu Asp Thr Thr Thr Pro Ile Thr Lys Glu Met Glu Pro Asn Asp Asp
                885                 890                 895

Ile Lys Glu Ala Asn Gly Pro Ile Val Glu Gly Val Thr Val Lys Gly
            900                 905                 910

Asp Leu Asn Gly Ser Asp Asp Ala Asp Thr Phe Tyr Phe Asp Val Lys
        915                 920                 925

Glu Asp Gly Asp Val Thr Ile Glu Leu Pro Tyr Ser Gly Ser Ser Asn
    930                 935                 940

Phe Thr Trp Leu Val Tyr Lys Glu Gly Asp Asp Gln Asn His Ile Ala
945                 950                 955                 960

Ser Gly Ile Asp Lys Asn Asn Ser Lys Val Gly Thr Phe Lys Ser Thr
                965                 970                 975

Lys Gly Arg His Tyr Val Phe Ile Tyr Lys His Asp Ser Ala Ser Asn
            980                 985                 990

Ile Ser Tyr Ser Leu Asn Ile Lys  Gly Leu Gly Asn Glu  Lys Leu Lys
        995                 1000                1005

Glu Lys  Glu Asn Asn Asp Ser  Ser Asp Lys Ala Thr  Val Ile Pro
    1010                1015                1020

Asn Phe  Asn Thr Thr Met Gln  Gly Ser Leu Leu Gly  Asp Asp Ser
    1025                1030                1035

Arg Asp  Tyr Tyr Ser Phe Glu  Val Lys Glu Glu Gly  Glu Val Asn
    1040                1045                1050

Ile Glu  Leu Asp Lys Lys Asp  Glu Phe Gly Val Thr  Trp Thr Leu
    1055                1060                1065

His Pro  Glu Ser Asn Ile Asn  Asp Arg Ile Thr Tyr  Gly Gln Val
    1070                1075                1080

Asp Gly  Asn Lys Val Ser Asn  Lys Val Lys Leu Arg  Pro Gly Lys
    1085                1090                1095

Tyr Tyr  Leu Leu Val Tyr Lys  Tyr Ser Gly Ser Gly  Asn Tyr Glu
    1100                1105                1110

Leu Arg  Val Asn Lys
    1115

<210> SEQ ID NO 2
<211> LENGTH: 1021
<212> TYPE: PRT
<213> ORGANISM: Clostridium histolyticum

<400> SEQUENCE: 2

Met Lys Arg Lys Cys Leu Ser Lys Arg Leu Met Leu Ala Ile Thr Met
1               5                   10                  15

Ala Thr Ile Phe Thr Val Asn Ser Thr Leu Pro Ile Tyr Ala Ala Val
            20                  25                  30
```

-continued

```
Asp Lys Asn Asn Ala Thr Ala Ala Val Gln Asn Glu Ser Lys Arg Tyr
         35                  40                  45
Thr Val Ser Tyr Leu Lys Thr Leu Asn Tyr Tyr Asp Leu Val Asp Leu
 50                  55                  60
Leu Val Lys Thr Glu Ile Glu Asn Leu Pro Asp Leu Phe Gln Tyr Ser
 65                  70                  75                  80
Ser Asp Ala Lys Glu Phe Tyr Gly Asn Lys Thr Arg Met Ser Phe Ile
                 85                  90                  95
Met Asp Glu Ile Gly Arg Arg Ala Pro Gln Tyr Thr Glu Ile Asp His
                100                 105                 110
Lys Gly Ile Pro Thr Leu Val Glu Val Arg Ala Gly Phe Tyr Leu
            115                 120                 125
Gly Phe His Asn Lys Glu Leu Asn Glu Ile Asn Lys Arg Ser Phe Lys
130                 135                 140
Glu Arg Val Ile Pro Ser Ile Leu Ala Ile Gln Lys Asn Pro Asn Phe
145                 150                 155                 160
Lys Leu Gly Thr Glu Val Gln Asp Lys Ile Val Ser Ala Thr Gly Leu
                165                 170                 175
Leu Ala Gly Asn Glu Thr Ala Pro Pro Glu Val Val Asn Asn Phe Thr
                180                 185                 190
Pro Ile Leu Gln Asp Cys Ile Lys Asn Ile Asp Arg Tyr Ala Leu Asp
            195                 200                 205
Asp Leu Lys Ser Lys Ala Leu Phe Asn Val Leu Ala Ala Pro Thr Tyr
            210                 215                 220
Asp Ile Thr Glu Tyr Leu Arg Ala Thr Lys Glu Lys Pro Glu Asn Thr
225                 230                 235                 240
Pro Trp Tyr Gly Lys Ile Asp Gly Phe Ile Asn Glu Leu Lys Lys Leu
                245                 250                 255
Ala Leu Tyr Gly Lys Ile Asn Asp Asn Asn Ser Trp Ile Ile Asp Asn
            260                 265                 270
Gly Ile Tyr His Ile Ala Pro Leu Gly Lys Leu His Ser Asn Asn Lys
            275                 280                 285
Ile Gly Ile Glu Thr Leu Thr Glu Val Met Lys Val Tyr Pro Tyr Leu
290                 295                 300
Ser Met Gln His Leu Gln Ser Ala Asp Gln Ile Lys Arg His Tyr Asp
305                 310                 315                 320
Ser Lys Asp Ala Glu Gly Asn Lys Ile Pro Leu Asp Lys Phe Lys Lys
                325                 330                 335
Glu Gly Lys Glu Lys Tyr Cys Pro Lys Thr Tyr Thr Phe Asp Asp Gly
            340                 345                 350
Lys Val Ile Ile Lys Ala Gly Ala Arg Val Glu Glu Lys Val Lys
            355                 360                 365
Arg Leu Tyr Trp Ala Ser Lys Glu Val Asn Ser Gln Phe Phe Arg Val
370                 375                 380
Tyr Gly Ile Asp Lys Pro Leu Glu Glu Gly Asn Pro Asp Asp Ile Leu
385                 390                 395                 400
Thr Met Val Ile Tyr Asn Ser Pro Glu Glu Tyr Lys Leu Asn Ser Val
                405                 410                 415
Leu Tyr Gly Tyr Asp Thr Asn Asn Gly Gly Met Tyr Ile Glu Pro Glu
                420                 425                 430
Gly Thr Phe Phe Thr Tyr Glu Arg Glu Ala Gln Glu Ser Thr Tyr Thr
            435                 440                 445
Leu Glu Glu Leu Phe Arg His Glu Tyr Thr His Tyr Leu Gln Gly Arg
```

```
                450               455               460
    Tyr Ala Val Pro Gly Gln Trp Gly Arg Thr Lys Leu Tyr Asp Asn Asp
    465                 470                 475                 480

Arg Leu Thr Trp Tyr Glu Gly Gly Ala Glu Leu Phe Ala Gly Ser
                    485                 490                 495

Thr Arg Thr Ser Gly Ile Leu Pro Arg Lys Ser Ile Val Ser Asn Ile
                500                 505                 510

His Asn Thr Thr Arg Asn Asn Arg Tyr Lys Leu Ser Asp Thr Val His
                515                 520                 525

Ser Lys Tyr Gly Ala Ser Phe Glu Phe Tyr Asn Tyr Ala Cys Met Phe
            530                 535                 540

Met Asp Tyr Met Tyr Asn Lys Asp Met Gly Ile Leu Asn Lys Leu Asn
    545                 550                 555                 560

Asp Leu Ala Lys Asn Asn Asp Val Asp Gly Tyr Asp Asn Tyr Ile Arg
                    565                 570                 575

Asp Leu Ser Ser Asn Tyr Ala Leu Asn Asp Lys Tyr Gln Asp His Met
                580                 585                 590

Gln Glu Arg Ile Asp Asn Tyr Glu Asn Leu Thr Val Pro Phe Val Ala
                595                 600                 605

Asp Asp Tyr Leu Val Arg His Ala Tyr Lys Asn Pro Asn Glu Ile Tyr
    610                 615                 620

Ser Glu Ile Ser Glu Val Ala Lys Leu Lys Asp Ala Lys Ser Glu Val
    625                 630                 635                 640

Lys Lys Ser Gln Tyr Phe Ser Thr Phe Thr Leu Arg Gly Ser Tyr Thr
                    645                 650                 655

Gly Gly Ala Ser Lys Gly Lys Leu Glu Asp Gln Lys Ala Met Asn Lys
                660                 665                 670

Phe Ile Asp Asp Ser Leu Lys Lys Leu Asp Thr Tyr Ser Trp Ser Gly
                675                 680                 685

Tyr Lys Thr Leu Thr Ala Tyr Phe Thr Asn Tyr Lys Val Asp Ser Ser
    690                 695                 700

Asn Arg Val Thr Tyr Asp Val Val Phe His Gly Tyr Leu Pro Asn Glu
    705                 710                 715                 720

Gly Asp Ser Lys Asn Ser Leu Pro Tyr Gly Lys Ile Asn Gly Thr Tyr
                    725                 730                 735

Lys Gly Thr Glu Lys Glu Lys Ile Lys Phe Ser Ser Glu Gly Ser Phe
                740                 745                 750

Asp Pro Asp Gly Lys Ile Val Ser Tyr Glu Trp Asp Phe Gly Asp Gly
                755                 760                 765

Asn Lys Ser Asn Glu Glu Asn Pro Glu His Ser Tyr Asp Lys Val Gly
                770                 775                 780

Thr Tyr Thr Val Lys Leu Lys Val Thr Asp Asp Lys Gly Glu Ser Ser
    785                 790                 795                 800

Val Ser Thr Thr Thr Ala Glu Ile Lys Asp Leu Ser Glu Asn Lys Leu
                    805                 810                 815

Pro Val Ile Tyr Met His Val Pro Lys Ser Gly Ala Leu Asn Gln Lys
                820                 825                 830

Val Val Phe Tyr Gly Lys Gly Thr Tyr Asp Pro Asp Gly Ser Ile Ala
                835                 840                 845

Gly Tyr Gln Trp Asp Phe Gly Asp Gly Ser Asp Phe Ser Ser Glu Gln
            850                 855                 860

Asn Pro Ser His Val Tyr Thr Lys Lys Gly Glu Tyr Thr Val Thr Leu
    865                 870                 875                 880
```

```
                                                -continued

Arg Val Met Asp Ser Ser Gly Gln Met Ser Glu Lys Thr Met Lys Ile
                885                 890                 895

Lys Ile Thr Asp Pro Val Tyr Pro Ile Gly Thr Glu Lys Glu Pro Asn
                900                 905                 910

Asn Ser Lys Glu Thr Ala Ser Gly Pro Ile Val Pro Gly Ile Pro Val
            915                 920                 925

Ser Gly Thr Ile Glu Asn Thr Ser Asp Gln Asp Tyr Phe Tyr Phe Asp
        930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
                965                 970                 975

Tyr Ala Thr Asp Asp Gly Gln Asn Leu Ser Gly Lys Phe Lys Ala Asp
                980                 985                 990

Lys Pro Gly Arg Tyr Tyr Ile His Leu Tyr Met Phe Asn Gly Ser Tyr
            995                 1000                1005

Met Pro Tyr Arg Ile Asn Ile  Glu Gly Ser Val Gly  Arg
    1010                1015                1020
```